US012172027B2

(12) United States Patent
Bhawalkar et al.

(10) Patent No.: US 12,172,027 B2
(45) Date of Patent: Dec. 24, 2024

(54) FEEDBACK DETECTION FOR A TREATMENT DEVICE

(71) Applicant: Avava, Inc., Waltham, MA (US)

(72) Inventors: Jayant Bhawalkar, Auburndale, MA (US); Rajender Katkam, Boston, MA (US); Lewis J. Levine, Marlborough, MA (US); Charles Holland Dresser, Wayland, MA (US)

(73) Assignee: Avava, Inc., Waltham, MA (US)

( * ) Notice: Subject to any disclaimer, the term of this patent is extended or adjusted under 35 U.S.C. 154(b) by 608 days.

(21) Appl. No.: 17/094,394

(22) Filed: Nov. 10, 2020

(65) Prior Publication Data

US 2021/0138261 A1   May 13, 2021

Related U.S. Application Data

(60) Provisional application No. 62/934,583, filed on Nov. 13, 2019.

(51) Int. Cl.
*A61N 5/06* (2006.01)
*A61M 35/00* (2006.01)
(Continued)

(52) U.S. Cl.
CPC ......... *A61N 5/0616* (2013.01); *A61M 35/003* (2013.01); *A61B 2017/0019* (2013.01);
(Continued)

(58) Field of Classification Search
CPC ........ A61B 18/203; A61B 2018/00023; A61B 10/02; A61B 10/0283; A61B 17/22031; A61B 17/320016; A61B 17/32056; A61B 17/320783; A61B 17/3478; A61B 18/02; A61B 18/1477; A61B 18/1492; A61B 18/22; A61B 18/24; A61B 2017/00092;
(Continued)

(56) References Cited

U.S. PATENT DOCUMENTS

| 5,849,029 A | 12/1998 | Eckhouse et al. |
| 10,617,468 B1 | 4/2020 | Dresser et al. |

(Continued)

FOREIGN PATENT DOCUMENTS

| JP | H07503382 A | 4/1995 |
| JP | H09187522 A | 7/1997 |

(Continued)

OTHER PUBLICATIONS

International Search Report and Written Opinion issued in corresponding International Application No. PCT/US20/59842, Feb. 4, 2021, 12 pages.

*Primary Examiner* — Scott Luan
(74) *Attorney, Agent, or Firm* — Mintz Levin Cohn Ferris Glovsky and Popeo, P.C.

(57) ABSTRACT

According to some embodiments, a system for fractionally treating tissue includes: an electromagnetic radiation (EMR) source configured to generate an EMR beam having a transverse ring energy profile; an optic configured to converge the EMR beam to a focal region located within a tissue; and, a window assembly located down-beam from the optic configured to cool the tissue when placed in contact with an outer surface of the tissue.

17 Claims, 48 Drawing Sheets
(4 of 48 Drawing Sheet(s) Filed in Color)

(51) Int. Cl.
*A61B 17/00* (2006.01)
*A61B 18/00* (2006.01)
*A61N 5/00* (2006.01)

(52) U.S. Cl.
CPC .............. *A61B 2018/00702* (2013.01); *A61N 2005/007* (2013.01); *A61N 2005/0626* (2013.01); *A61N 2005/0659* (2013.01)

(58) Field of Classification Search
CPC .......... A61B 2017/00119; A61B 2017/00269; A61B 2017/00539; A61B 2017/2937; A61B 2017/320048; A61B 2018/00011; A61B 2018/00029; A61B 2018/00291; A61B 2018/00452; A61B 2018/00464; A61B 2018/00476; A61B 2018/00583; A61B 2018/0212; A61B 2018/0262; A61B 2018/1407; A61B 2018/1425; A61B 2018/1807; A61B 2090/065; A61B 2560/0271; A61B 2562/0295; A61B 5/0002; A61B 5/01; A61B 5/14532; A61B 5/1455; A61B 5/1495
See application file for complete search history.

(56) References Cited

U.S. PATENT DOCUMENTS

| | | | |
|---|---|---|---|
| 10,973,578 B2 | 4/2021 | Anderson et al. | |
| 2004/0158301 A1 | 8/2004 | Tucek et al. | |
| 2005/0143793 A1 | 6/2005 | Korman et al. | |
| 2006/0020309 A1* | 1/2006 | Altshuler ............. | A61H 39/002 607/88 |
| 2008/0255034 A1 | 10/2008 | Bohler et al. | |
| 2008/0287930 A1 | 11/2008 | Rapoport | |
| 2009/0099559 A1 | 4/2009 | Dhadwal | |
| 2009/0304033 A1 | 12/2009 | Ogilvy et al. | |
| 2010/0100085 A1 | 4/2010 | Lewinsky et al. | |
| 2011/0137303 A1 | 6/2011 | Dolleris et al. | |
| 2011/0190749 A1 | 8/2011 | Mcmillan et al. | |
| 2011/0218599 A1 | 9/2011 | Shanks et al. | |
| 2012/0095533 A1* | 4/2012 | Wang .................. | A61N 5/0613 607/89 |
| 2012/0147912 A1 | 6/2012 | Moench et al. | |
| 2012/0179227 A1* | 7/2012 | Schomacker ........ | A61B 18/203 607/89 |
| 2012/0330288 A1 | 12/2012 | Clementi et al. | |
| 2013/0345687 A1 | 12/2013 | McMillan et al. | |
| 2014/0200564 A1 | 7/2014 | Schomacker et al. | |
| 2014/0330258 A1 | 11/2014 | Iger | |
| 2015/0005755 A1 | 1/2015 | Kazic et al. | |
| 2015/0025599 A1* | 1/2015 | Bornstein ............ | A61N 5/0613 607/88 |
| 2015/0062573 A1* | 3/2015 | Liu ........................ | A61B 5/444 356/300 |
| 2015/0265351 A1 | 9/2015 | Haight et al. | |
| 2016/0157935 A1 | 6/2016 | Jurna et al. | |
| 2016/0199132 A1 | 7/2016 | Anderson et al. | |
| 2016/0271419 A1 | 9/2016 | Varghese et al. | |
| 2017/0035508 A1 | 2/2017 | Dhadwal | |
| 2018/0119238 A1 | 5/2018 | Dajnowski | |
| 2018/0251865 A1 | 9/2018 | Dajnowski | |
| 2018/0296269 A1 | 10/2018 | Bhawalkar et al. | |
| 2019/0187461 A1 | 6/2019 | Dresser et al. | |
| 2019/0314085 A1 | 10/2019 | Dresser et al. | |
| 2021/0376553 A1 | 12/2021 | Shang et al. | |
| 2023/0031007 A1 | 2/2023 | Grossman et al. | |
| 2024/0131354 A1 | 4/2024 | Bhawalkar et al. | |

FOREIGN PATENT DOCUMENTS

| | | |
|---|---|---|
| JP | 2017506935 A | 3/2017 |
| WO | 9308877 A1 | 5/1993 |
| WO | 2014132146 A1 | 9/2014 |
| WO | 2015110273 A1 | 7/2015 |
| WO | 2019118758 A2 | 6/2019 |
| WO | 2021096863 A1 | 5/2021 |

* cited by examiner

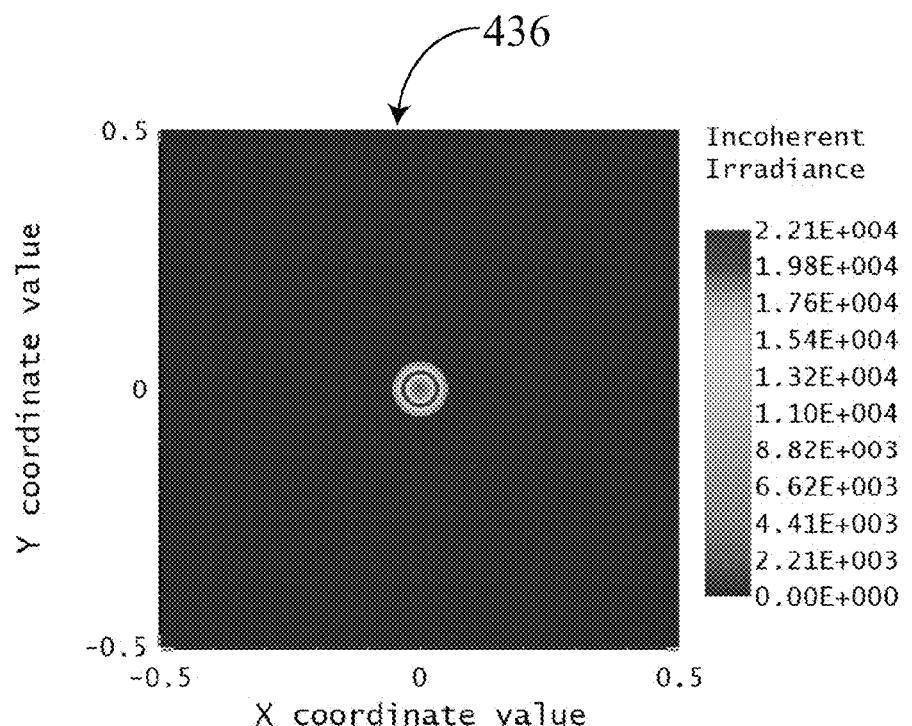
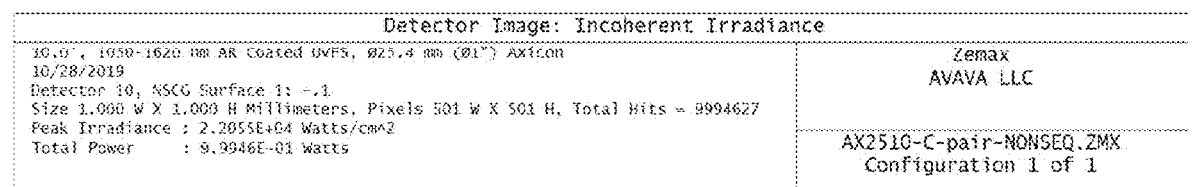
*FIG. 4E*

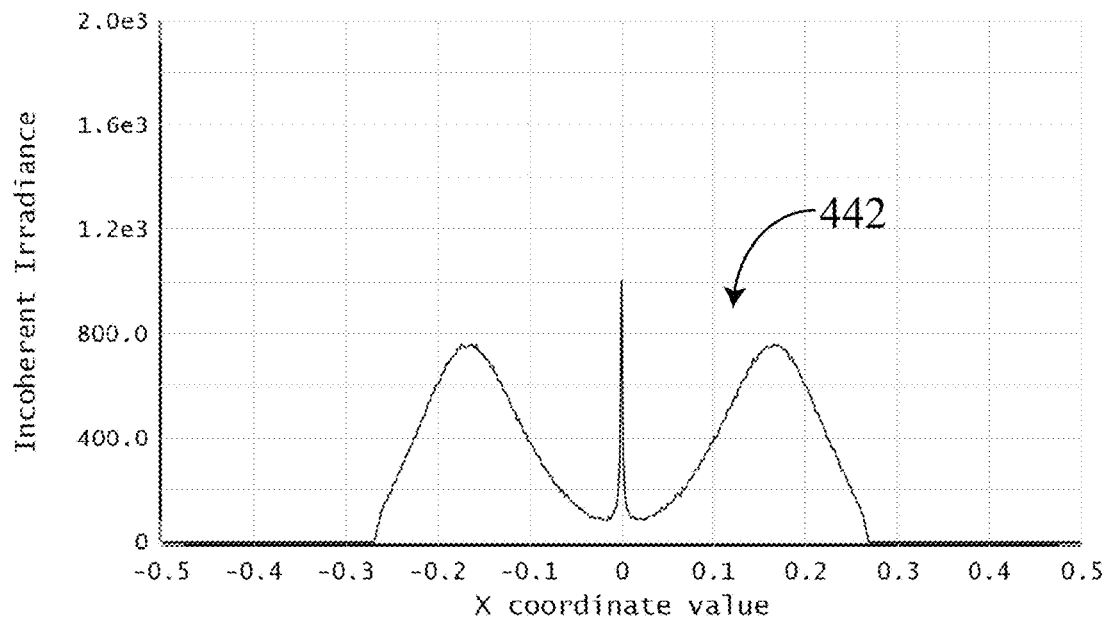
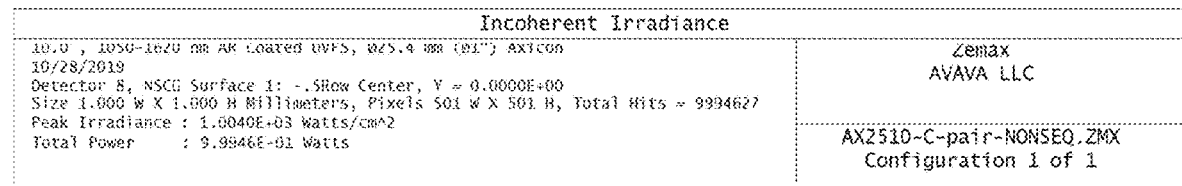
FIG. 4G

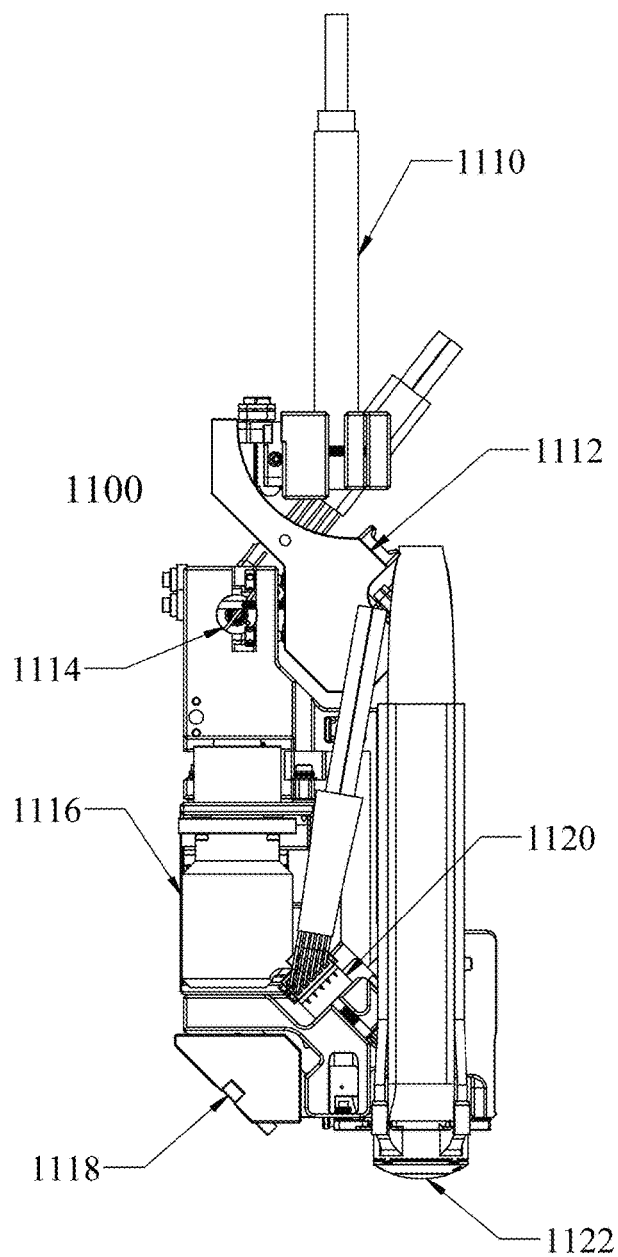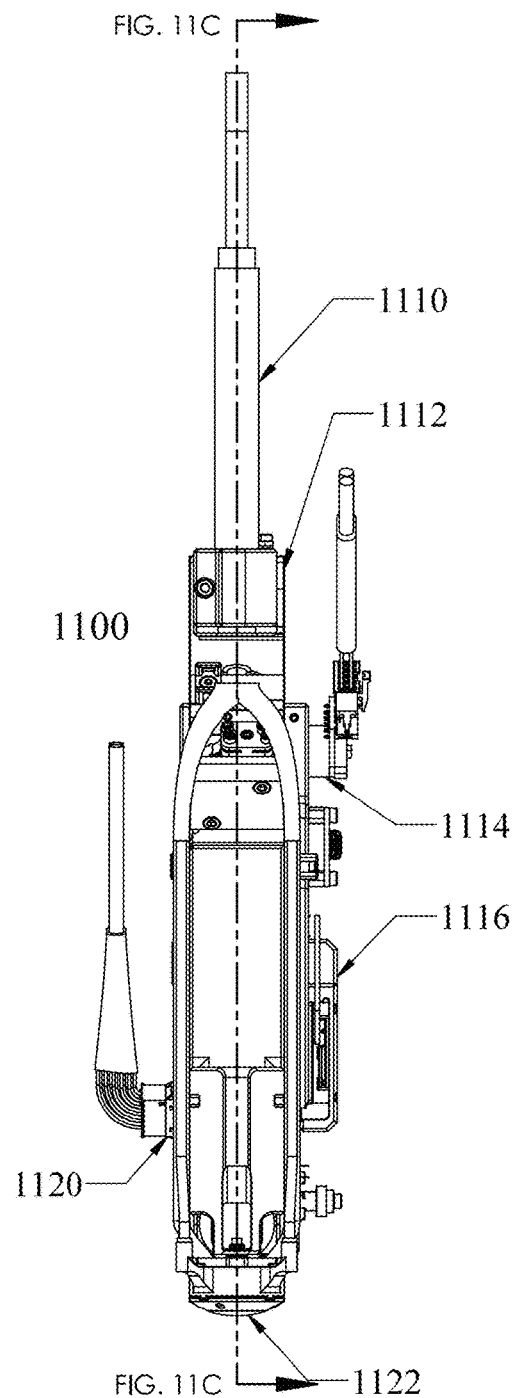
FIG. 11A   FIG. 11B

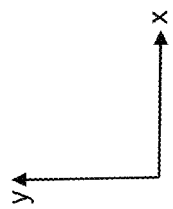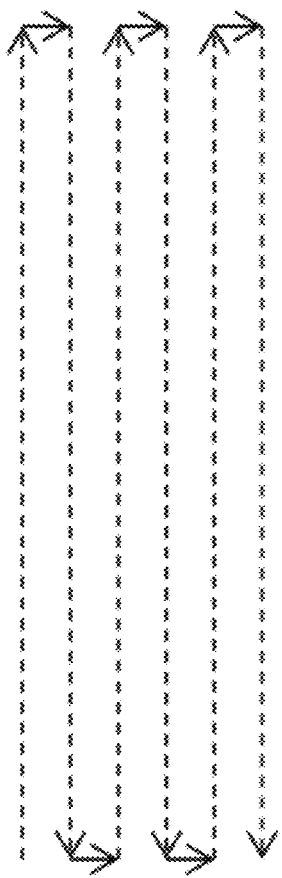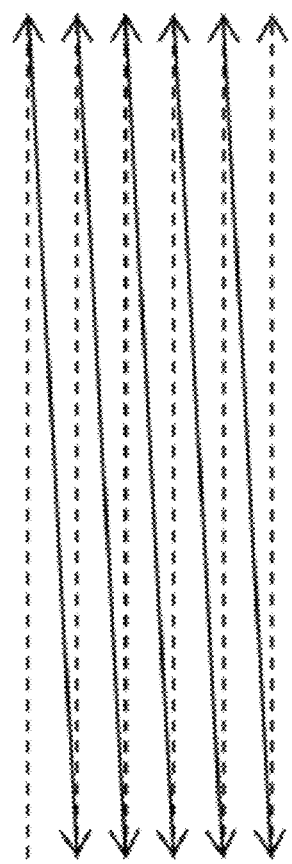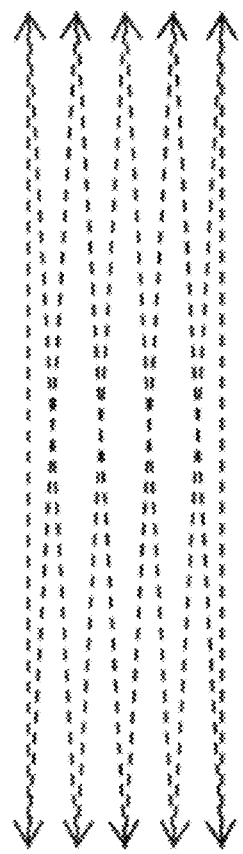

FEEDBACK DETECTION FOR A TREATMENT DEVICE

CROSS-REFERENCE TO RELATED APPLICATIONS

This application claims the benefit of U.S. Provisional Patent Application No. 62/934,583, filed on Nov. 13, 2019, and entitled "Electromagnetic Radiation Based Treatment Devices and Methods," the entirety of which is incorporated by reference herein.

BACKGROUND

Presently a number of energy-based devices are available for fractionated treatment of the dermis. These methods include ablative lasers, non-ablative lasers, micro-needling, and RF energy treatments. Generally, these presently available fractionated energy-based treatments require damage to outer portions of skin undergoing treatment (e.g., epidermis). Damage to the epidermis, in most cases, causes the skin to appear inflamed, blemished, or unhealthy immediately after treatment. Additionally, severe damage to the epidermis can lead to one or more of infection and a need for additional medical treatment. This undesirable appearance results in a post-treatment downtime that lasts until the epidermis has healed, which may take days to weeks depending on treatment parameters used (e.g., ablative vs. non-ablative). Most patients do not return to their normal lives until after the post-treatment down-time. It is therefore desirable that a fractionated treatment system and method be made available, which can successfully affect the dermis while minimizing damage to the epidermis in order to minimize post-treatment downtime.

SUMMARY

Skin rejuvenation is often performed through fractional treatment. Fractional or fractionated energy-based treatment refers to a treatment in which only a fraction of an area of tissue is exposed to energy. For example, a fractional skin treatment may treat 25% of an area of skin with a laser beam and leave a remaining 75% of skin in that area untreated. Energy-based skin rejuvenation involves creating controlled small injury within a collagen network. The small injury causes a wound healing process in which new collagen is formed. The newly formed collagen tightens the skin, thereby causing the skin to appear more youthful. Many skin rejuvenation fractionated treatment systems work by targeting water as a chromophore achieving photothermolysis.

Fractionated treatment can generally be divided into two categories: Ablative and non-ablative. Ablative treatment causes removal of tissue and results in superficial micro-injury in addition to creating thermal damage within the dermis. Non-ablative treatment typically does not cause tissue removal, instead causing only thermal disruption. An advantage of non-ablative fractionated treatment over ablative fractionated treatment is a reduction in down-time.

Energy-based fractionated treatment of tissue generally requires that a high amount of energy be delivered to and absorbed by a selective portion of tissue to effect a desired disruption or damage. This disruption or damage is repeated over an area of tissue, so that small regions (e.g., 0.1 to 10 mm in diameter) of disrupted tissue are interlaced with undamaged tissue. The small regions of damaged tissue are then replaced with new tissue during a post-treatment healing process. Inducing damage within a dermis layer of skin while minimizing damage to an overlying epidermis layer presents a number of technical challenges, some of which are enumerated below.

First, there is no known chromophore within the dermis layer of tissue which is not present within the epidermis layer of tissue. This means that a radiation selected to absorb within the dermis will also be absorbed within the epidermis layer.

Second, as the EMR will be equally well absorbed by the epidermis layer and the dermis layer of the skin, a greater energy density must be delivered to the dermis layer than to the epidermis. In order to achieve this, the EMR profile must be varied, such that a focal region (i.e., region of maximum energy density) of the EMR beam is located within the dermis and only an unfocused region (i.e., region of minimum energy density) of the EMR beam subtends the epidermis layer of the skin.

Third, skin tissue is a turbid medium, meaning that radiation propagating through skin scatters. The scattering of radiation within skin tissue, makes it more difficult to form a focal region (region of maximum energy density) at any depth within the tissue, compounding the first and second challenges above.

Fourth, the focal region (or region of maximum energy density) must be accurately positioned at a depth within the dermis layer of the skin. This ensures that the region of maximum energy density is located in the dermis and not located within the epidermis, in order to prevent unwanted damage to the epidermis.

Fifth, the EMR beam is delivered from outside the tissue; and, therefore, the epidermis experiences some minimal irradiation and minor thermal heating (i.e., less than the dermis). In response to this fifth challenge, the epidermis layer directly overly the dermis layer being treated must be actively cooled to prevent thermal damage to the epidermis.

Therefore, to provide fractionated therapeutic disruption to the dermis layer of a skin tissue, while minimizing damage to overlying epidermal layers, a need exists for fractionated treatment systems and methods that address all of the above-mentioned challenges.

According to some embodiments, a system for fractionally treating tissue includes: an electromagnetic radiation (EMR) source configured to generate an EMR beam having a transverse ring energy profile; an optic configured to converge the EMR beam to a focal region located within a tissue; and, a window assembly located down-beam from the optic configured to cool the tissue when placed in contact with an outer surface of the tissue. The window assembly includes: a first window, a second window separated from the first window; and, a coolant chamber located between the first window and the second window, wherein the coolant chamber is configured to contain a coolant that is substantially non-absorbent of the EMR beam.

In some embodiments of the system, the EMR beam has a wavelength in a range between about 1000 nm and 4000 nm.

In some embodiments of the system, the coolant includes at least one of a dielectric fluid, a fluorocarbon-based fluid, water, an antifreeze, ethylene glycol, and propylene glycol.

In some embodiments of the system, the optic is additionally configured to converge the EMR beam at a numerical aperture (NA) of at least about 0.2.

In some embodiments of the system, the system also includes an optical clearing medium located between the window assembly and the tissue. In some cases, the optical clearing medium includes at least one of: glycerin, polyethylene glycol, and phosphate-buffered saline.

In some embodiments of the system, the EMR source includes a beam shaper configured to shape the transverse ring energy profile. In some versions of the system, the beam shaper includes an axicon.

In some embodiments of the system, the system additionally includes a controller. In some cases, the controller is configured to control the EMR source to ensure that the window assembly cools the tissue to a determined temperature prior to generating the EMR beam. In some cases, the controller is configured to control the EMR source to ensure that the window assembly cools the tissue for a determined period prior to generating the EMR beam.

According to some embodiments, a method for fractionally treating tissue includes: cooling, using a window assembly contacting an outer surface of the tissue, the tissue; generating, using an electromagnetic radiation (EMR) source, an EMR beam having a transverse ring energy profile; and converging, using an optic, the EMR beam to a focal region located within a tissue. In some cases, the window assembly includes: a first window, a second window separated from the first window, and a coolant chamber located between the first window and the second window; wherein, the coolant chamber is configured to contain a coolant that is substantially non-absorbent of the EMR beam.

In some embodiments of the method, the EMR beam has a wavelength in a range between about 1000 nm and 4000 nm.

In some embodiments of the method, the coolant includes at least one of a dielectric fluid, a fluorocarbon-based fluid, water, ethylene glycol, and propylene glycol.

In some embodiments of the method, converging the EMR beam is performed at a numerical aperture (NA) of at least about 0.2.

In some embodiments of the method, the method additionally includes introducing an optical tissue clearing medium between the window assembly and the tissue. In some cases, the optical tissue clearing medium includes at least one of glycerin, polyethylene glycol, and phosphate-buffered saline.

In some embodiments of the method, the EMR source additionally includes a beam shaper configured to shape the transverse ring energy profile. In some versions of the method, the beam shaper includes an axicon.

In some embodiments of the method, the method additionally includes controlling, using a controller, the EMR source in order to ensure that the window assembly cools the tissue to a determined temperature prior to generating the EMR beam.

In some embodiments of the method, the method additionally includes controlling, using a controller, the EMR source in order to ensure that the window assembly cools the tissue for a determined period prior to generating the EMR beam.

According to some embodiments, a system for fractionally treating tissue includes: an electromagnetic radiation (EMR) source configured to generate an EMR beam having a wavelength in a range between about 1400 nm and 3400 nm; a beam shaper configured to shape the EMR beam into a transverse ring energy profile, wherein the beam shaper includes an axicon; an optic configured to converge the EMR beam at a numerical aperture (NA) of at least about 0.2 to a focal region located within a tissue; a window assembly located down-beam from the optic configured to cool the tissue when placed in contact with an outer surface of the tissue, wherein the window assembly includes: a first window, a second window separated from the first window, and a coolant chamber located between the first window and the second window, wherein the coolant chamber is configure to contain a coolant that is substantially non-absorbent of the EMR beam and includes a fluorocarbon-based fluid; and a controller configured to control the EMR source in order to ensure that the window assembly cools the tissue at least one of: to a determined temperature and for a determined time prior to generating the EMR beam.

According to some embodiments, a system for fractionally treating tissue includes: an electromagnetic radiation (EMR) source configured to generate an EMR beam having a wavelength; a collimator configured to collimate the EMR beam to a width; a beam shaper includes a first axicon and a second axicon configured to shape the collimated EMR beam into a transverse ring energy profile, wherein the first axicon and the second axicon are separated by a distance along an optical axis that is chosen to effect a desired inner diameter of the transverse ring energy profile and the width of the collimated EMR beam is chosen to effect a desired thickness of the transverse energy profile; and an optic configured to converge the EMR beam to a focal region within a tissue, thereby affecting the tissue with the focal region.

According to some embodiments, a system includes: an EMR source configured to generate an EMR beam having a transverse ring-shaped energy profile and a wavelength in a range of about 1200 nm to about 12000 nm; an optic configured to converge the EMR beam to a focal region located within a tissue; a beam scanning system configured to scan the focal region within the tissue; a window assembly located down-beam from the optic configured to transmit the EMR beam and cool the tissue when placed in contact with an outer surface of the tissue, wherein the window assembly includes: a first window; a second window separated from the first window; and, a coolant chamber located between the first window and the second window, wherein the coolant chamber is configured to contain a coolant including a fluorocarbon-based fluid that is substantially non-absorbent of the EMR beam; and a controller configured to control the EMR source to generate the EMR beam with a plurality of pulses, wherein at least one pulse of the plurality of pulses has a pulse duration that is no less than about 100 microseconds.

In some embodiments of the system, the at least one pulse of the plurality of pulses has a pulse energy that is no greater than about 100 mJ.

In some embodiments of the system, the system additionally includes a chiller configured to cool the coolant to a temperature within a range of about −20° C. to about 20° C.

In some embodiments of the system, the optic is further configured to converge the EMR beam at a numerical aperture (NA) of at least about 0.2.

In some embodiments of the system, the system additionally includes an optical tissue clearing medium located between the window assembly and the tissue, wherein the optical tissue clearing medium includes at least one of glycerin, polyethylene glycol, and phosphate-buffered saline.

In some embodiments of the system, the EMR source additionally includes a beam shaper configured to shape the transverse ring-shaped energy profile. In some versions of the system, the beam shaper includes an axicon.

In some embodiments of the system, the controller is configured to control the EMR source to ensure that the window assembly cools the tissue to a predetermined temperature prior to generating the EMR beam.

In some embodiments of the system, the controller is configured to control the EMR source to ensure that the window assembly cools the tissue for a predetermined period prior to generating the EMR beam.

In some embodiments of the system, at least one of the EMR source, the optic, and the beam scanning system is configured to control one or more parameters of the EMR beam, including one or more of an inner diameter of the ring-shaped energy profile, an outer diameter of the ring-shaped energy profile, a thickness of the ring-shaped energy profile, and depth of the focal region within the tissue.

According to some embodiments, a method includes: cooling, using a window assembly contacting an outer surface of the tissue, the tissue; generating, using an EMR source, an EMR beam having a transverse ring-shaped energy profile and a wavelength in a range of about 1200 nm to 12000 nm; converging, using an optic, the EMR beam to a focal region located within a tissue; scanning, using a beam scanning system, the focal region within the tissue; and, controlling, using a controller, the EMR source to generate the EMT beam with a plurality of pulses, wherein at least one pulse of the plurality has a pulse duration that is no less than about 100 microseconds. In some embodiments, the window includes: a first window; a second window separated from the first window: and, a coolant chamber located between the first window and the second window. The coolant chamber is configured to contain coolant including a fluorocarbon-based fluid that is substantially non-absorbent of the EMR beam.

In some embodiments of the method, the at least one pulse of the plurality of pulses has a pulse energy that is no greater than about 100 mJ.

In some embodiments of the method, the method additionally includes cooling, using a chiller, the coolant to a temperature within a range of about −20° C. to about 20° C.

In some embodiments of the method, converging the EMR beam is performed at a numerical aperture (NA) of at least about 0.2.

In some embodiments of the method, the method additionally includes introducing an optical tissue clearing medium between the window assembly and the tissue, wherein the optical tissue clearing medium includes at least one glycerin, polyethylene glycol, and phosphate buffered saline.

In some embodiments of the method, the EMR source additionally includes a beam shaper configured to shape the transverse ring-shaped energy profile. In some versions of the method, the beam shaper includes an axicon.

In some embodiments of the method, the method additionally includes controlling, using the controller, the EMR source in order to ensure that the window assembly cools the tissue to a predetermine temperature prior to generating the EMR beam.

In some embodiments of the method, the method additionally includes controlling, using the controller, the EMR source in order to ensure that the window assembly cools the tissue for a predetermined period prior to generating the EMR beam.

In some embodiments of the method, the method additionally includes controlling at least one parameter of the EMR beam, including one or more of an inner diameter of the ring-shaped energy profile, an outer diameter of the ring-shaped energy profile, a thickness of the ring-shaped energy profile, and a depth of the focal region within the tissue.

According to some embodiments, the system includes: an EMR source configured to generate an EMR beam having a wavelength in a range between about 1400 nm and about 3500 nm; a collimator configured to collimate the EMR beam to a collimated beam width; a beam shaper including a first axicon and a second axicon configured to shape the EMR beam into transverse ring-shaped energy profile, wherein the first axicon and the second axicon are separated by a separation distance along an optical axis, wherein an inner diameter of the ring-shaped energy profile is related to the separation distance and a thickness of the ring-shaped energy profile is related to the collimated beam width; an optic configured to converge the EMR beam at a numerical aperture of at least about 0.2 to a focal region located within a tissue; a beam scanning system configured to scan the focal region within the tissue; a window assembly located down-beam from the optic configured to transmit the EMR beam and cool the tissue when placed in contact with an outer surface of the tissue, wherein the window assembly includes: a first window; a second window separated from the first window; and, a coolant chamber located between the first window and the second window wherein the coolant chamber is configured to contain a coolant including a fluorocarbon-based fluid that is substantially non-absorbent of the EMR beam; a chiller configured to cool the coolant to a temperature within a range of about −20° C. to about 20° C.; a controller configured to control the EMR source in order to ensure that the window assembly cools the tissue to a predetermined temperature or for a predetermined time prior to generating the EMR beam; and, control the EMR source to generate the EMR beam with a plurality of pulses, wherein at least one pulse of the plurality of pulses has a pulse duration that is no less than 100 microseconds; and, wherein the at least one of the EMR source, the optic, and the beam scanning system is configured to control one or more parameters of the EMR beam, including one or more of the inner diameter of the ring-shaped energy profile, an outer diameter of the ring-shaped energy profile, the thickness of the ring-shaped energy profile, and depth of the focal region within the tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the disclosure will be more fully understood from the following detailed description taken in conjunction with the accompanying drawings, in which:

FIG. 4E shows a transverse ring energy profile 0.1 mm before focus, according to some embodiments;

FIG. 4G shows an energy profile of a transverse ring (i.e., donut) energy profile 0.5 mm before focus, according to some embodiments;

FIG. 11A illustrates a front view of an exemplary embodiment of a treatment system;

FIG. 11B illustrates a side view of an exemplary embodiment of a treatment system;

FIGS. 19A-19C illustrate exemplary scanning patterns associated with pre-objective scanning systems in FIGS. 14, 17, and 18;

Figure 1:
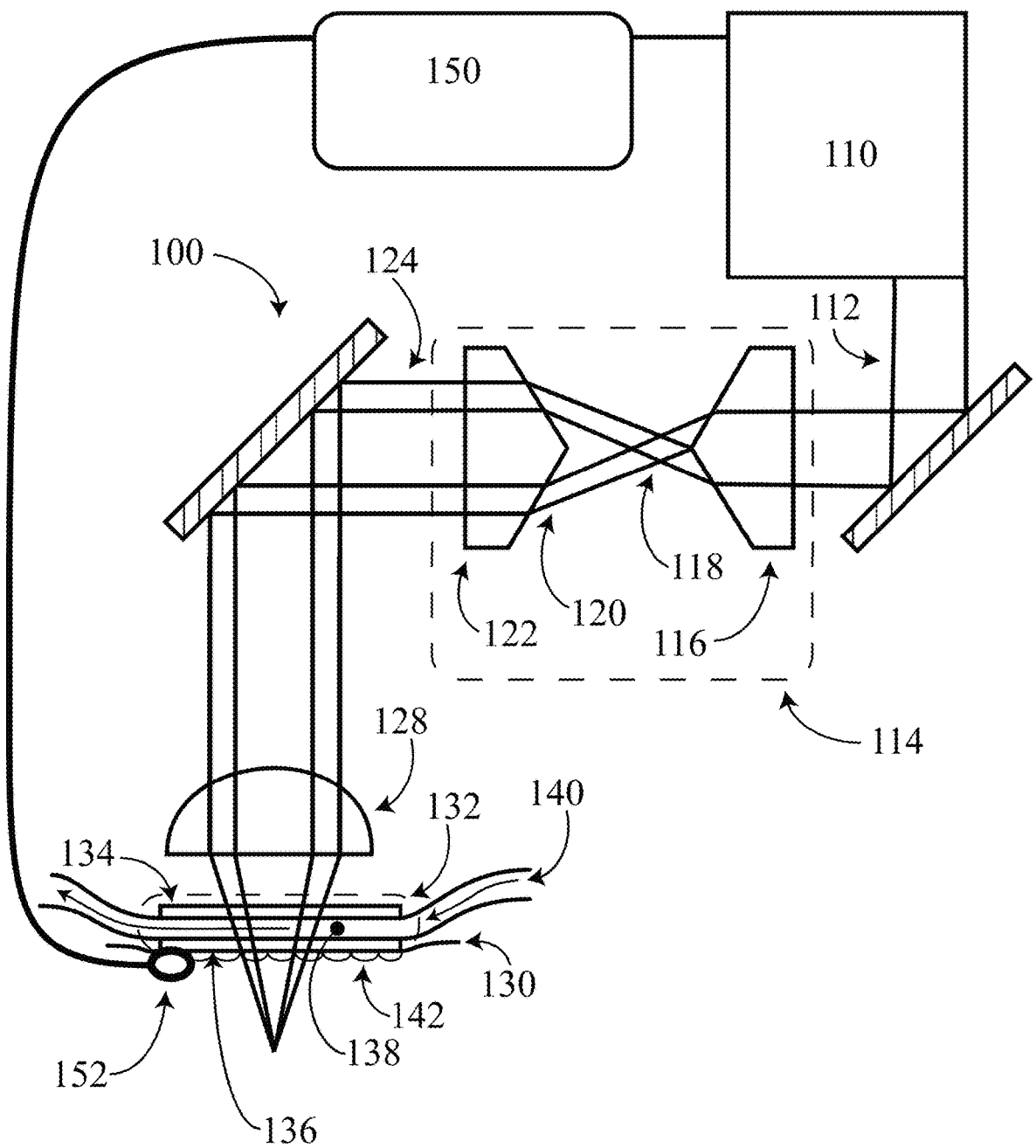
FIG. 1 schematically illustrates an apparatus for electromagnetic radiation (EMR) treatment, according to some embodiments.

It is noted that the drawings are not necessarily to scale. The drawings are intended to depict only typical aspects of the subject matter disclosed herein, and therefore should not be considered as limiting the scope of the disclosure. The systems, devices, and methods specifically described herein and illustrated in the accompanying drawings are non-limiting exemplary embodiments.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Embodiments of the disclosure are discussed in detail below with respect to fractionated treatment including skin rejuvenation and skin resurfacing, for example skin resurfacing for: acne, chickenpox and surgical scars, periorbital and perioral wrinkles, photoageing changes, facial dyschromias, and stretch marks. Additional treatments related to the disclosure include treatment of pigmentary conditions of the skin, such as melasma, and other pigmentary conditions, such as granuloma annulare.

The disclosed embodiments can be employed for treatment of other pigmentary and non-pigmentary conditions and other tissue and non-tissue targets without limit. Examples of pigmentary conditions can include, but are not limited to, post inflammatory hyperpigmentation (PIH), dark skin surrounding eyes, dark eyes, café au lait patches, Becker's nevi, Nevus of Ota, congenital melanocytic nevi, ephelides (freckles) and lentigo. Additional examples of pigmented tissues and structures that can be treated include, but are not limited to, hemosiderin rich structures, pigmented gallstones, tattoo-containing tissues, and lutein, zeaxanthin, rhodopsin, carotenoid, biliverdin, bilirubin and hemoglobin rich structures. Examples of targets for the treatment of non-pigmented structures, tissues and conditions can include, but are not limited to, hair follicles, hair shafts, vascular lesions, infectious conditions, sebaceous glands, acne, and the like.

Methods of treating various skin conditions, such as for cosmetic purposes, can be carried out using the systems described herein. It is understood that, although such methods can be conducted by a physician, non-physicians, such as aestheticians and other suitably trained personnel may use the systems described herein to treat various skin conditions with and without the supervision of a physician.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, high numerical aperture (NA) optical treatment systems are described that can focus electromagnetic radiation (EMR) (e.g., a laser beam) to a treatment region in a tissue. The focused laser beam can deliver optical energy to the treatment region without harming the surrounding tissue. The delivered optical energy can, for example, treat tissue in a treatment region of the dermal layer of the skin, without affecting the surrounding regions (e.g., overlying epidermal layer, other portions of the dermal layer, and the like). In other implementations, the delivered optical energy can cause tattoo removal or alteration, or hemoglobin-related treatment.

Exemplary methods and devices for treating skin conditions with light or optical energy are disclosed in U.S. Patent Application Publication No. 2016/0199132, entitled "Method and Apparatus for Treating Dermal Melasma," and U.S. Provisional Application No. 62/438,818, entitled "Method and Apparatus for Selective Treatment of Dermal Melasma," each of which is hereby incorporated by reference herein in their entirety.

In general, systems and corresponding methods are provided for treatment of dermatological conditions. As discussed in greater detail below, the disclosed systems and methods employ electromagnetic radiation (EMR), such as laser beams, to deliver predetermined amounts of energy to a target tissue. The EMR can be focused to a focal region and the focal region can be translated or rotated in any direction with respect to the target tissue. The predetermined amount of radiation can be configured to thermally disrupt or otherwise damage portions of the tissue. In this manner, the predetermined amount of energy can be delivered to any position within the target tissue for treatment such as to improve the appearance thereof.

Referring now to FIG. 1, a system for radiative treatment 100 is shown. An electromagnetic radiation (EMR) source (e.g., a laser source) 110 generates an EMR beam (e.g., a laser beam) 112 having a wavelength (within a range of about 1000 nm to about 12,000 nm, e.g., about 1550 nm). According to some embodiments, the EMR beam 112 has a transverse ring energy profile (e.g., TEM 01*) natively from the EMR source 110. According to other embodiments, a beam shaper 114 shapes the EMR beam to produce a transverse ring energy profile. FIG. 1 illustrates a beam shaper 114 that employs two axicons. A first axicon 116 having a first wedge angle accepts the EMR beam 112 and produces a Bessel beam 118. As the Bessel beam propagates it forms a diverging ring energy profile. The diverging ring energy profile 120 is collimated by a second axicon 122 into a collimated EMR beam having a transverse ring energy profile 124. According to some embodiments, the second axicon 122 has a second wedge angle that is substantially equal to the first wedge angle of the first axicon 116. The ring energy profile 124 is then directed toward a focus optic 128. Some examples of the focus optic 128 include converging optics (e.g., plano-convex lenses) and axicons. The focus optic 128 converges the EMR beam and directs it toward a tissue 130 (e.g., skin). In some cases, the focus optic converges the EMR beam at a numerical aperture (NA) of at least about 0.2 (e.g., about 0.3 to about 0.5). According to some embodiments, a window assembly 132 is located between the focus optic 128 and the tissue 130. The window assembly 132 is substantially transparent at the wavelength of the EMR beam 124. Exemplary window materials include glass, quartz and sapphire. In some embodiments, the window assembly 132 is cooled and is used to cool the tissue 130 during treatment. Commonly, the window assembly 132 is placed in contact with an outer surface of the tissue during operation of the apparatus 100. According to some embodiments, the window assembly 132 includes two windows, a first window 134 and a second window 136, with a cooling chamber 138 located between the two windows. The cooling chamber is configured to contain a coolant. In some embodiments, a flow of coolant 140 passes through the coolant chamber 138. In some embodiments, the coolant includes one or more of: a dielectric fluid, a fluorocarbon-based fluid, ethylene glycol, propylene glycol, water, and an antifreeze. In most cases, the coolant is selected to be generally (e.g., greater than about 50%) transmissive at the wavelength of the EMR beam 124. For example, an exemplary embodiment includes an EMR beam 124 having a wavelength of 1550 nm and a coolant that includes a fluorocarbon-based fluid (e.g., Flourinert™ from 3M), which is substantially transmissive at 1550 nm. In some embodiments, a medium 142 is placed between a bottom surface of the window assembly 132 and an outer surface of the tissue 130. In some versions, this medium 142 acts to match an index of refraction of the window assembly 132 with the tissue 130. In some other versions, the medium penetrates the tissue. Examples of the medium 142 include: glycerol, Phosphate-buffered saline (PBS), polyethylene glycol (PEG) 400, and other suitable biocompatible materials having and index of refraction approximately equal to skin (e.g., about 1.4). In some embodiments, the system 100 further includes a controller 150 to control the EMR source 110. For example, it is advantageous in some embodiments for the EMR source 110 to be controlled in response to cooling of the tissue, to ensure only cooled tissue is irradiated. In some cases, the controller 150 is configured to control the EMR source to ensure that the window assembly cools the tissue to a determined temperature prior to generating the EMR beam. In some other cases, the controller 150 is configured to control the EMR source to ensure that the window assembly cools for a predetermined period of time prior to generating the EMR beam. According to some embodiments, a temperature sensor 152 (e.g., thermocouple, or thermistor) is used to directly measure tissue temperature. Alternatively, a temperature of a component that is in thermal communication with the tissue is measured with a temperature sensor. For example, temperature of coolant as it outflows the coolant chamber 138 can be used as an indicator of tissue temperature.

In some embodiments, the controller 150, in communication with one or more of the EMR source 110, the beam shaper 114, and the focus optic 128, is further configured to control one or more parameters of the EMR beam. Exemplary EMR beam parameters include an inner diameter of the ring-shaped energy profile, an outer diameter of the ring-shaped energy profile, a thickness of the ring-shaped energy profile, and depth of the focal region within the tissue. According to some embodiments, the EMR beam is scanned throughout the skin tissue to generate numerous locations of thermal disruptions within the tissue, for example to provide a fractionated treatment. Examples of systems and methods related to scanning high NA EMR beams are disclosed in U.S. patent application Ser. No. 16/219,801 entitled "*Electromagnetic Radiation Beam Scanning System and Method*" and International Application No. PCT/US2018/065508, entitled "*Scanning Systems for EMR Based Tissue Treatment,*" both of which are incorporated herein by reference.

Figure 2:
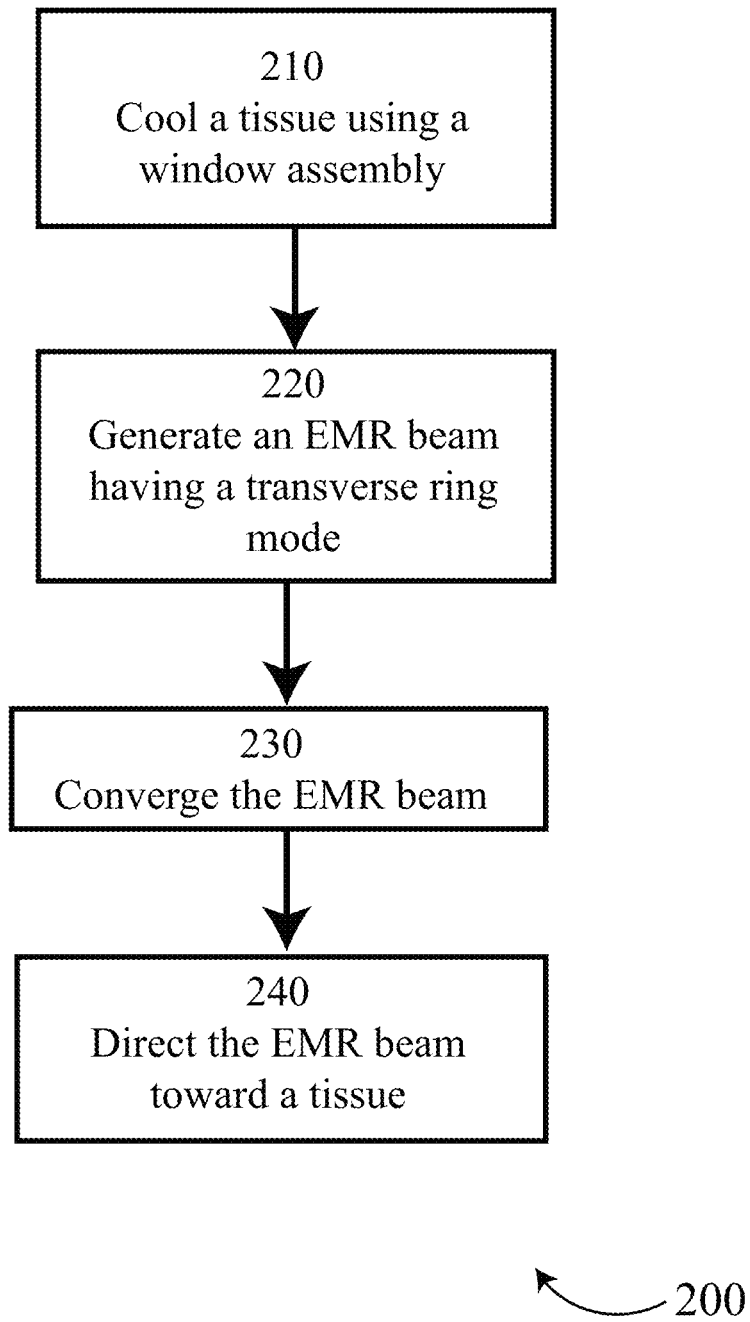
FIG. 2 is a flowchart describing a method for EMR treatment, according to some embodiments.

Referring to FIG. 2, a flowchart 200 represents a method for irradiating a tissue according to some embodiments. First, a tissue is cooled 210 using a window assembly, which is placed in contact with an outer surface of the tissue. According to some embodiments, the window assembly includes two windows, a first window and a second window, with a cooling chamber located between the two windows. The cooling chamber is configured to contain a coolant. In some embodiments, a flow of coolant passes through the coolant chamber. In some embodiments, the tissue is cooled to a predetermined temperature prior to any subsequent steps in the method 200. In some embodiments, the tissue is cooled for a predetermined time prior to any subsequent steps. Cooling the tissue to a predetermined temperature for a predetermined time in some cases can prevent thermal injury to outer layers of tissue (e.g., epidermis) and thereby reduce down-time.

According to some embodiments, a temperature sensor is used to measure temperature that is related to the tissue, for example, a temperature of a component that is in contact (and therefore thermally communicative with) the tissue. Exemplary temperature sensors include thermistors, thermocouples, and infrared temperature sensors. The temperature sensor in some cases senses the tissue temperature directly and in other cases senses a temperature of another material that is related to tissue temperature (e.g., coolant outflowing a contact cooling assembly, which is in contact with the tissue).

Next, an electromagnetic radiation (EMR) beam is generated 220. The EMR beam includes a transverse ring energy profile (e.g., TEM 01* or donut energy profile). The EMR beam is then converged 230 forming a focal region. Typically, the EMR beam is converged using one or more optics (e.g., a converging lens and/or an axicon). In some versions the EMR beam is converged at a numerical aperture (NA) of about 0.2 or greater. Finally, the EMR beam is directed toward a tissue 240, such that the focal region is at least partially located within (i.e., below an outer surface of) the tissue. In some versions, directing the EMR toward a tissue 240 additionally includes scanning the EMR beam, such that the focal region is moved within the tissue. Scanning the EMR is typically done in at least one of three axes (e.g., both axes perpendicular to the optical axis and an axis parallel to the optical axis). For example, the focal region may be scanned in laterally in the tissue as well as in depth within the tissue. In some embodiments of the method 200, an optical tissue clearing medium is introduced to the tissue. For example, in some cases, the optical tissue clearing medium is introduced onto a surface of the tissue between the tissue and the window assembly. In some embodiments, the method 200 additionally includes controlling at least one parameter of the EMR beam. Exemplary parameters of the EMR beam include an inner diameter of the ring-shaped energy profile, an outer diameter of the ring-shaped energy profile, a thickness of the ring-shaped energy profile, and depth of the focal region within the tissue.

Exemplary Embodiment

Figure 3A:
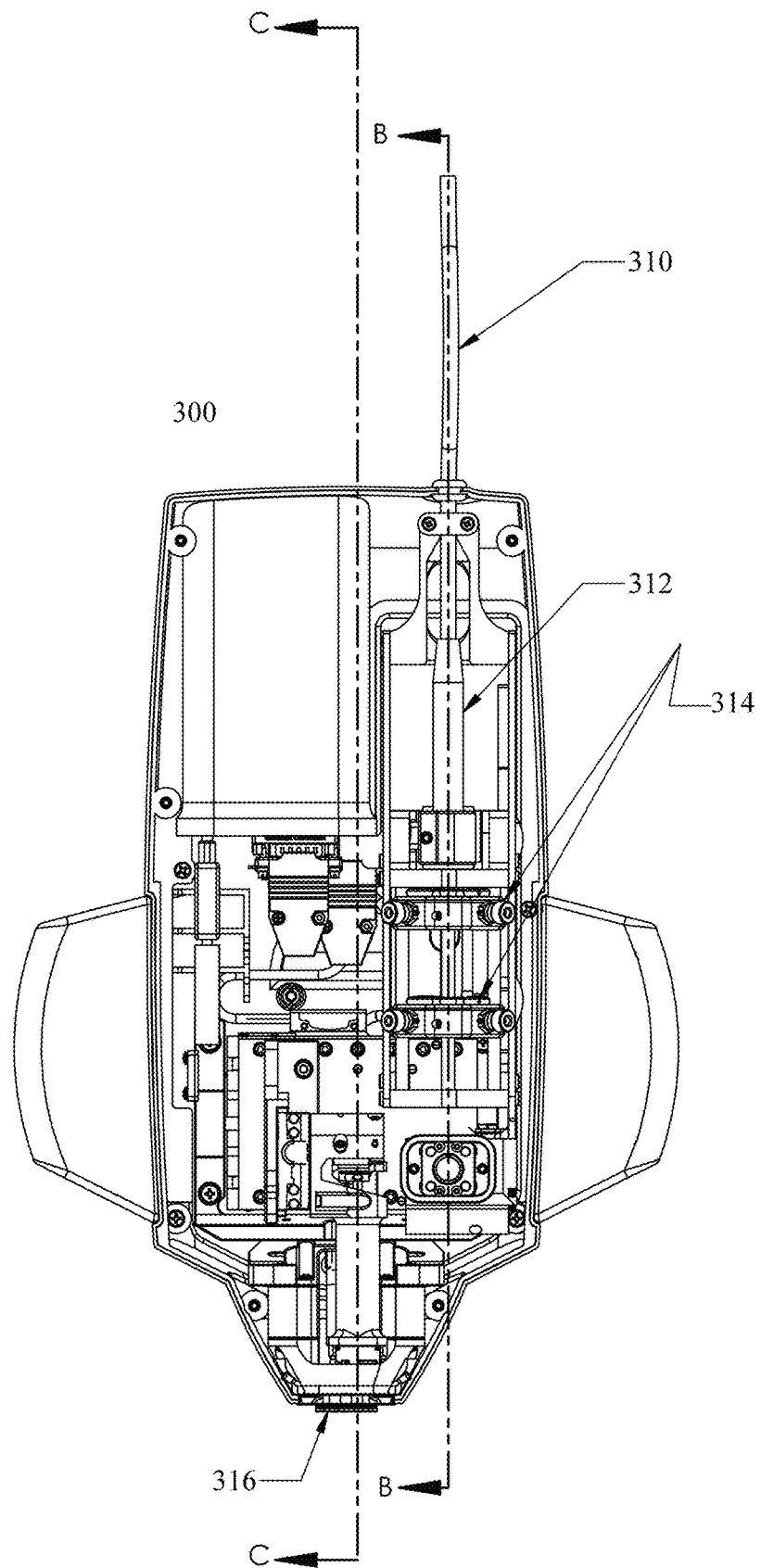
FIG. 3A is a schematic of an exemplary embodiment of an apparatus for EMR treatment, according to some embodiments.

Referring now to FIG. 3A, an example system 300 is shown with a front cover removed. A fiber optic laser source 310 outputs a laser. An exemplary fiber laser source 310 is a CW Er—Yb laser having an average power of 20 W (e.g., IPG Part No. ELR-20-1550-LP from IPG Photonics of Oxford, Massachusetts). The laser is collimated by a collimator 312 to a beam width of approximately 4 mm in diameter. The collimated laser beam is then shaped by a beam shaper 314 into a transverse ring (i.e., donut) energy profile (e.g., TEM 01*). The laser beam is then directed along on optical train, ultimately being focused and directed out of a window assembly 316 at the bottom face of the example system 300.

Figure 3B:
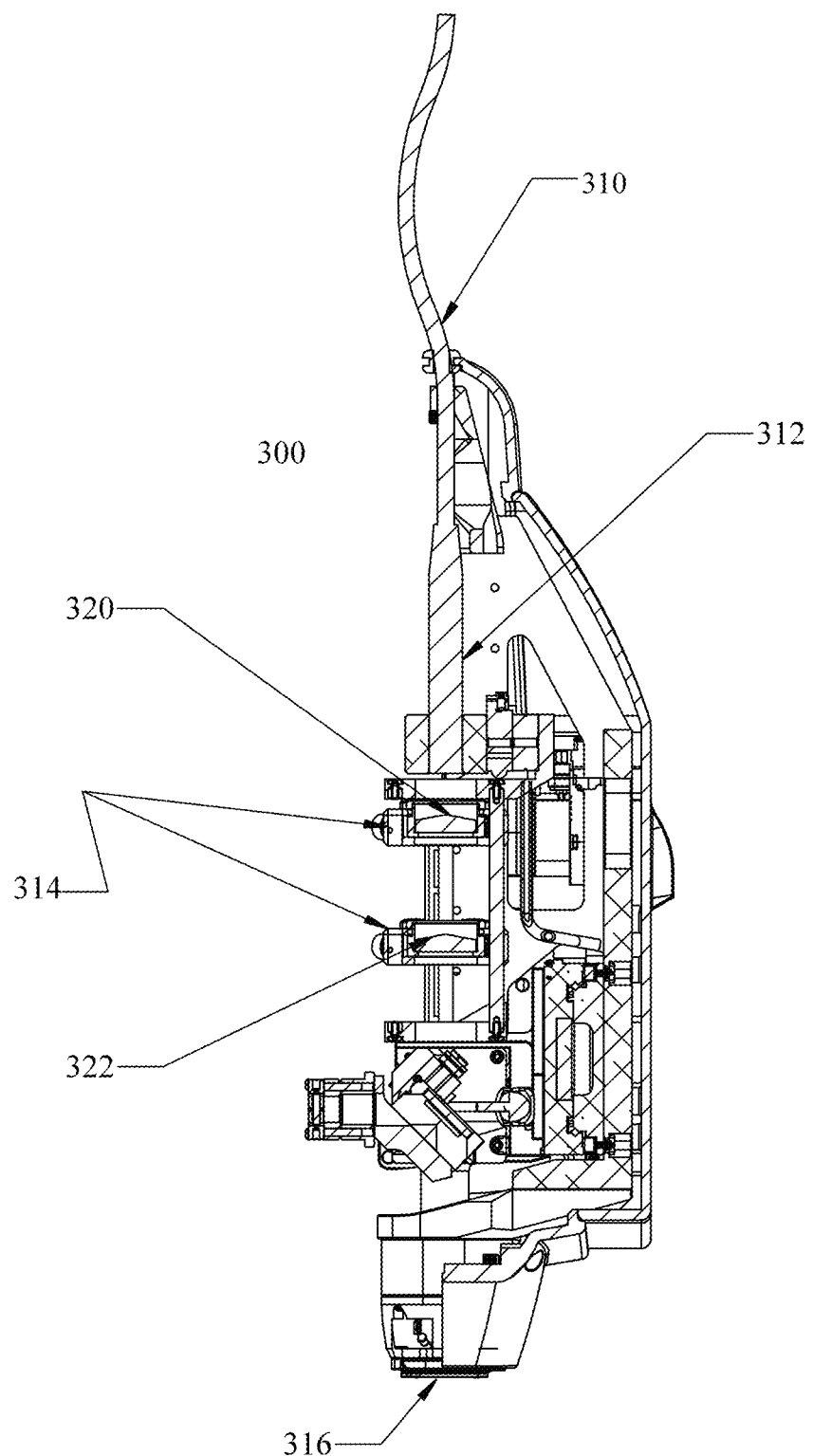
FIG. 3B is a cross-sectional view of the apparatus of FIG. 3A along lines B-B.
Figure 3C:
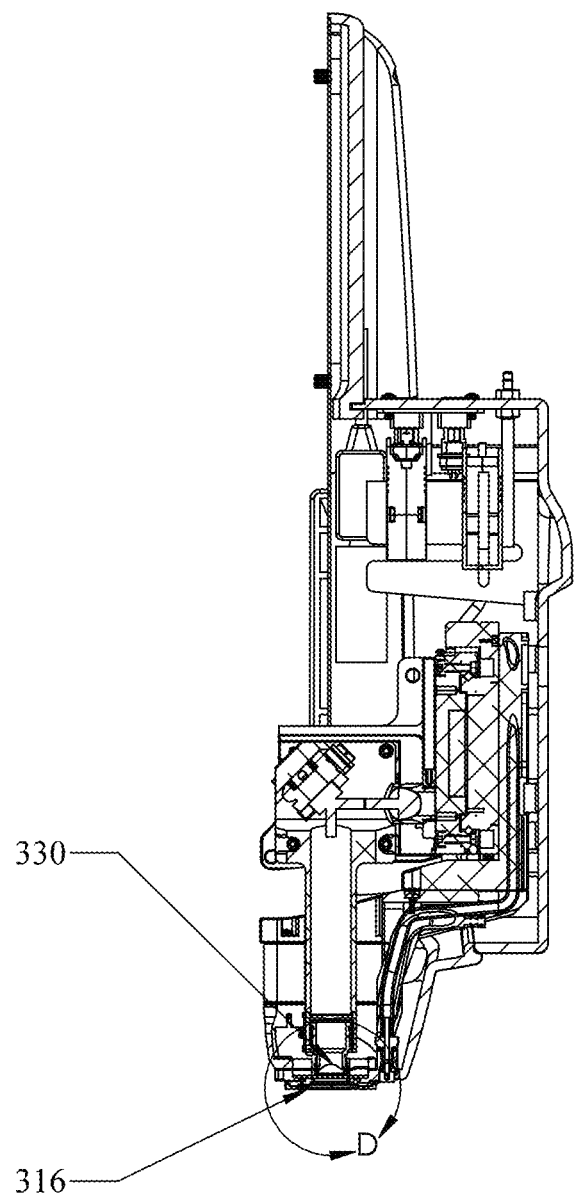
FIG. 3C is a cross-sectional view of the apparatus of FIG. 3A along lines C-C.

FIG. 3B illustrates a cross-sectional view of the example system 300 and the beam shaper 314 taken along section line B-B in FIG. 3A. In FIG. 3B, the beam shaper includes two identical axicons, a first axicon 320 and a second axicon 322. An exemplary axicon is Thorlabs Part No. AX2510-C, which has a physical wedge angle of 10°. A laser beam having a near single order mode (i.e., Gaussian transverse energy profile and $M^2 \leq 1.5$) is shaped by the first axicon 320, first to a Bessel beam then to a diverging transverse ring (i.e., donut) energy profile. The second axicon collimates the diverging transverse ring energy profile into a collimated transverse ring energy profile. The beam shaper is configured such that an inner diameter of the transverse ring energy profile is proportionally related to a separation distance between the first axicon 320 and the second axicon 322. According to the exemplary embodiment, the inner diameter of the transverse ring energy profile is nominally 4 mm. The laser beam now shaped into a transverse ring (i.e., donut) energy profile propagates further along an optical path ultimately exiting the system 300 through the window assembly 316. FIG. 3C illustrates a cross-sectional view of the example system 300 and the window 316 taken along section line C-C in FIG. 3A. A focus optic 330 is located up-beam from the window 316, such that the laser beam converges as it transmits through the window assembly 316. Ultimately, the focus optic 330 brings the laser beam to a focal region outside of the window assembly 316, such that when the window assembly is placed into contact with a tissue the focal region is located within the tissue. An exemplary focus optic is an aspherical lens, Thorlabs Part No. A240-C, having a nominal effective focal length of 8 mm. In some embodiments, a Z-stage 331 houses the focus optic 330 and is configured to adjust the position of the focus optic 330 along an optical axis and thereby affect the depth of the focal region relative the window 316 (i.e., depth of the focal region within the tissue). An exemplary Z-stage 331 is Newscale PN: M3-FS from Newscale Technologies of Victor, New York. In some cases the controller 150 is configured to control the Z-stage in order to affect changes in focal region depth.

Figure 3D:
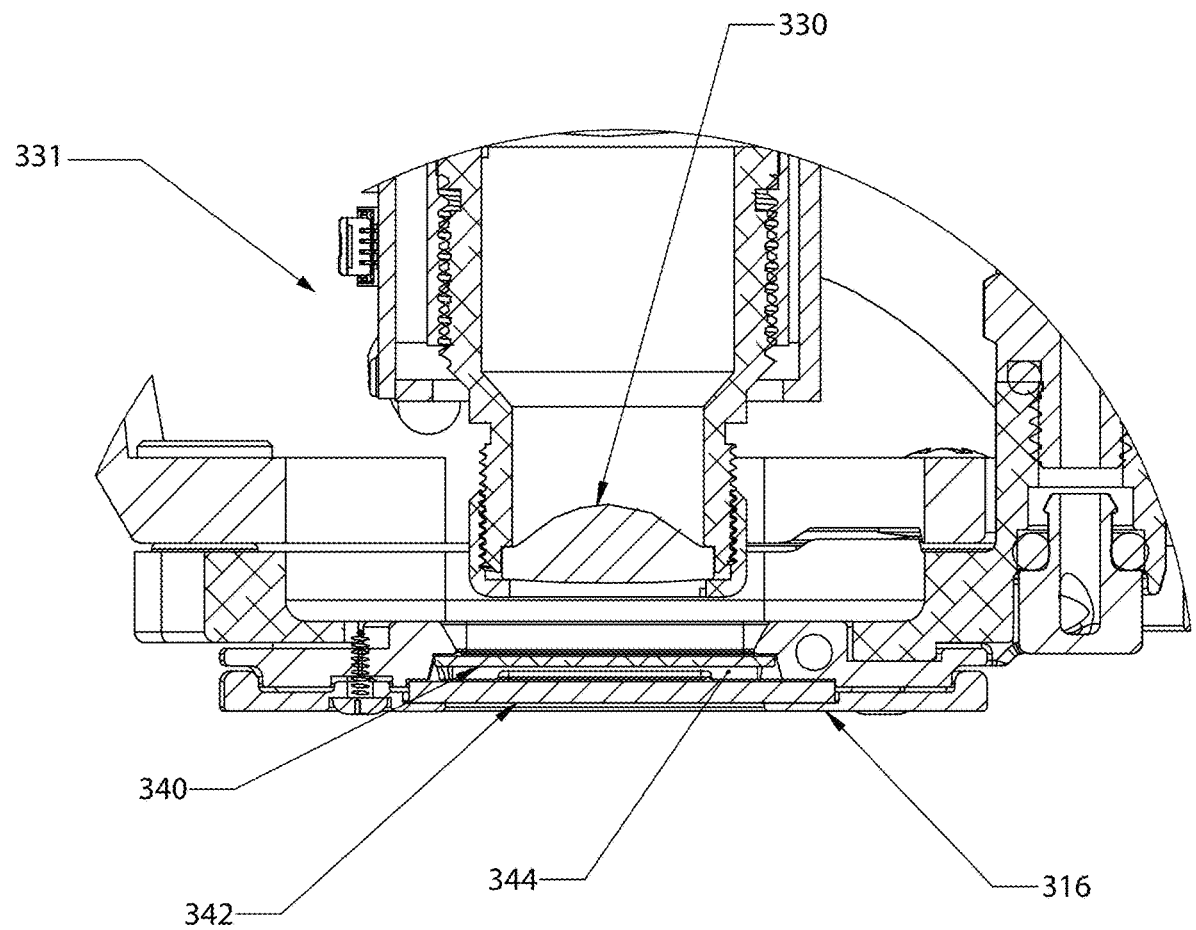
FIG. 3D is a detail view of the apparatus of FIG. 3A at circle D.

FIG. 3D illustrates a detail view of the example system 300 taken from detail circle D in FIG. 3C. The window assembly 316 is shown in greater detail in FIG. 3D. A first window 340 is shown proximal the focus optic 330. A second window 342 is shown separated from the first window 340. A coolant chamber 344 is found between the first window 340 and the second window 342. The coolant chamber 344 is hermetically sealed in order to contain coolant as it flows through the coolant chamber 344. The coolant is warmed through contact with the window assembly 316 and returned to a chiller. The coolant is then cooled by a chiller, for example a thermoelectric chiller (e.g., Part No. UC190 from Solid State Cooling of Wappingers Falls, New York) and recirculated to the window assembly 316. Disclosure related to window assemblies for cooling during irradiation is included in U.S. patent application Ser. No. 16/237,367 to Dresser et al., which is incorporated herein by reference. The exemplary window assembly disclosed in Reference to FIGS. 3A-D is described below in greater detail.

Figure 3E:
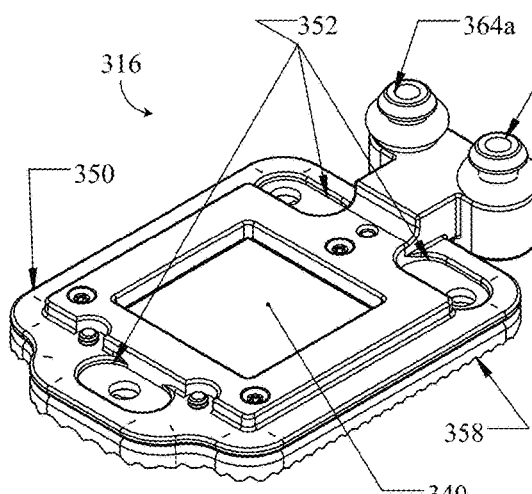
FIG. 3E is a back-facing isometric view of a contact window assembly, according to some embodiments.
Figure 3F:
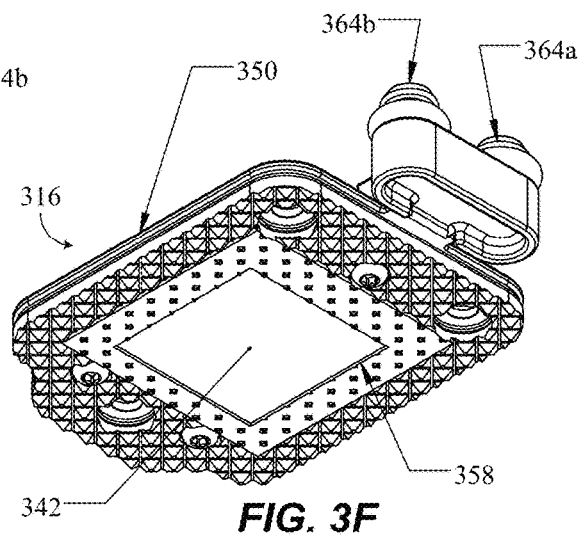
FIG. 3F is a front-facing isometric view of the contact window assembly of FIG. 3E, according to some embodiments.
Figure 3G:
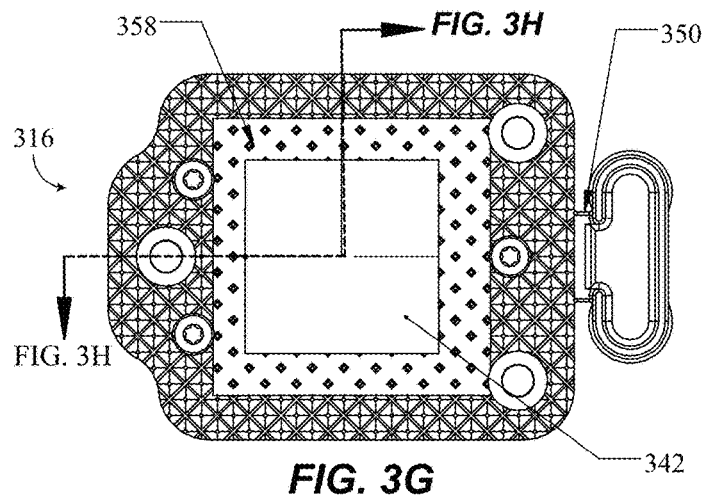
FIG. 3G is a front view of the contact window assembly of FIG. 3E, according to some embodiments.
Figure 3H:
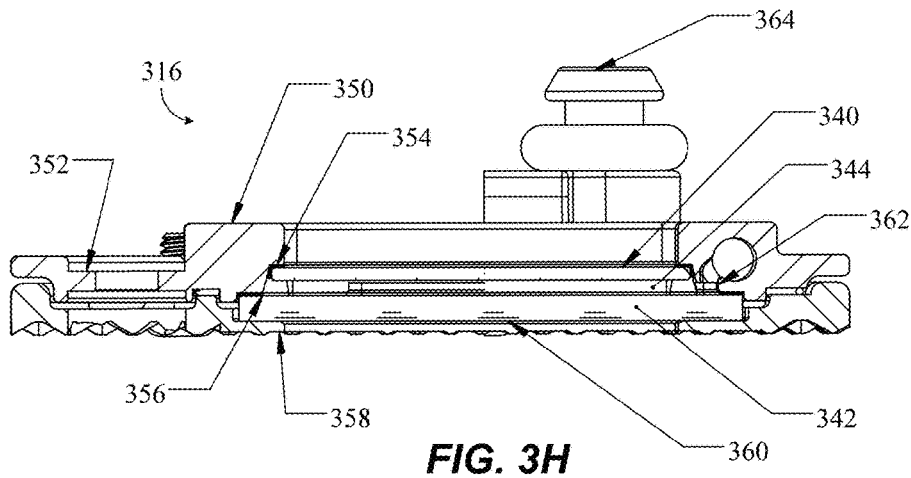
FIG. 3H is a side-facing cross-sectional view of the window assembly of FIG. 3E.

An exemplary window assembly 316 for cooling during irradiation is schematically represented in various views in FIGS. 3E-3H. FIG. 3E illustrates a top isometric view of the assembly 316 (i.e., portion of the cooling element 316 facing the EMR source/facing away from the target tissue). FIG. 3F shows a bottom isometric view of the window assembly 316 (i.e., portion of the window assembly 316 facing the target tissue/facing away from the EMR source). FIG. 3G shows a bottom view of the window assembly 316. FIG. 3H shows a section view of the window assembly 316, along the section lines shown in FIG. 3G. The exemplary window assembly 316 includes a frame 350. Referring to FIGS. 3E and 3G, the frame 350 has three datums 352. The datums 352 correspond to a mount on an energy-based device (e.g., 300), which can generate an irradiation, thereby allowing the window assembly 316 to be removably attached and replaced on the energy based device. According to some embodiments, the datums 352 may approximate one or more geometric forms, for example a plane, a line, and a point. According to some versions, the datums 352 include a part of kinematic mount (e.g., Maxwellian or Kelvin mount). The three datums 352 of the window assembly 316 can be located in a plane. The exemplary window assembly 316 further includes a first window 340 sealed to the frame 350 by a first seal 354 and a second window 342 being sealed to the frame 350 by a second seal 356. According to some embodiments, the first seal 354 and the second seal 356 includes an adhesive. Examples, of adhesives can include light cure adhesives, silicones, and epoxies. According to other embodiments, the first seal 354 and/or the second seal 356 include a weld, a braze, or a solder and the edges of the corresponding first window 340 and/or the second window 342 can be metallized, sputtered, or coated with a material (e.g., metal) allowing for this type of seal. Additionally, the second window 342 is affixed to the frame 350 with one or more fasteners 358. It can be seen in FIGS. 3G and 3H, the fastener 358 of the window assembly 316 includes a clamp plate held in place by 3 machine screws. Additional examples of a fastener can include a screw, a clamp, a snap a retaining ring, a tab, or any combination thereof. Affixing the second window 342 to the frame allows for the distal surface 360 of the second window 342 to be placed firmly in contact with tissue, without introducing additional stress to the second seal 356, which can result in flexure or movement of a distal surface 360 of the second window 342.

A change in distance between the distal surface 360 and an optic focusing an EMR beam affects a working distance of the beam and a location of a resulting focus within a tissue. According to some embodiments, the distal surface 360 of the second window 342 can be located at a predetermined geometry (e.g., orientation, location, etc.) relative the datum 352. For example in some versions, the second window 342 is located parallel to a plane approximated by one or more datums 352 to within a desired tolerance (e.g., 0.5 mrad). Additionally, the second window 342 can be located at a precise distance along the optical axis (e.g., z-axis) within a desired tolerance (e.g., 0.05 mm). Additionally, according to some embodiments, both the first window 340 and the second widow 342 are located parallel and a prescribed distance between them can be within desired tolerances (e.g., 0.5 mrad and 0.05 mm). For various reasons, the distal surface 360 of the second window in some embodiments includes a non-plano shape (e.g., convex or concave). For example, a convex shaped distal surface 360 can be advantageous for compressing a tissue when placed in contact with tissue.

FIG. 3H depicts a chamber 344 within the system 400. The chamber 344 is bounded by the frame 350, the first window 340, and the second window 342. The chamber 344 can be sealed by the first seal 354 and the second seal 356. The chamber 344 is configured to contain a coolant. According to some embodiments, a flow of coolant is supplied to the chamber 344 through one or more ports 362 in fluidic communication with the chamber 344. According to some embodiments, the port 362 can provide for the flow of coolant from a coolant flow source, which is in fluidic communication with the port 362. In some implementations, the coolant flow source can be in fluidic communication with the port 362 by way of one or more fittings 364. FIGS. 3E and 3F illustrate both a coolant supply fitting 364a and a coolant return fitting 364b, for supplying coolant to and returning coolant from the chamber 344.

According to some embodiments, the second window includes a material having a high thermal effusivity (e.g., quartz, sapphire, diamond, etc.). Higher thermal effusivity can allow for more heat to be transferred from the tissue surface to the flow of coolant. Likewise, according to some embodiments, the first window 340 includes a material having a lower thermal effusivity (e.g., a glass or a polymer). Implementations having a first window 340 with a lower thermal effusivity material can transfer less heat through the first window and into the flow of coolant. As a result, condensation can occur more slowly than in versions where the first window 340 includes a high thermal effusivity material. Additionally, in some embodiments the first window has a thickness (e.g., about 1 mm), which is greater than that of the second window (e.g., about 0.5 mm), allowing thermal energy transfer to occur more freely across the second window. According to some versions, a non-condensing gas such as clean dry air, nitrogen, carbon dioxide, or argon can be blown against the first window to further prevent condensation.

Figure 4A:
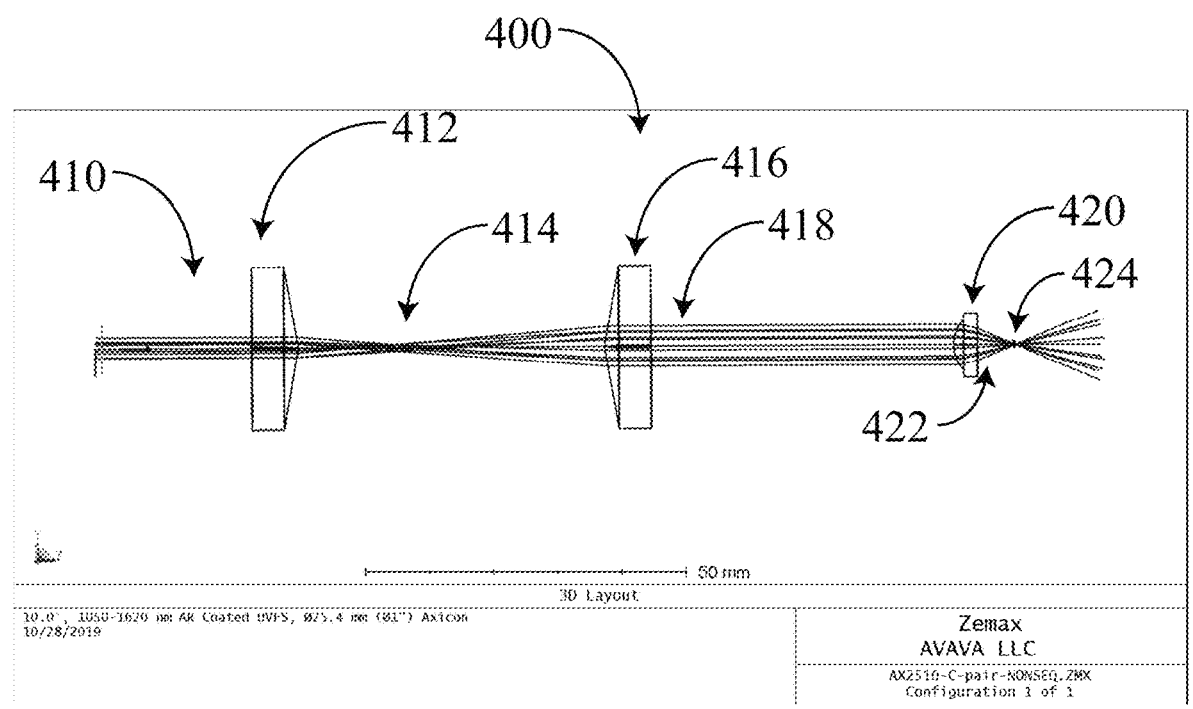
FIG. 4A is a schematic view of an optical path layout for a simulation of a beam shaper, according to some embodiments.

FIG. 4A illustrates a simulated optical layout 400 according to some embodiments. A collimated Gaussian beam 410 propagates incident and on-center to a first axicon 412, which forms a Bessel beam 414. The Bessel beam 414 propagates incident and on-center to a second axicon 416, which forms a collimated transverse ring (i.e., donut) energy profile beam 418. The collimated transverse ring energy profile beam 418 propagates incident and on-center to an aspherical focus optic 420, which forms a converging transverse energy profile 422 that focuses to a focal region 424.

Figure 4B:
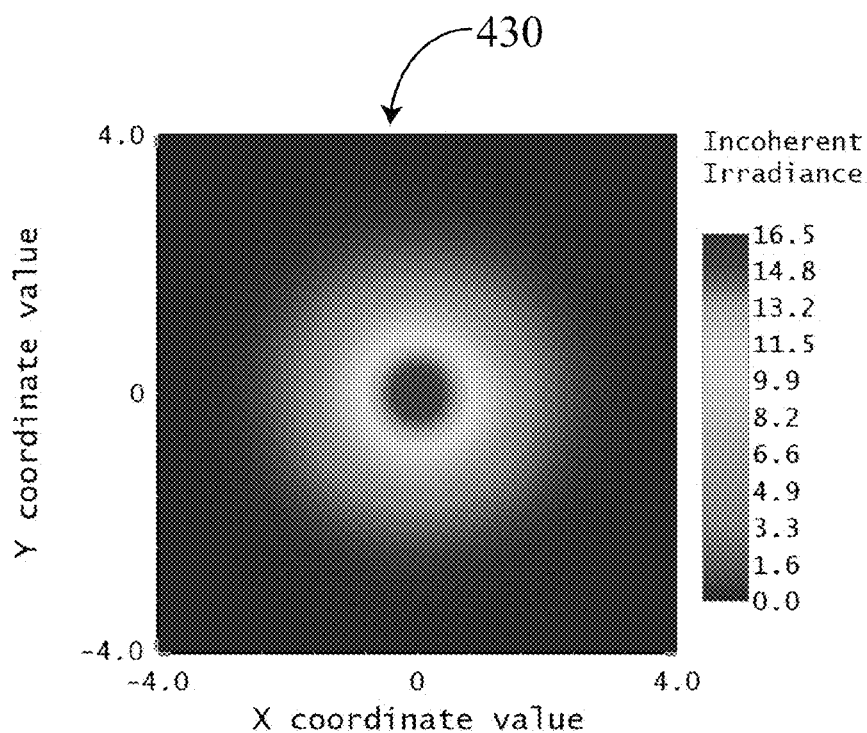
FIG. 4B shows a transverse Gaussian mode, according to some embodiments.
Figure 4C:
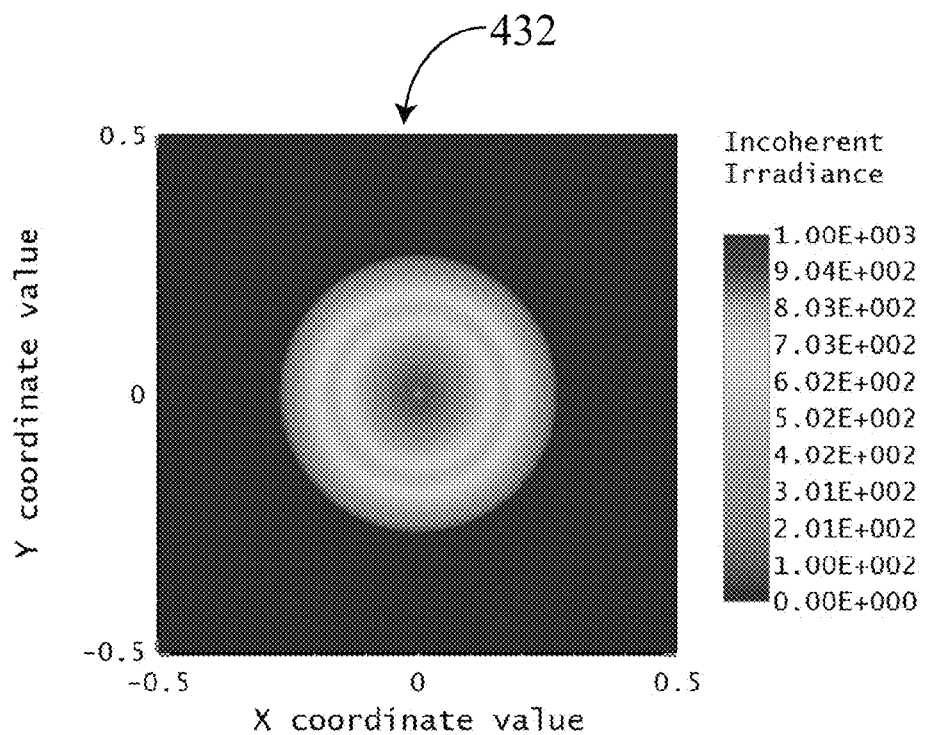
FIG. 4C shows a transverse ring energy profile 0.5 mm before focus, according to some embodiments.
Figure 4D:
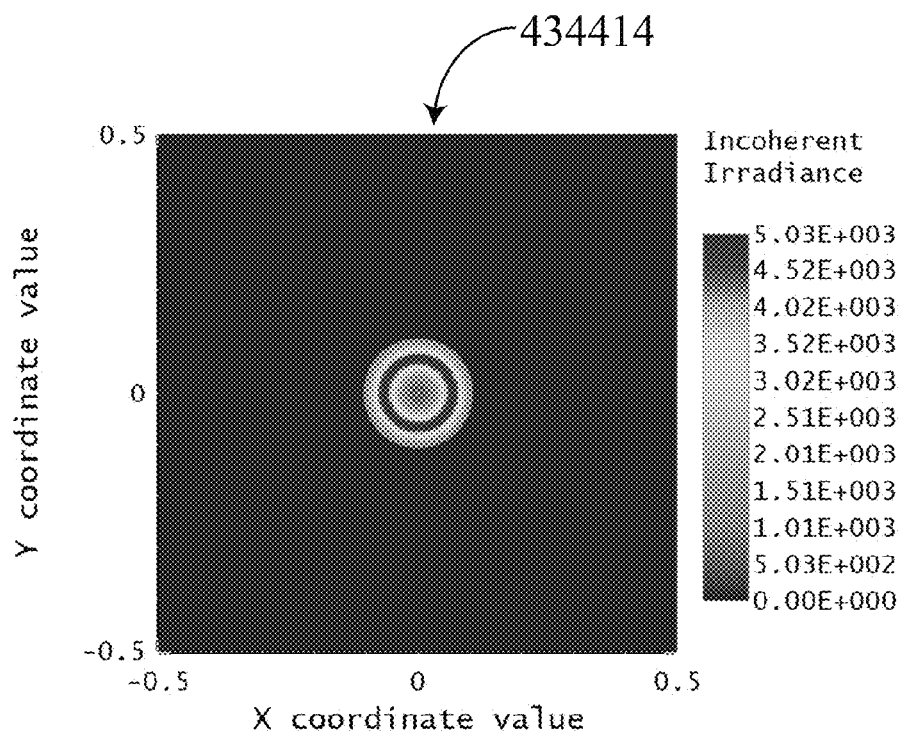
FIG. 4D shows a transverse ring energy profile 0.2 mm before focus, according to some embodiments.
Figure 4F:
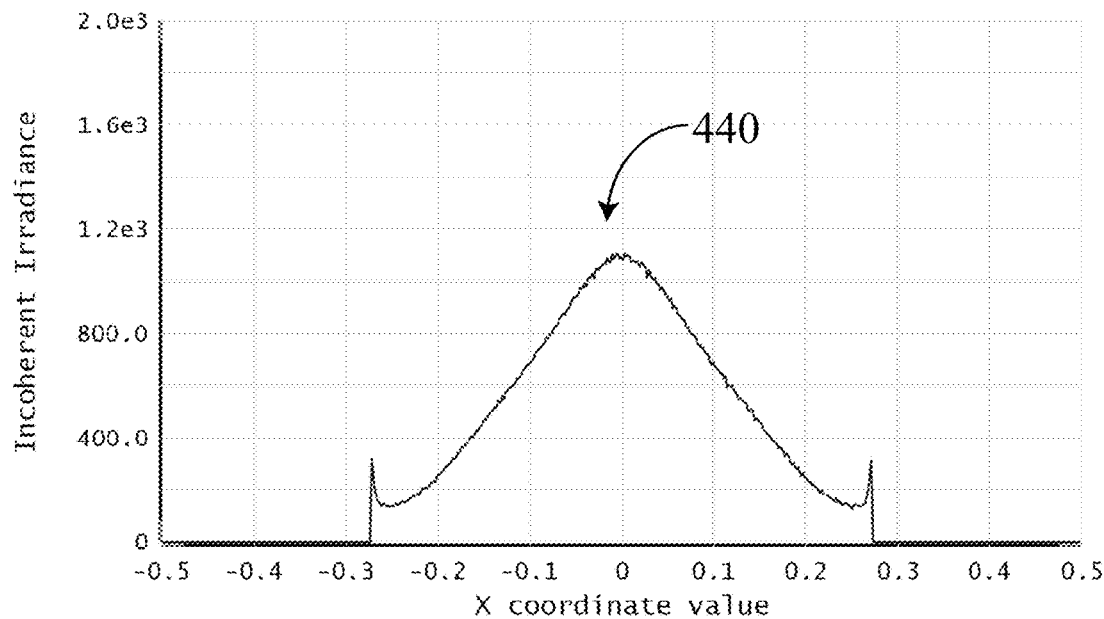
FIG. 4F shows an energy profile of a Gaussian beam 0.5 mm before focus, according to some embodiments.

FIG. 4B illustrates a first simulated Gaussian beam profile 430 of the collimated Gaussian beam 410. FIG. 4C illustrates a first simulated transverse ring (i.e., donut) beam profile 432 of the converging transverse ring energy profile 422 0.5 mm before the focal region 424. FIG. 4D illustrates a second simulated transverse ring beam profile 434 of the converging transverse ring energy profile 422 0.2 mm before the focal region 424. And, FIG. 4E illustrates a third simulated transverse ring beam profile 436 of the converging transverse ring energy profile 422 0.1 mm before the focal region 424. The converging transverse ring energy profile beam 422 has a lower irradiance over the beam profile than a Gaussian mode beam would have under the same conditions. Referring, to FIG. 4F a Gaussian energy profile 440 for a Gaussian beam 0.5 mm from focus is shown. A transverse ring (i.e., donut) energy profile 442 for a transverse ring energy profile beam 0.5 mm from focus is shown in FIG. 4G. Both of the beams characterized in FIG. 4F and FIG. 4G have identical powers (e.g., 1 W). However, a local maximum irradiance for the Gaussian beam is much larger (e.g., 1.29 W/cm$^2$) than the transverse ring energy profile beam (e.g., 0.75 W/cm$^2$). This allows the transverse ring beam to deliver less peak energy density to outer layers of skin (e.g., epidermis), while delivering the same amount of energy to deep layers of skin (e.g., dermis). Control of the reduction in peak local energy density in a transverse ring beam is accomplished by varying a width of an inner diameter of the transverse ring energy profile. Larger inner diameters push more energy to outer portions of the beam and reduce the peak energy density (or power density) within the beam. Additionally, peak local energy density can be reduced in both the Gaussian and transverse ring energy profiles by increasing a numerical aperture of the focus optic 420.

Exemplary Ex Vivo Studies

A number of studies were performed according to some embodiments. The studies were performed using a continuous wave (CW) Er—Yb fiber laser with a maximum average power of 20 W and a wavelength of 1550 nm (IPG laser model: ELR-20-1550LP). Excised human tissue was irradiated using a high numerical aperture (e.g., NA greater than or equal to 0.4) focusing system. Fractional irradiation was accomplished by pulsing the CW fiber laser as the human tissue was scanned relative the focusing system on X-Y translation stages. The human tissue was then sectioned, stained, and reviewed. A nitro blue tetrazolium chloride (NBTC) stain was used to test for viability. Specifically, the NBTC stain acts on proteins within the tissue. Once these proteins are damaged (e.g., thermally denatured) they are no longer stained by the NBTC and appear unstained.

Study No. 1

A first study was conducted to determined pulse energy required for non-ablative thermal disruption of the tissue using a Gaussian beam. Parameters used in study number 1 are shown below:

TABLE 1

| Study No. 1 Parameters | | | | | |
|---|---|---|---|---|---|
| LENS NA 0.5 | | | | | Units |
| Skin | Human Abdominoplasty | | | | |
| Single layer Depth 0.5 mm in skin | tissue4 | tissue3 | tissue2 | tissue1 | |
| Single layer Depth 0.7 mm in skin | tissue5 | tissue6 | tissue7 | tissue8 | |
| Laser average power | 15.5 | 15.5 | 15.5 | 15.5 | W |
| Required Energy per spot | 10 | 20 | 30 | 40 | mJ |
| Pitch of spots | 0.5 | 0.5 | 0.5 | 0.5 | mm |
| Spot size | 0.025 | 0.025 | 0.025 | 0.025 | mm |
| Pulse duration | 0.65 | 1.29 | 1.94 | 2.58 | msec |
| stage speed | 38.75 | 19.38 | 12.92 | 9.69 | mm/sec |
| laser pulse rep rate | 0.01 | 0.03 | 0.04 | 0.05 | sec |
| | 77.5 | 38.75 | 25.83 | 19.38 | Hz |
| Treatment time for 10 × 10 mm$^2$ | 5.2 | 10.3 | 15.5 | 20.6 | Sec |

Figure 5A:
FIG. 5A illustrates a horizontal histology of a tissue sample from study No. 1 discussed herein, according to some embodiments.
Figure 5B:
FIG. 5B illustrates a vertical histology of a tissue sample from study No. 1 discussed herein, according to some embodiments.
Figure 5C:
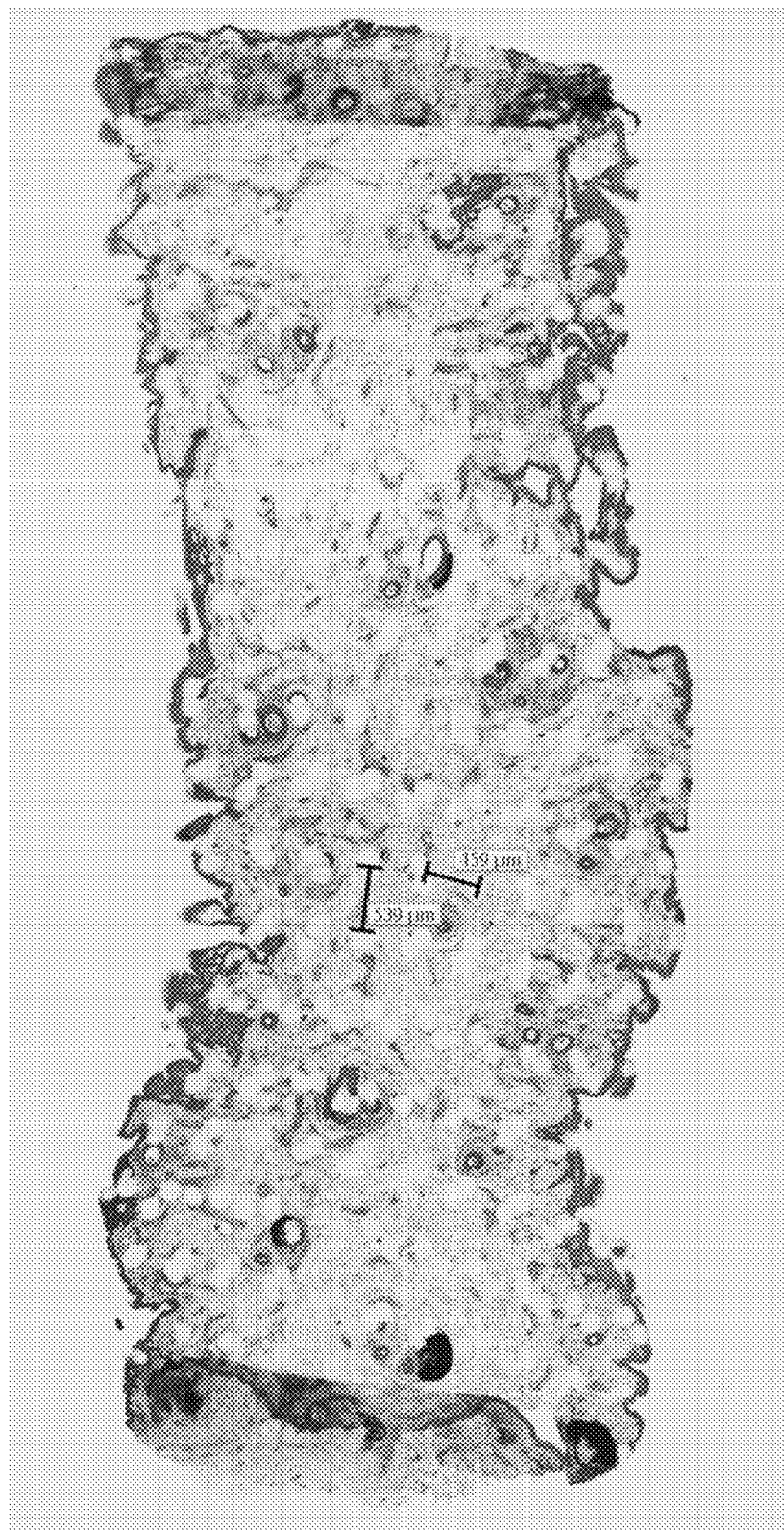
FIG. 5C illustrates a horizontal histology of a tissue sample from study No. 1 discussed herein, according to some embodiments.
Figure 5D:
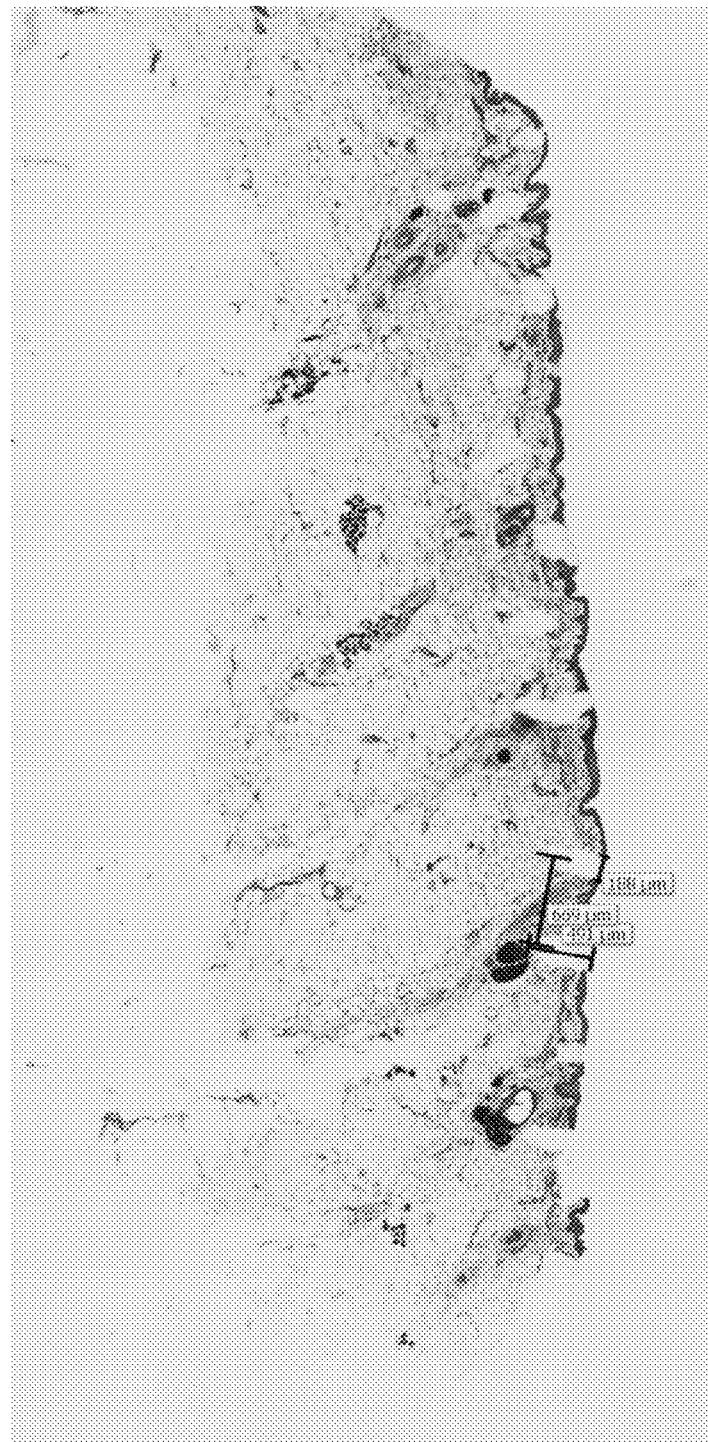
FIG. 5D illustrates a vertical histology of a tissue sample from study No. 1 discussed herein, according to some embodiments.

Some representative results for Study No. 1 are shown in histological slides in FIGS. 5A-D. FIG. 5A illustrates a horizontal cross-section taken after irradiation with pulses having an energy of about 10 mJ. FIG. 5B illustrates a vertical cross-section taken after irradiation with pulses having an energy of about 10 mJ. Very slight thermal denaturing of proteins is evidenced by the NBTC stain. In contrast, irradiation at pulse energies in excess of 10 mJ, for example about 40 mJ, is shown to result in pronounced thermal disruption. FIG. 5C illustrates a horizontal cross-section taken at about 300 micrometers below a surface of the tissue post 40 mJ per pulse irradiation. And, FIG. 5D illustrates a vertical cross-section of tissue after 40 mJ per pulse irradiation. From study No. 1 it was concluded that given this set of parameters 10 mJ per pulse is a threshold pulse energy below which little-to-no thermal disruption occurs.

Study No. 2

Study No. 2 was conducted to determine effects of optical tissue clearing mediums on fractionated non-ablative ex vivo irradiation. Samples of excised human tissue were placed in optical tissue clearing mediums for 4 hours prior to irradiation. The samples were soaked in a petri dish containing the medium epidermis down. Two optical tissue clearing mediums were tested: phosphate-buffered saline (PBS) and glycerol. Parameters used in study number 2 are shown below:

TABLE 2

Study No. 2 Parameters

| LENS 0.5NA Skin | Human Abdominoplasty | | | Units | Optical Tissue Clearing Medium |
|---|---|---|---|---|---|
| Single layer Depth 0.5 mm in skin | tissue 4 | tissue 3 | tissue 2 | tissue 1 | GLYCEROL |
| Single layer Depth 0.7 mm in skin | tissue 8 | tissue 7 | tissue 6 | tissue 5 | PBS |
| Laser power | 15.5 | 15.5 | 15.5 | 15.5 | W |
| Required Energy per spot | 20 | 10 | 7 | 5 | mJ |
| Pitch of spots | 0.5 | 0.5 | 0.5 | 0.5 | Mm |
| Spot size< | 0.025 | 0.025 | 0.025 | 0.025 | Mm |
| pulse duration | 1.290 | 0.645 | 0.452 | 0.323 | msec |
| stage speed | 19.38 | 38.75 | 55.36 | 77.50 | mm/sec |
| laser pulse rep rate | 0.03 38.75 | 0.01 77.50 | 0.01 110.71 | 0.01 155.00 | Sec Hz |
| Treatment time for 10 × 10 mm2 | 10.3 | 5.2 | 3.6 | 2.6 | |

Figure 6A:
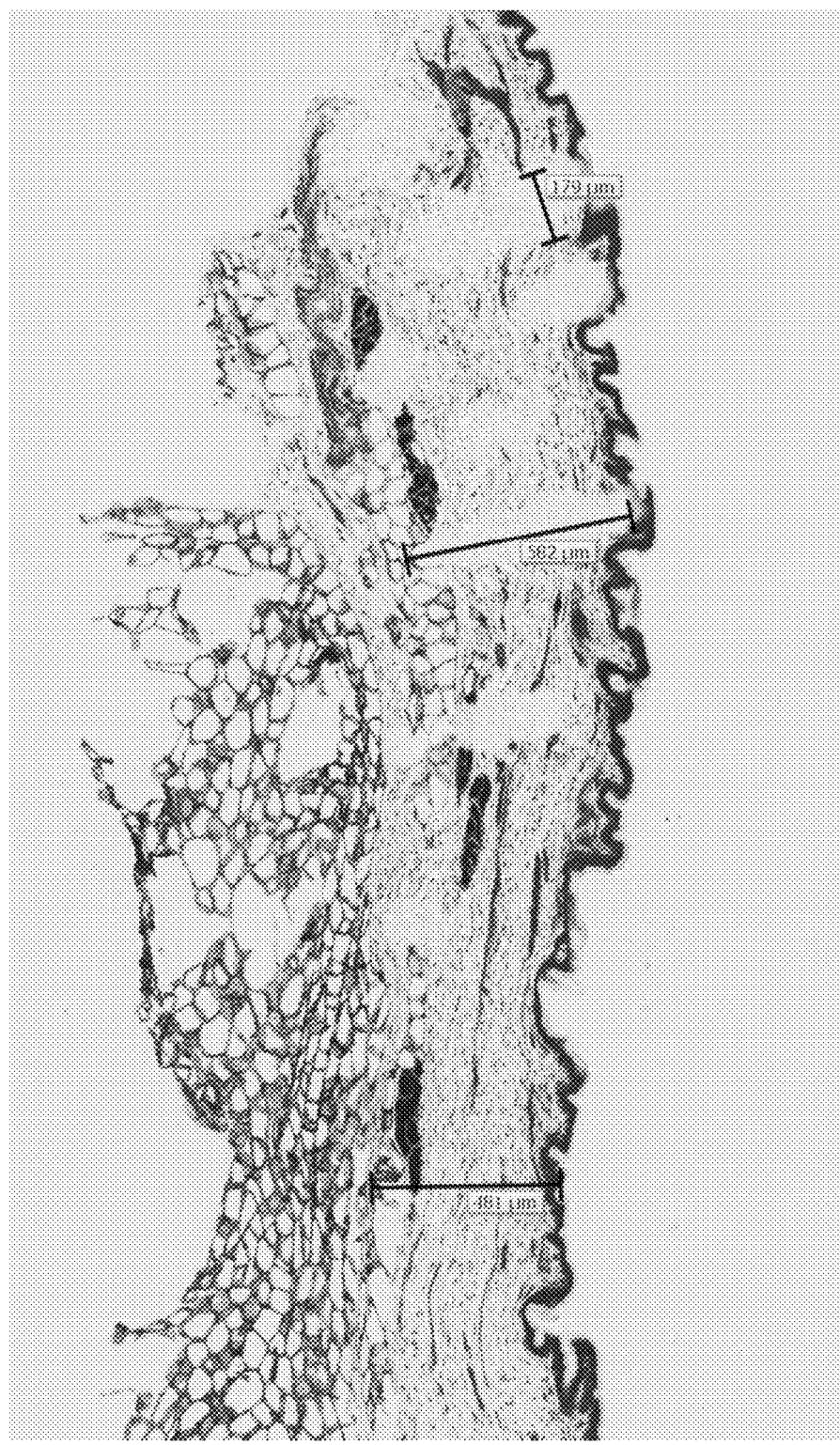
FIG. 6A illustrates a vertical histology of a tissue sample from study No. 2 discussed herein, according to some embodiments.
Figure 6B:
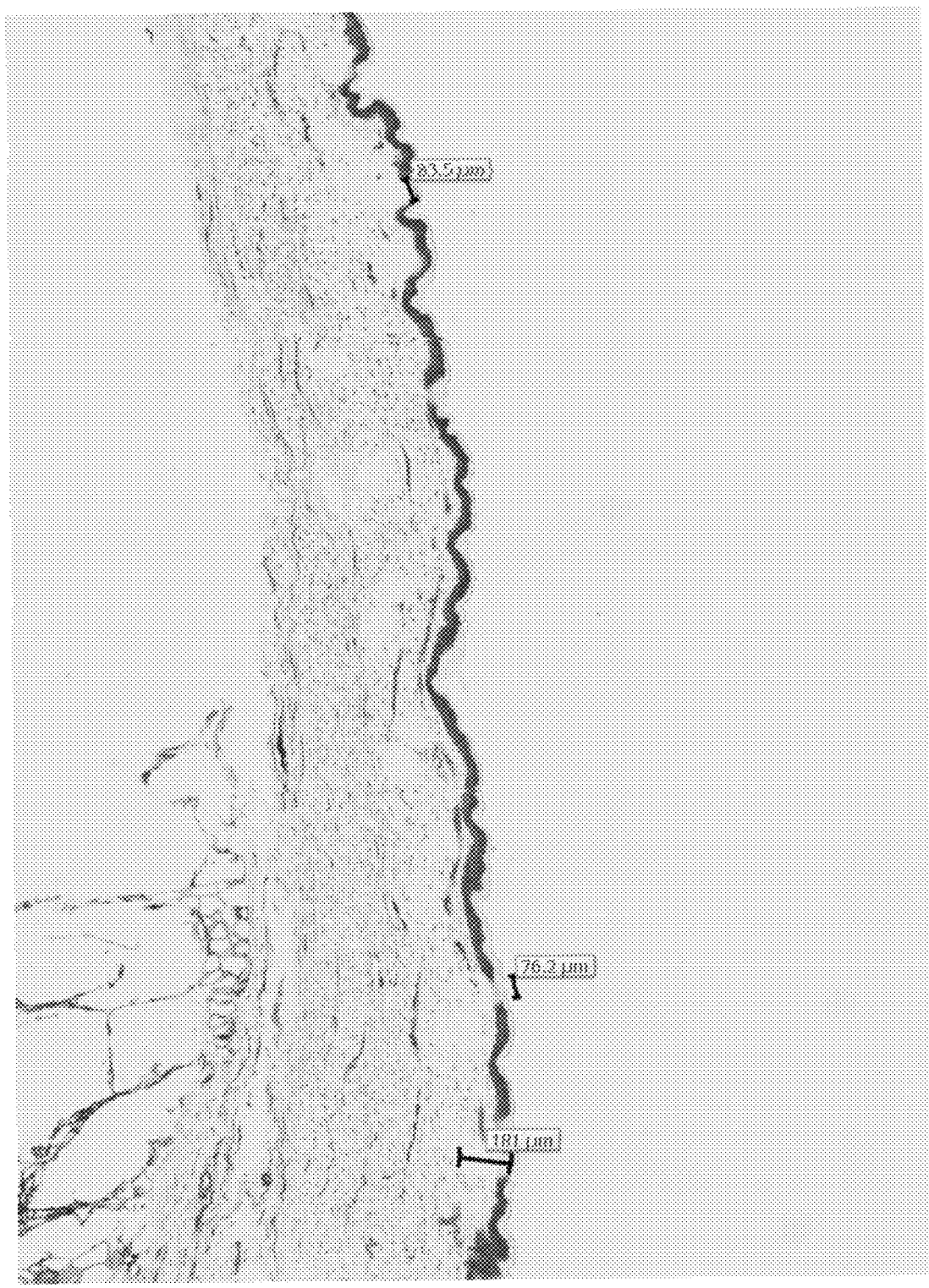
FIG. 6B illustrates a vertical histology of a tissue sample from study No. 2 discussed herein, according to some embodiments.

Thermal disruption was only visible at 20 mJ per pulse in the optical tissue clearing medium soaked tissue samples. No thermal disruption was apparent through NBTC viability staining at the lower testing pulse energies (5 mJ, 7 mJ, and 10 mJ). Some representative results for Study No. 2 are shown in histological slides in FIGS. 6A-B. FIG. 6A illustrates a vertical cross-section taken in a glycerol soaked tissue, irradiated at 20 mJ per pulse. FIG. 6B illustrates a vertical cross-section taken in a PBS soaked tissue, irradiated at 20 mJ per pulse.

Study No. 3

Study No. 2 was conducted to determine effects of a transverse ring (i.e., donut) energy profile on fractionated non-ablative ex vivo irradiation. Samples of excised human tissue were placed in optical tissue clearing mediums for 4 hours prior to irradiation. The samples were soaked in a petri dish containing the medium epidermis down. Two optical tissue clearing mediums were tested: phosphate-buffered saline (PBS) and glycerol. The laser beam was shaped into a transverse ring energy profile as described above and focused into the tissue. Parameters used in study number 2 are shown below:

TABLE 3

Study No. 3 Parameters

| Bessel Beam with two axicons, with 1550 nm coated windows | Abdominoplasty skin | | | | Units | OTC | Beam shape |
|---|---|---|---|---|---|---|---|
| Single layer Depth 0.5 mm in skin | tissue 4 | tissue 3 | tissue 2 | tissue 1 | | PBS | Donut |
| | tissue 7 | tissue 6 | tissue 5 | — | | Glycerol | Donut |
| Laser power | 16.2 | 16.2 | 16.2 | 16.2 | W | | |
| Required Energy per spot | 20 | 10 | 7 | 5 | mJ | | |
| Pitch of spots | 0.5 | 0.5 | 0.5 | 0.5 | Mm | | |
| Spot size< | 0.025 | 0.025 | 0.025 | 0.025 | Mm | | |
| pulse duration | 1.235 | 0.617 | 0.432 | 0.309 | Msec | | |
| stage speed | 20.25 | 40.50 | 57.86 | 81.00 | mm/sec | | |
| laser pulse rep rate | 0.02 40.50 | 0.01 81.00 | 0.01 115.71 | 0.01 162.00 | Sec Hz | | |
| Treatment time for 10 × 10 mm2 | 9.9 | 4.9 | 3.5 | 2.5 | | | |

Figure 7A:
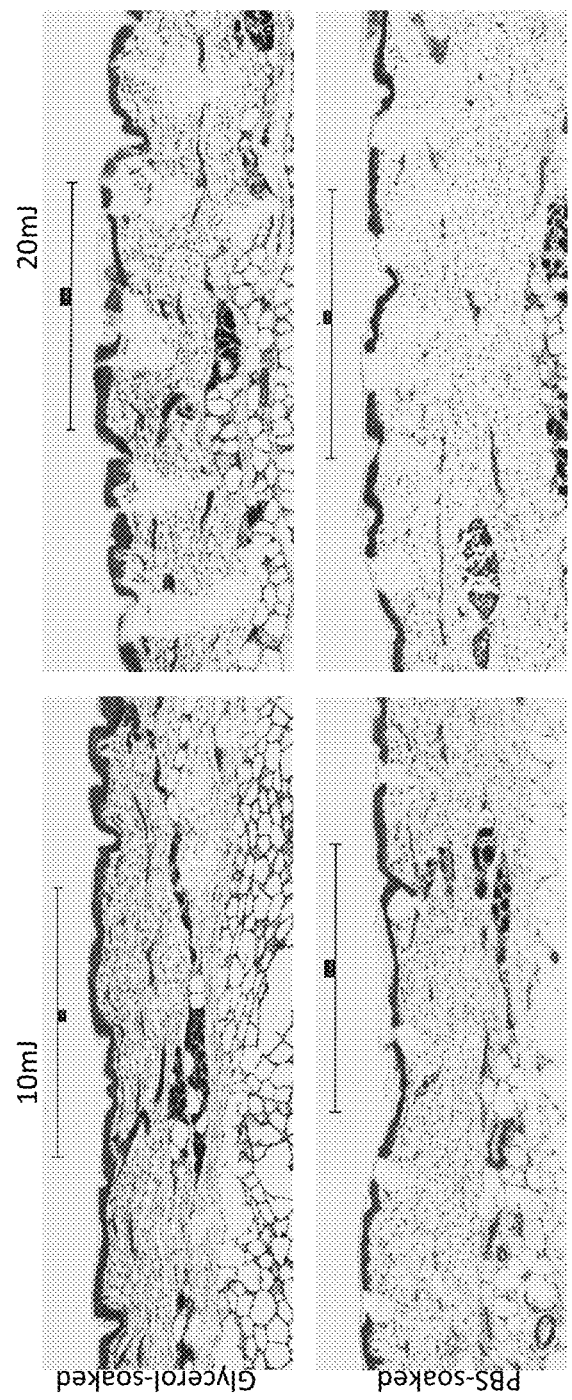
FIG. 7A illustrates multiple vertical histological images of tissue samples from study No. 3 discussed herein, according to some embodiments.
Figure 7B:
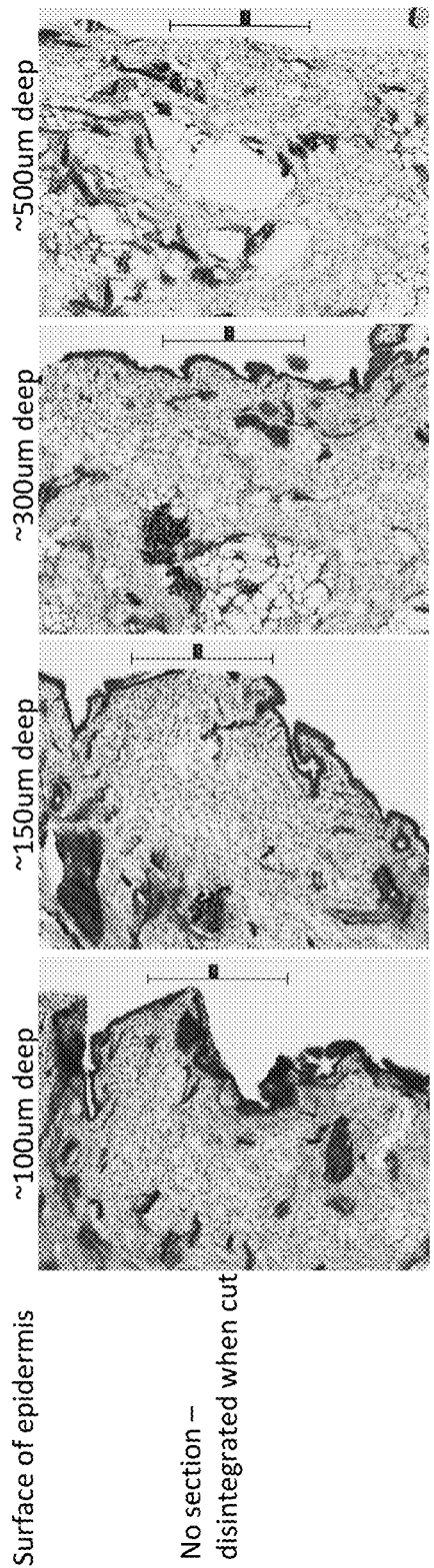
FIG. 7B illustrates multiple horizontal histological images of tissue samples from study No. 3 discussed herein, according to some embodiments.
Figure 7C:
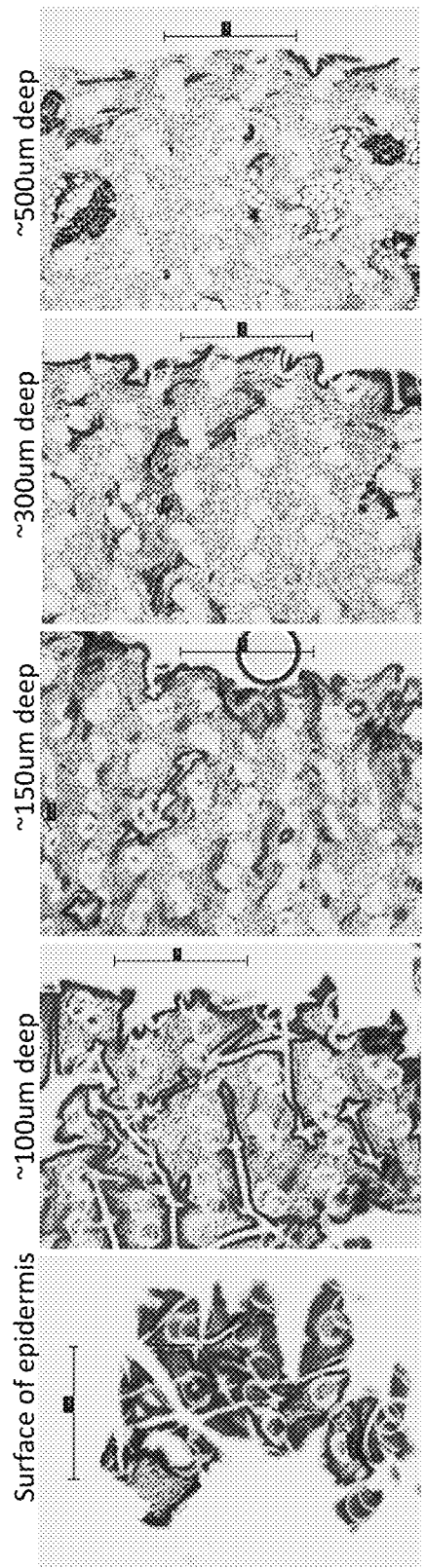
FIG. 7C illustrates multiple horizontal histological images of tissue samples from study No. 3 discussed herein, according to some embodiments.
Figure 7D:
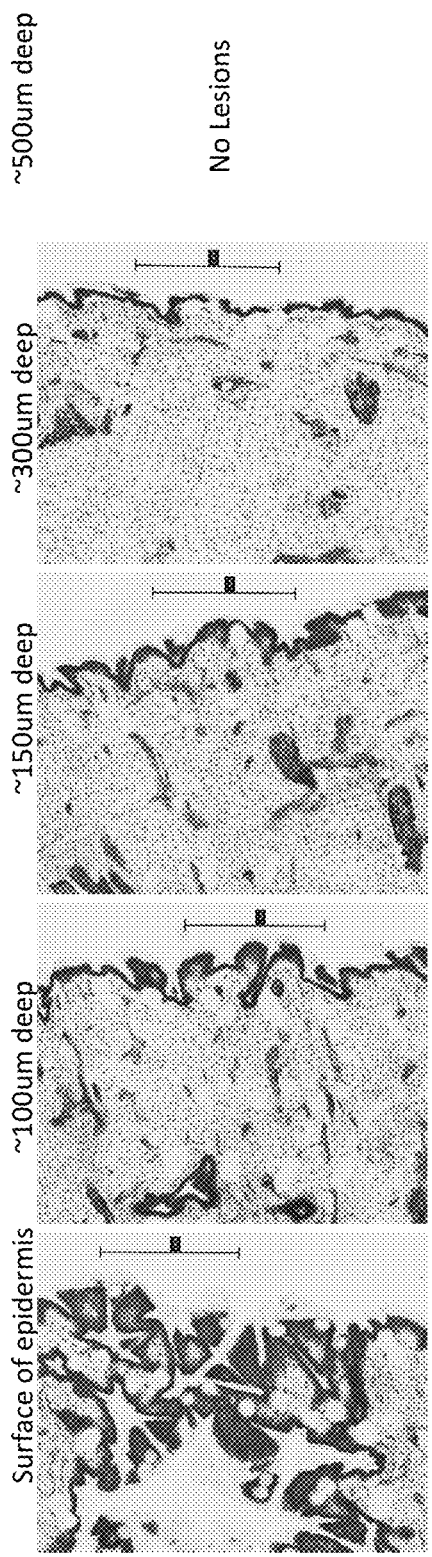
FIG. 7D illustrates multiple horizontal histological images of tissue samples from study No. 3 discussed herein, according to some embodiments.
Figure 7E:
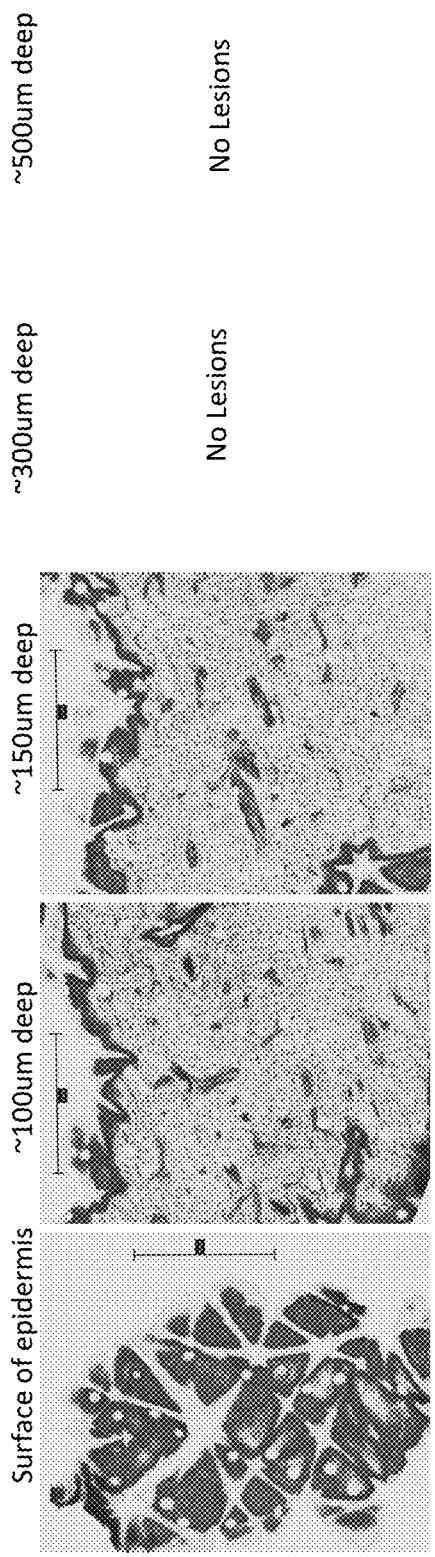
FIG. 7E illustrates multiple horizontal histological images of tissue samples from study No. 3 discussed herein, according to some embodiments.

Histological results from Study No. 3 are described in reference to FIGS. 7A-E. FIG. 7A shows four histological images in a Cartesian layout with glycerol soaked tissue above, PBS soaked tissue below, 10 mJ per pulse energies on a left side, and 20 mJ per pulse energies on a right side. In general, wider and deep thermal disruptions are apparent with 20 mJ than with 10 mJ pulse energies. FIG. 7B illustrates horizontal histological images taken of tissue soaked in glycerol and irradiated with 10 mJ pulse energies. FIG. 7C illustrates horizontal histological images taken of tissue soaked in glycerol and irradiated with 20 mJ pulse energies. FIG. 7D illustrates horizontal histological images taken of tissue soaked in PBS and irradiated with 10 mJ pulse energies. FIG. 7E illustrates horizontal histological images taken of tissue soaked in PBS and irradiated with 20 mJ pulse energies. In horizontal histologies of tissue irradiated with a transverse ring energy profile, ring shaped damage can be seen (e.g., FIG. 7C). The damage that appears as a ring in a horizontal histology is in three-dimensions a thin-walled hollow cone of damage, that comes to a point deep (e.g., 300-1000 micrometers) within the tissue. Within the cone of damage there exists healthy unaffected tissue as evidenced by the rings of damage in the horizontal cross-sections (e.g., FIG. 7C) and the 'Y' shaped damage in the vertical cross-sections (e.g., FIG. 7A). A benefit of this irradiation pattern is that less epidermis is damaged than with current fractionated irradiation techniques; and, that the epidermis that is damaged is damaged in a small narrow width (e.g., 1-100 micrometers) that is surrounded by healthy (i.e., unaffected) tissue.

Parameter Selection

Parameters relevant to practice of embodiments of the present disclosure are outlined in a table below:

TABLE 4

Exemplary Parameters and Ranges

| | Minimum | Maximum | Nominal |
|---|---|---|---|
| EMR Wavelength (nm) | 200 | 20000 | 1550 |
| Numerical Aperture (—) | 0.01 | 1 | 0.5 |
| Focal Region Width (micrometers, μm) | 0.05 | 5000 | 4 |
| Focal Region Length (mm) | 0.005 | 500 | 0.5 |
| Focal Region Depth Below Tissue Surface (mm) | 0 | 10 | 0.3 |
| Pulse Energy (mJ) | 0.1 | 300 | 30 |
| Pulse Duration (nS) | 1 | 1,000,000,000 | 5,000,000 |
| Average Power (W) | 0.01 | 100 | 10 |
| Peak Power (W) | 1 | 1,000,000 | 20 |
| Precool Time (S) | 0.1 | 200 | 10 |
| Precool Temperature (° C.) | −200 (for cryogen cooling) | 10 | 2 |
| Transverse ring (i.e., donut) energy profile, inner diameter (mm) | 0.05 | 50 | 4 |
| Transverse ring (i.e., donut) energy profile, annular width (mm) | 0.05 | 50 | 2 |
| Optical Tissue Clearing Constituents | Glycol, Phosphate-buffered Saline (PBS), Polyethylene Glycol (PEG) 400. | | |
| Coolant Constituents | Water, alcohol, propylene glycol, fluorocarbon-based fluids, and anti-freeze | | |
| Scanning System | Translation Stage(s), galvanometers | | |

Figure 8:
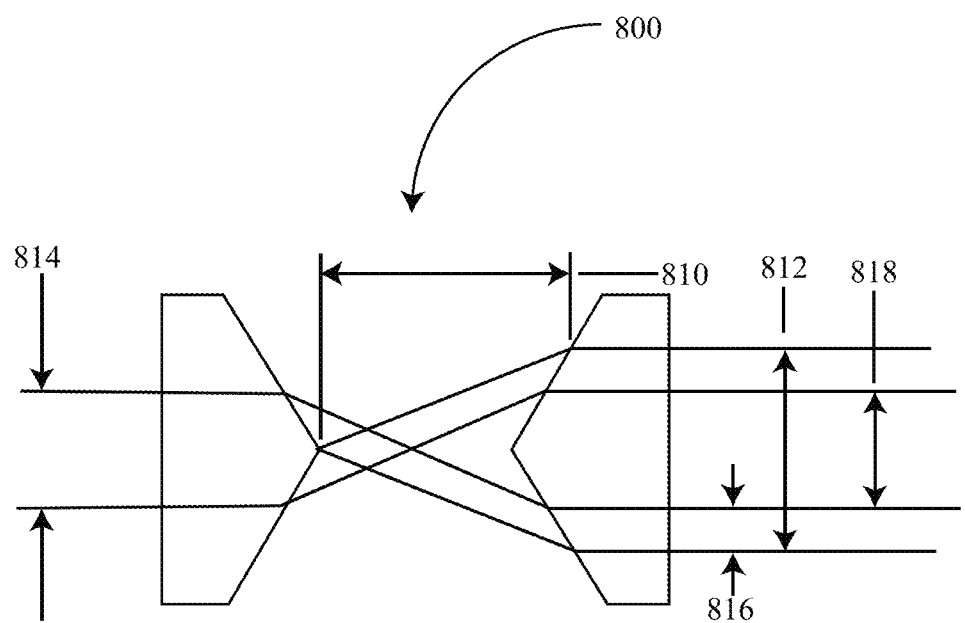
FIG. 8 schematically illustrates an optical scheme for beam shaping, according to some embodiments FIG. 9A schematically illustrates an optical scheme for fractionated treatment, according to some embodiments.

In some embodiments, aspects of the ring-shaped energy profile are controllable. FIG. 8A shows a pair of axicons 800 configured to generate a ring-shaped energy profile. A relationship between separation (S) 810 of the two axicons 800 and major diameter 812 of the resultant ring-shaped beam can be expressed:

$$S = \frac{D_{Major}}{2 * \tan((n-1) * \alpha)}$$

Wherein, n is index of refraction of the first and second axicon and α is a wedge angle of the first and second axicon 800.

As described above, a collimated beam diameter 814, as it enters the axicon pair 800, determines the ring-shaped energy profile width 816. Therefore, in some embodiments, the width of the ring-shaped energy profile 816 is controlled by varying the collimated beam diameter 814. For example, in some cases a beam expander (e.g., Gallian beam expander or Keplerian beam expander) is used to expand (or reduce) the collimated beam diameter 814, before it reaches the axicon pair 800. Minor (i.e., inner) diameter 818 can be expressed in terms of a major (i.e., outer) diameter 812 of the ring energy profile. Specifically, minor diameter 818 is equal to the major diameter 812 less the diameter of the collimated beam 814, or:

$$\varnothing_{minor} = \varnothing_{Major} - \varnothing_{beam}$$

where, $\varnothing_{minor}$ is the minor diameter 818; $\varnothing_{Major}$ is the major diameter 812; and, $\varnothing_{beam}$ is the beam diameter 814. According to some embodiments, one or more parameters related to the ring-shaped energy profile is controlled by a controller, which manipulates the above described parameters (e.g., axicon pair 800 separation distance 810 and/or beam expander rate). For example, in some cases the separation distance 810 between the axicon pair 800 may be electronically manipulated by use of a motorized stage (e.g., Thorlabs PN: PT1-Z8). Likewise, in some cases (e.g., a Gallian beam expander) an optical path distance between two optics controls a beam expansion (or beam reduction) rate of a beam expander. In this case, a motorized stage may also be used to control the width of the beam 814 as it enters the axicon pair 800.

Small diameter fractional treatments result in smaller injury and faster healing. For example, it has been found that fractional damage greater than a certain width (e.g., about 0.15 mm, 0.25 mm, or 0.5 mm) can cause scarring in some individuals. Small fractional damage widths even below what is now commercially achievable will further minimize down-time up to a threshold minimum fractional damage width size. Specifically, beam sizes that are smaller than a single cell (e.g., about 20 micrometers) result in practically the smallest possible fractionated damage. As described above, in some cases the above described exemplary optical systems achieve thermal injury to tissue which is on this scale. In additional exemplary embodiments, small fractionated injury to this tissue is achieved through another exemplary optical system.

One skilled in the art will appreciate further features and advantages based on the above-described embodiments. Accordingly, the disclosed embodiments are not to be limited by what has been particularly shown and described, except as indicated by the appended claims. All publications and references cited herein are expressly incorporated herein by reference in their entirety.

Additional Embodiments

Figure 9A:
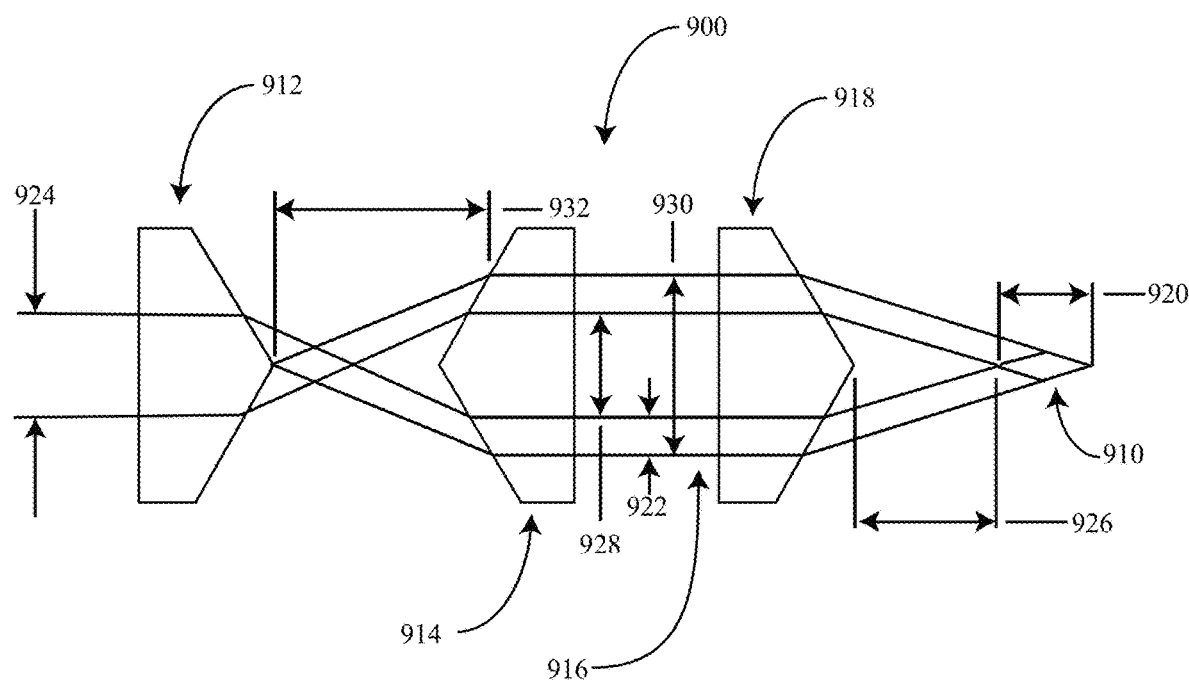
FIG. 9B schematically illustrates an optical scheme for fractionated treatment, according to some embodiments; and, FIG. 10 illustrates an exemplary embodiment of a treatment system.
Figure 9B:
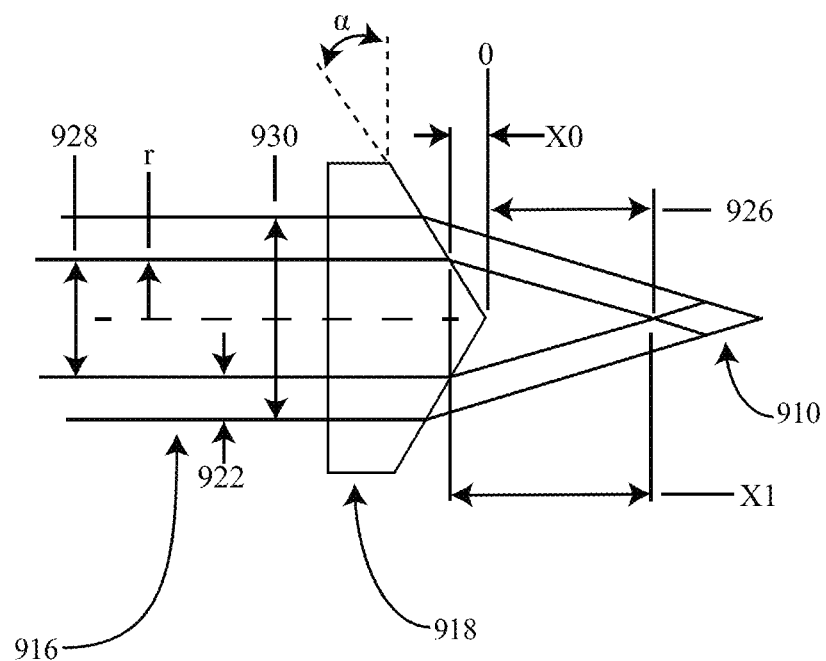

An additional embodiment for affecting fractionated damage at a tens of micrometer scale is described in reference to FIGS. 9A-B. Referring to FIG. 9A, an optical scheme 900 is displayed that produces a Bessel beam focal region 910. Bessel beam focal regions, unlike normal diffraction-limited focal regions, have a focal width and a focal region length that can be decoupled from one another. Normally, a focal region length (i.e., a depth of field) is proportionally related to the square of the focal region radius (e.g., Rayleigh range). Decoupling focal region length from focal region width allows for formation of very long (e.g., greater than 0.5 mm long) focal regions, which are also very narrow (e.g., less than about 0.1 mm wide).

FIG. 9A schematically illustrates an optical path that can be used to generate a long narrow beam. Three axicons are used in this configuration. A first axicon 912 and a second axicon 914 are used to shape the beam into a collimated annular beam 916 and a third axicon 918 is used to focus the beam to a Bessel beam focal region 910.

According to some exemplary embodiments, a width of damage for a fractional treatment is related to a width of a first lobe of the Bessel beam focal region 910. The half width, $\omega_0$, of the first lobe of a Bessel beam focal region 910 is a function of the wavelength, $\lambda$, the wedge angle of the axicon, $\alpha$, and the index of refraction of the axicon, n:

$$\omega_o = \frac{2.4048}{\left(\frac{2\pi}{\lambda}\right) * \mathrm{Sin}((n-1)*\alpha)}$$

Therefore, according to some embodiments, selection of this optical parameter is achieved through selection of an axicon wedge angle for the third axicon 918. A table below illustrates some exemplary first lobe diameter for a 1550 nm beam based upon axicon wedge angle.

TABLE 5

Wedge Angle to First Lobe Diameter (wavelength = 1550 nm)

| Wedge Angle (deg) | First Lobe Diam. (um) |
|---|---|
| 0.5 | 296 |
| 1 | 148 |
| 2 | 74 |
| 5 | 30 |
| 10 | 15 |
| 20 | 7 |
| 30 | 5 |

A length of damage by a fractionated treatment is related to a length of the Bessel beam focal region 910. The length of a Bessel beam (e.g., depth of field [DOF]) 920 formed by an axicon is a function of a width of the beam at the axicon. When an annular beam is used the focal region length is a function of a width of an annulus 922. The width of the annulus is in turn a function of (e.g., half of) a width of the collimated beam, 924, which is shaped to form the annular beam. The length of the Bessel beam can be approximated using an equation below:

$$DOF = \frac{D}{2(n-1)*\tan(\alpha)}$$

For example, with a 4 mm output beam, a wavelength of 1550 nm, and a 20° wedge angle, the length of the Bessel beam focal region is approximated to 15 mm.

A working distance (WD) 926 between the tip of the third focusing axicon 918 and the Bessel beam focal region 910 is a function of an inner diameter 928 of the annular ring 916. The working distance 926 measured from the tip of the axicon 918 can be approximated using an equation below, with reference to FIGS. 9A-B:

$$WD = \frac{r}{\tan((n-1)*\alpha)} - r*\tan(\alpha)$$

The above equation is derived from two below equations for X1 and X0. FIG. 9B illustrates the relationship between these equations.

$$X_0 = -r*\tan(\alpha)$$
$$X_1 = \frac{r}{\tan((n-1)*\alpha)}$$
$$WD = X_0 + X_1$$

As can be seen above the minor (i.e., inner) diameter 928 of the ring energy profile 916 affects the working distance 926. For example, a non-annular beam being acted upon by an axicon results in a Bessel beam focal region that begins at the tip of the axicon. In some embodiments, the focal region 910 is controlled to a depth within a tissue (e.g., below a surface of a tissue) by controlling a minor diameter 928 of the annular beam incident the focusing axicon 918 thereby affecting the working distance 926 of the focal region 910. In some versions, the minor diameter 928 of the annular beam 916 is a function of separation between the first axicon 912 and the second axicon. Minor diameter can be expressed in terms of a major (i.e., outer) diameter 930 of the ring energy profile 916. Specifically, minor diameter 928 is equal to the major diameter 930 less the diameter of the collimated beam 924, or:

$$\mathcal{O}_{minor} = \mathcal{O}_{Major} - \mathcal{O}_{beam}$$

Figure 10:
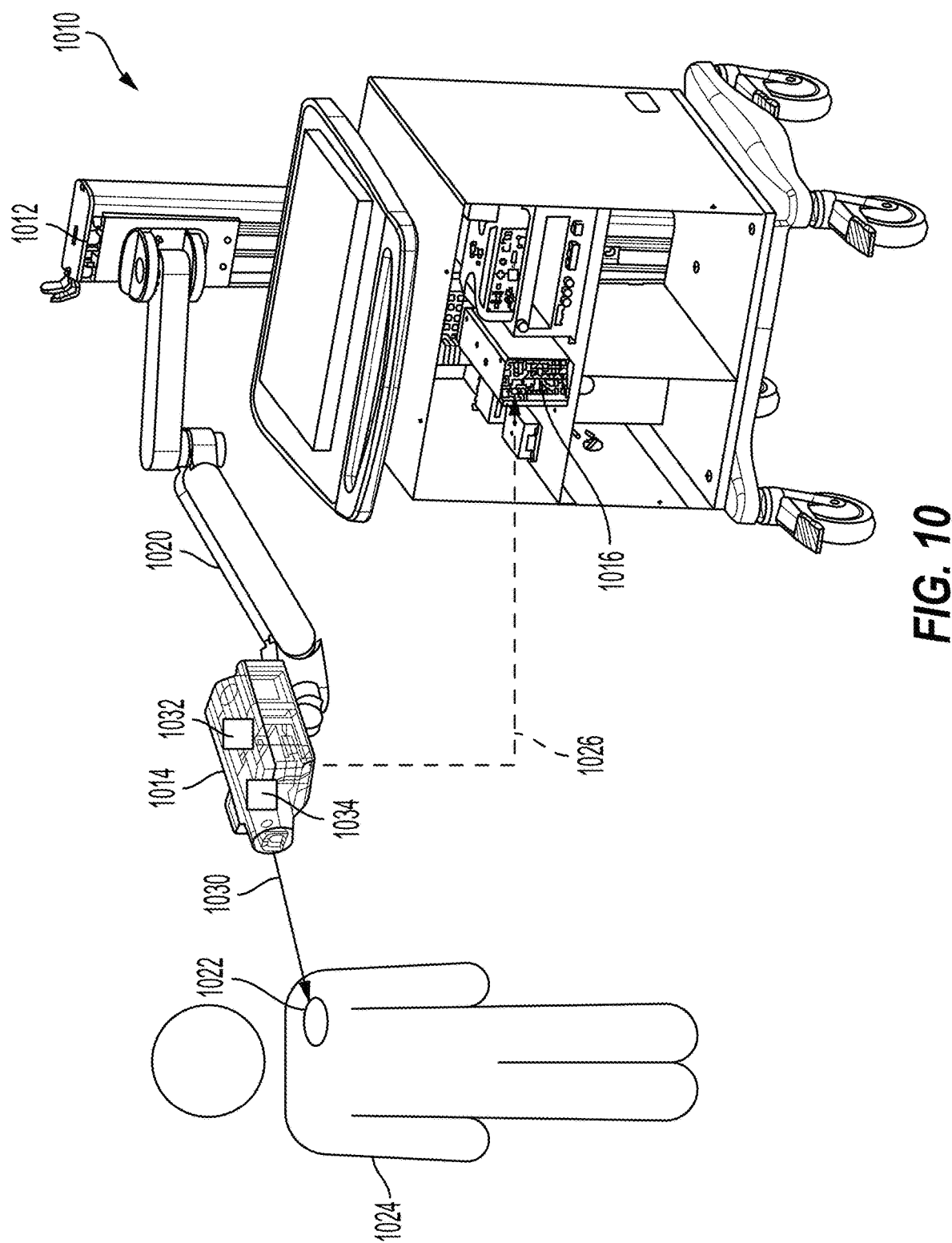

FIG. 10 illustrates one exemplary embodiment of a treatment system 1010. As shown, the treatment system 1010 includes a platform 1012, and emitter 1014, and a controller 1016. The platform 1012 can include one or more manipulator or arm 1020. The arm 1020 can be coupled to the emitter 1014 for performing various treatments on a target tissue 1022 of a subject 1024. Operation of the platform 1012 and emitter 1014 can be directed by a user, manually or using the controller 16 (e.g., via a user interface). In certain embodiments (not shown), the emitter can have a hand-held form factor and the platform 1012 can be omitted. In other embodiments, the platform can be a robotic platform and the arms can be communicatively coupled to the controller for manipulation of the emitter.

The emitter 1014 and controller 1016 (and optionally the platform 1012) can be in communication with one another via a communications link 1026, which can be any suitable type of wired and/or wireless communications link carrying any suitable type of signal (e.g., electrical, optical, infrared, etc.) according to any suitable communications protocol.

Embodiments of the controller 1016 can be configured to control operation of the emitter 1014. In one aspect, the controller 1016 can control movement of EMR 1030. As discussed in detail below, the emitter 1014 can include a source 1032 for emission of the EMR 1030 and a scanning system 1034 for manipulation of the EMR 1030. As an example, the scanning system 1034 can be configured to focus EMR 1030 to a focal region and translate and/or rotate this focal region in space. The controller 1016 can send signals to the source 1032, via the communications link 1026 to command the source 1032 to emit the EMR 1030 having one or more selected properties, such as wavelength, power, repetition rate, pulse duration, pulse energy, focusing properties (e.g., focal volume, Rayleigh length, etc.). In another aspect, the controller 1016 can send signals to the scanning system 1034, via the communications link 1026 to command the scanning system 1034 to move the focal region of the EMR 1030 with respect the target tissue 1022 in one or more translation and/or rotation operations.

Embodiments of the treatment system 1010 and methods are discussed herein in the context of treatment within skin tissue, such as a dermal layer. However, the disclosed embodiments can be employed for treatment of any tissue in any location of a subject, without limit. Examples of non-skin tissues can include, but are not limited to, surface and sub-surface regions of mucosal tissues, genital tissues, internal organ tissues, and gastrointestinal tract tissues.

Exemplary Manual Scanned System

Figure 11C:
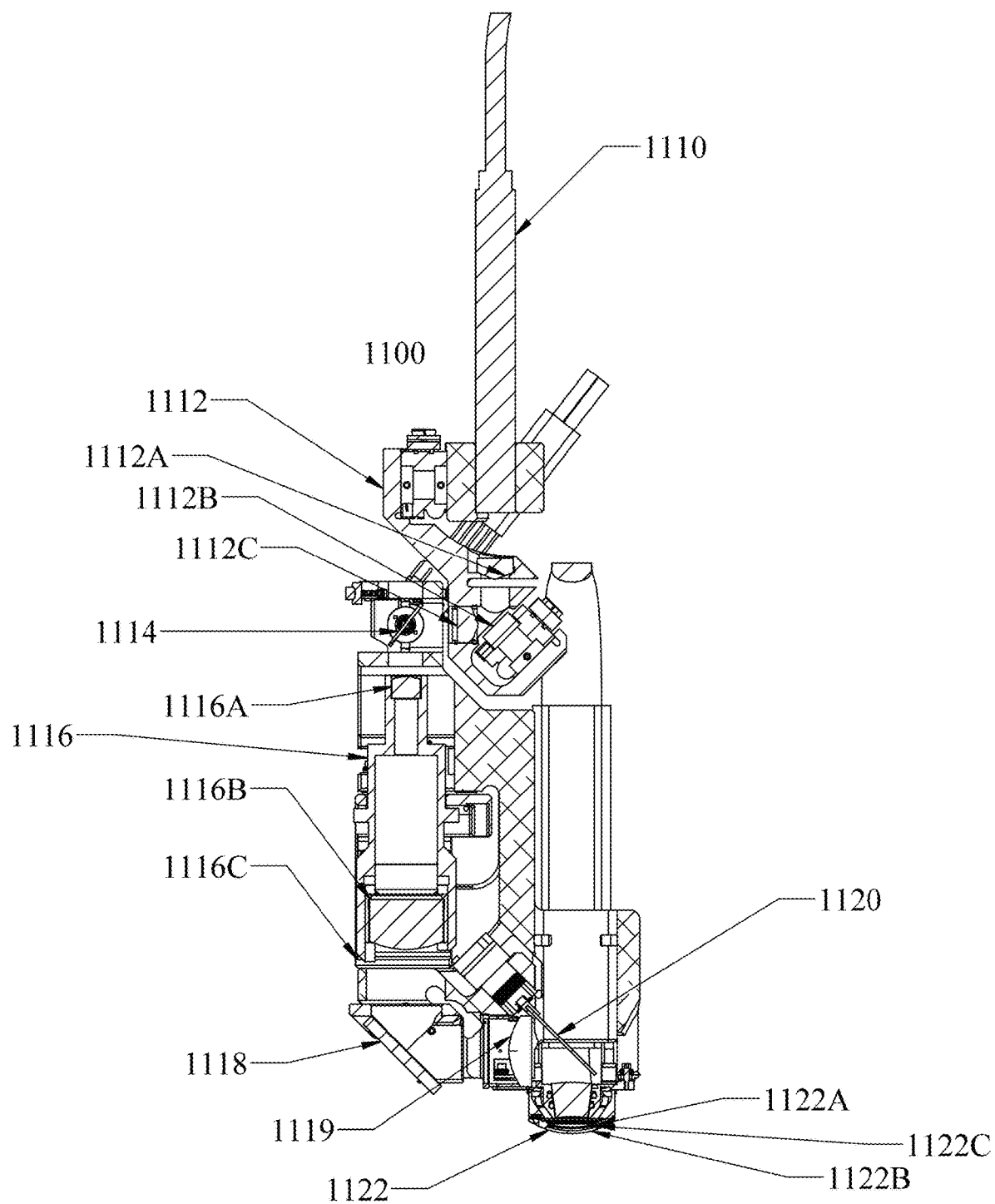
FIG. 11C illustrates a cross-sectional view of the exemplary embodiment of FIG. 11B.

In some embodiments, a hand-held system 1100 is used which is manually scanned (i.e., manually moved by a clinician) over a treatment area. FIGS. 11A-11C illustrate an exemplary embodiment, which can be scanned manually. FIG. 11A illustrates a front view of the system 1100; FIG. 11B illustrates a side view of the system 1100; and, FIG. 11C illustrates a cross-sectional view of the system 1100. Referring to FIGS. 11A-11C, a fiber laser outputs a laser beam by way of a collimator 1110. The laser beam can be of any wavelength. Specifics of wavelength selection are described in detail above. The collimated laser beam is acted upon by a beam shaper 1112. As described in detail above, the beam shaper 1112 takes the collimated laser beam from the collimator 1110 and shapes it to a transverse ring energy profile. The beam shaper, as shown in the cross-sectional view (FIG. 11C), has a first axicon 1112A, an alignment mirror 1112B, and a second axicon 1112C. The two axicons 1112A and 1112C are used to shape the beam. The alignment mirror 1112B is used to align the laser beam onto the second axicon 1112C. Typically, axicons are very sensitive to misalignment, especially misalignment of centration. After the beam shaper 1112, the laser beam is then reflected by a first galvanometer mirror 1114 and directed into and through a beam expander 1116. The beam expander is a Keplerian beam expander and includes a first positive optical element 1116A, which focuses the beam to an intermediate focus and a second positive optical element 1116B, which collimated the laser beam. In some cases, one or more of the beam expander optics is dynamic and can be moved along the optical axis. A linear stage 1116C moves the second positive optical element 1116B along the optical axis. An exemplary linear stage is a Newscale M3-LS-3.4-15 from Newscale Technologies of Victor, NY The beam expander 1116 expands the collimated ring beam, for example by a factor of between 2-20×. Upon exiting the beam expander 1116, the laser beam is reflected by a static fold mirror 1118, focused by an objective lens 1119 (e.g., An aspherical focus optic, for example, Asphericon PN: AFL25-40, from Asphericon of Jena, Germany), reflected by a second galvanometer mirror 1120, and directed to emerge from a contact window 1122. In some versions, the beam expander is an afocal relay system that is placed at conjugate distances between the first galvanometer mirror 114 and the objective lens 1119. The contact window 1122, like many described in detail above, includes a first window 1122A, a second window 1122B separated from the first window, and a coolant chamber 1122C located between the first window 1122A and the second window 1122B. The second window 1122B has a tissue contacting surface (i.e., outer surface) that is convex. This shape is advantageous in some circumstances as it helps to ensure positive contact with the tissue being treated and slides more easily of the tissue.

Figure 12:
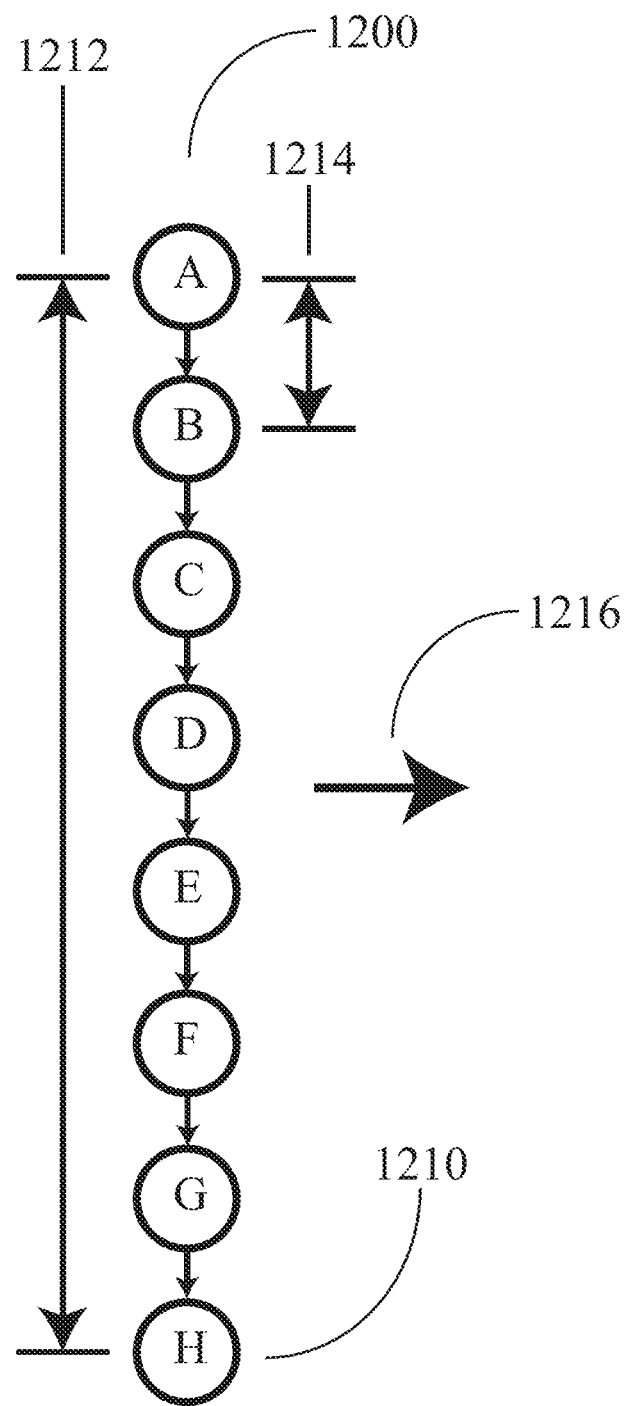
FIG. 12 illustrates a line scan pattern, according to some embodiments.

The handheld system 1100 described in FIGS. 11A-11C is used to treat an area manually. As the clinician moves the handheld system 1100 over the treatment tissue, the second galvanometer mirror 1120 scans a line of points over the surface of the skin side to side. Referring now to FIG. 12, an exemplary line of scanned points 1200 is shown. The exemplary line 1200 includes eight individual points 1210, where laser energy is delivered. The eight points 1210 are scanned to sequentially as shown in FIG. 12 from top to bottom (i.e., A-H). After the final point has had energy delivered at it (i.e., point H), the line scan is repeated and starts again. The line has a width 1212 that is approximately equal to the number of points 1210 multiplied by a pitch 1214 (i.e., distance between adjacent points). Referring again briefly to FIGS. 11A-C the line is scanned by the second galvanometer mirror 1120 of the handheld system 1100 along a manual scan direction 1216, which is generally perpendicular to the direction of the line scan 1200.

Exemplary Beam Scanning Systems

In some embodiments, beam scanning systems and methods are provided. Disclosure related to these embodiments and beam scanning systems and methods is described below. Generally, beam scanning systems and methods can be categorized in one or more of the following types pre-objective scanning, objective scanning, and post-objective scanning. Pre-objective scanning includes embodiments, in which the beam is scanned (e.g., deflected, tipped, and/or tilted) before (i.e., up beam from) being directed incident upon the objective. Objective scanning includes embodiments, in which scanning (e.g., deflecting, tipping and/or tilting) the beam is performed at the objective, for example by moving the objective. Post-objective scanning includes embodiments, in which scanning (e.g., deflecting, tipping, and/or tilting) is performed after (i.e., down beam from) the objective.

Pre-Objective Scanning

Figure 13:
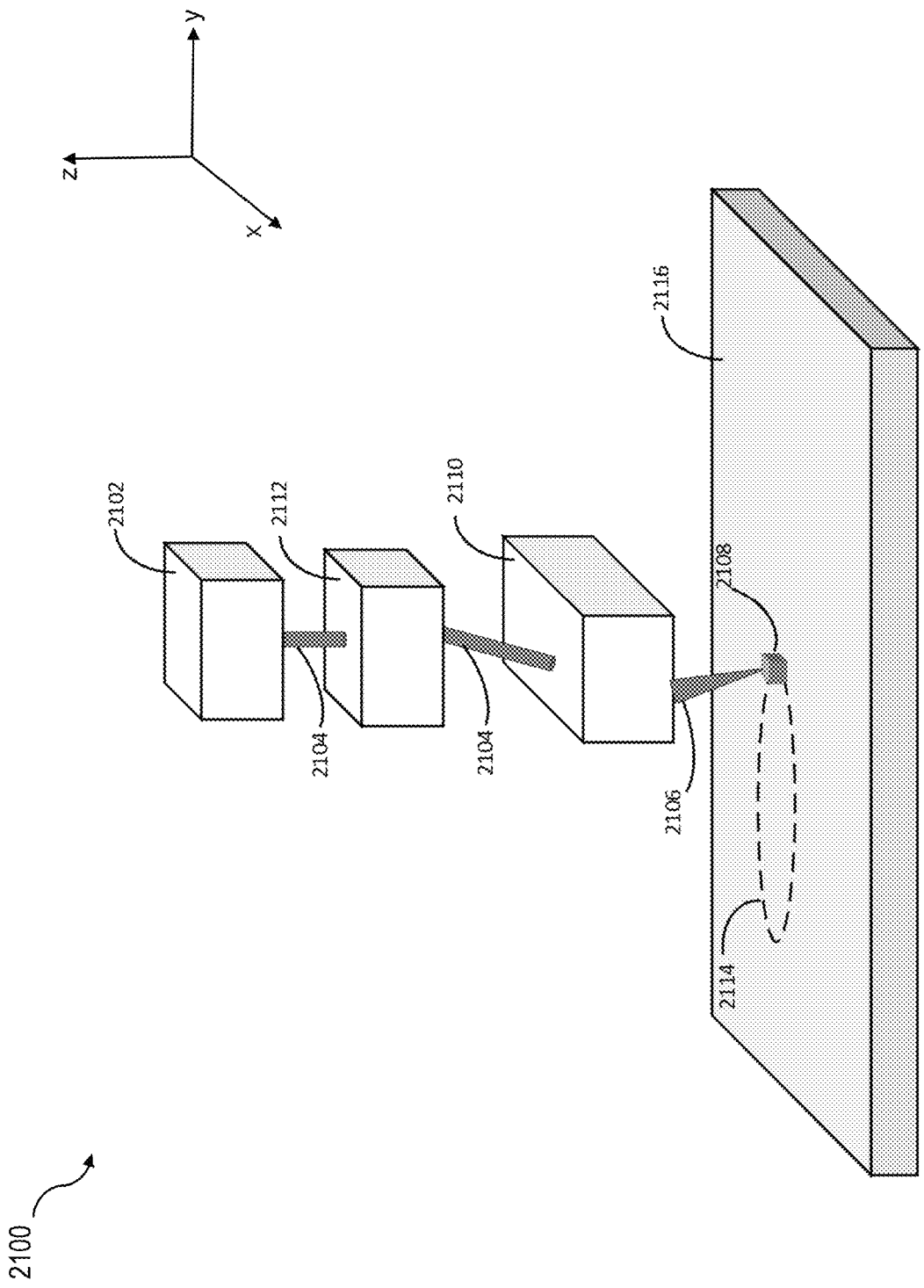
FIG. 13 is a schematic illustration of a pre-objective scanning system.
Figure 24:
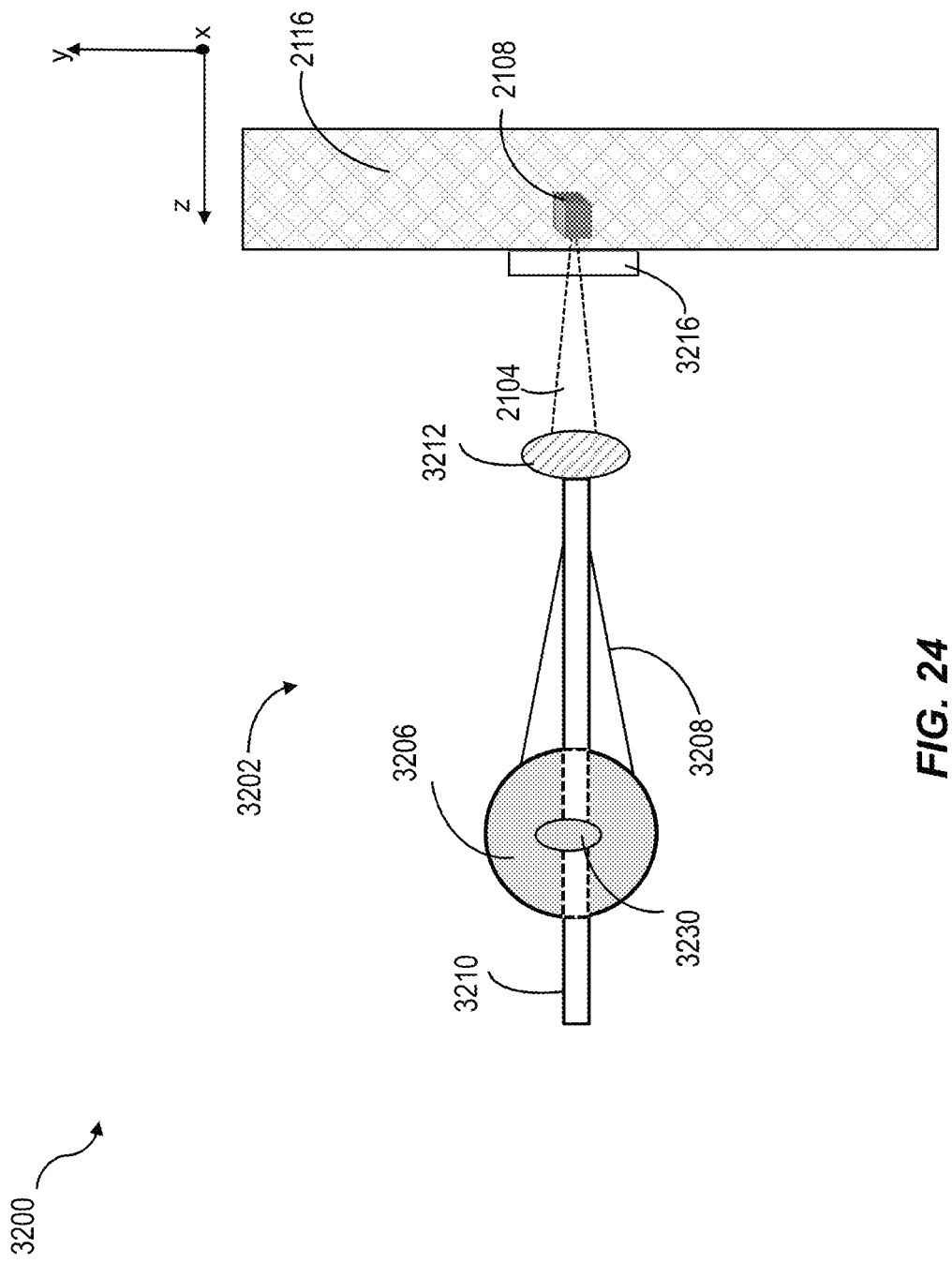
FIG. 24 is an illustration of an exemplary pre-objective scanning system.

FIG. 13 is a schematic illustration of a pre-objective scanning system 2100, which includes an objective 2110 and a scanning unit 2112. The scanning unit 2112 can receive a laser beam 2104 from a laser source 2102 and direct the laser beam 2104 to the objective 2110. The objective 2110 can receive the laser beam 2104 and direct a focused laser beam 2106 to a focal volume 2108 in the treatment region of a tissue 2116 (e.g., skin). The scanning system 2112 can alter the direction of the laser beam 2104 directed towards the objective 2110. For example, the scanning system 2112 can alter the direction of the outgoing laser beam along one or more scan directions. Change in the direction of the laser beam 2104 impinging the objective 2110 can cause the focal volume 2108 to trace a treatment path 2114 in the tissue 2116. The focal volume 2108 traverses the treatment path 2114 at a scan rate. The scanning unit 2112 includes one or more optical elements that can direct the laser beam 2104 (or a portion of the laser beam 2104) to the objective 2110. The pre-objective scanning system 2100 can include a contacting surface (e.g., as shown in FIG. 24) that can be positioned between the objective 2110 and the tissue 2116. The contacting surface can apply pressure the surface of the tissue 2116, and allow for dissipation of heat from the surface of the tissue 2116.

Figure 14:
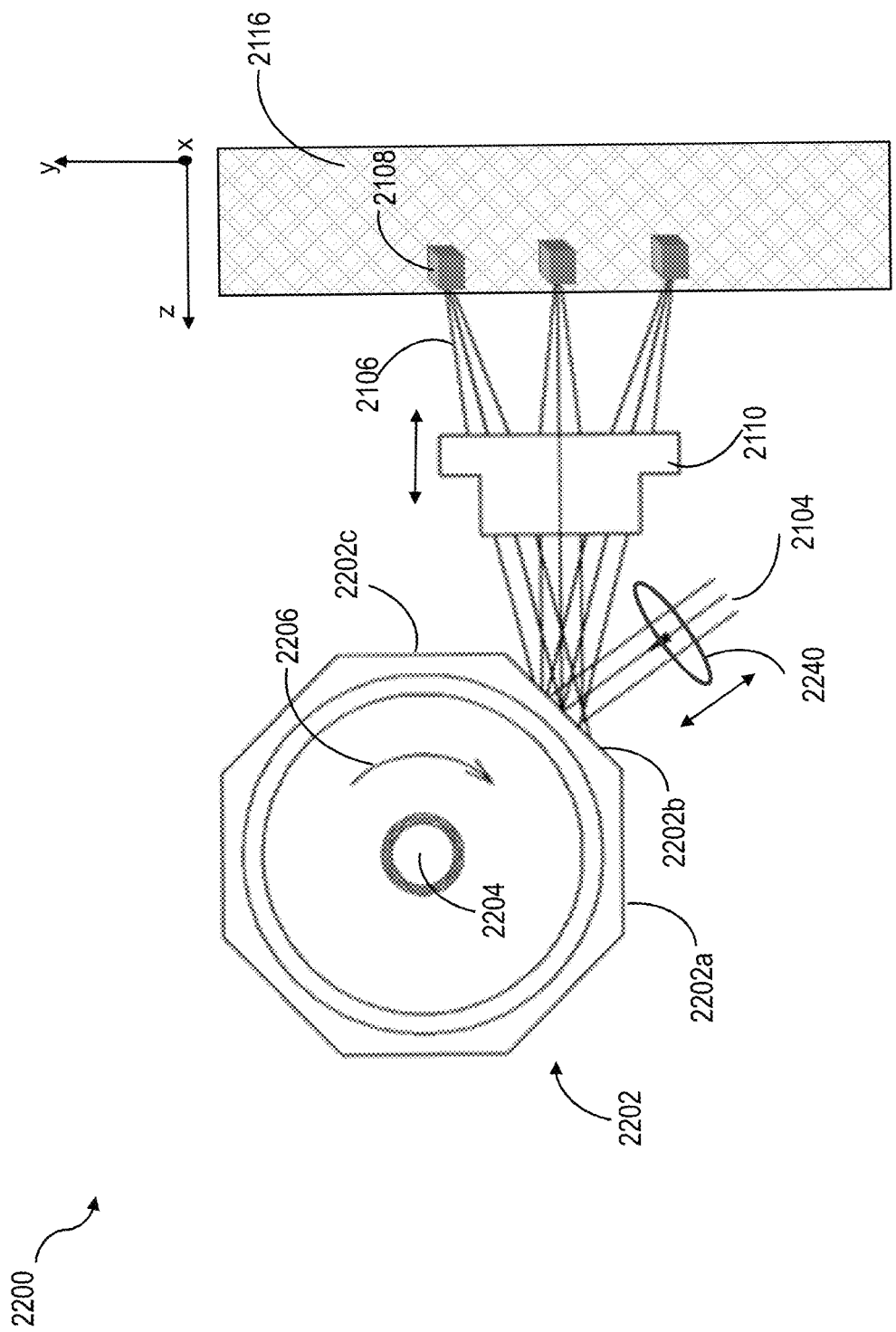
FIG. 14 is an illustration of an exemplary pre-objective scanning system.

FIG. 14 is an illustration of an exemplary pre-objective scanning system 2200. The scanning system 2200 includes a polygon scanner 2202 which can receive the incident laser beam 2104 (e.g., from a laser source 2102) and direct the incident laser beam 2104 towards an objective 2110 (e.g., f-theta lens). The outgoing direction of the laser beam 2104 (e.g., incidence angle with which the laser beam 2104 impinges on the objective 2110) can determine the location of the focal volume 2108 in the tissue 2116 (e.g., in the x-y plane). According to some embodiments, the laser source 2102 provides a plurality of laser pulses resulting in a plurality of corresponding focal volumes. A distance between two focal volumes resulting from sequential laser pulses is focal volume pitch.

The polygon scanner 2202 can include multiple reflecting surfaces (e.g., 2202a-c). The polygon scanner 2202 can rotate about an axis 2204 along a rotational direction 2206. As the reflecting surfaces 2202a-c rotate around the axis 2204 (e.g., angular position of the reflecting surfaces 2202a-c with respect to the axis 2204 changes), the angle of incidence of the incident laser beam 2104 in the y-z plane changes. This varies the direction of the outgoing laser beam 2104 along a first scan direction (e.g., along the y-axis). For example, if a reflecting surface (e.g., 2202b) is rotating about the axis 2204 along the rotational direction 2206, the direction of the outgoing laser beam sweeps from a higher y-value to a lower y-value.

The axis 2204 can tilt/rotate about the z-axis and/or the x-axis. This can cause the angle of incidence of the incident laser beam 2104 in the x-z plane to change, which varies the direction of the outgoing laser beam 2104 along a second scan direction (e.g., along the x-axis). Rotation of the polygon scanner 2202 and the rotation/tilting of the axis 2204 can allow for varying of the direction of the outgoing laser beam 2104 that can result in the scanning of the outgoing laser beam 2104 in the x-y plane.

Based on the variation of the direction of the outgoing laser beam 2104, the objective 2110 can trace the focal volume 2108 along one or more treatment paths in the tissue 2116. For example, variation of the direction of the outgoing laser beam 2104 due to rotation of the polygon scanner 2202 can cause the focal volume 2108 to move along the y-axis. Variation of the direction of the outgoing beam due to tilting of the axis 2204 can cause the focal volume 2108 to move along the x-axis. In one implementation, the pre-objective scanning system 2200 can be moved along the x-axis relative to the tissue 2116. This can result in the tracing of the focal volume 2108 location along the x-axis.

Focal volume 2108 can also be moved along a third treatment path, namely, along the z-axis. This can be done by varying the objective 2110 along the z-axis (e.g., away from or towards the tissue 2116). Alternatively or additionally, lens 2240 can be placed in the beam path of the incident or outgoing laser beam 2104. By varying the position of the lens 2240 along the beam propagation direction 2242 (also referred to as optical axis), the location focal volume 2108 can be traced along the z-axis (e.g., depth of the tissue 2116).

Figure 15:
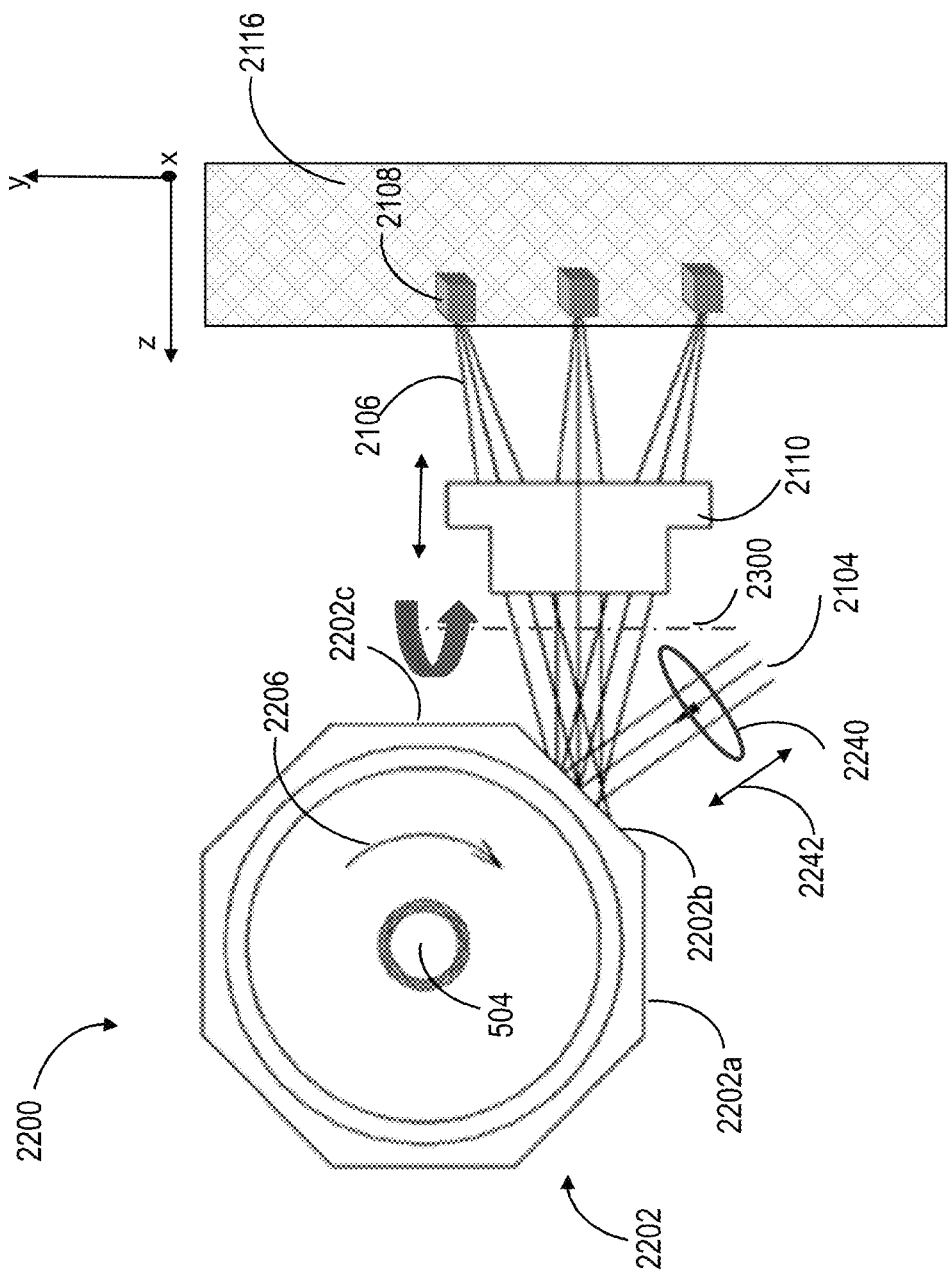
FIG. 15 illustrates a beam folding plane for the pre-objective scanning system in FIG. 14.

FIG. 15 illustrates a beam folding plane 2300 for the pre-objective scanning system 2200. The scanning system 2200 can be made compact (e.g., by reducing the extent of the scanning system 2200 along the z-axis) by folding the scanning system 2200 about the beam folding plane 2300. This can be achieved, for example, by placing a mirror (e.g., a flat mirror) in the beam folding plane and orienting the mirror parallel to the x-y plane.

Figure 16:
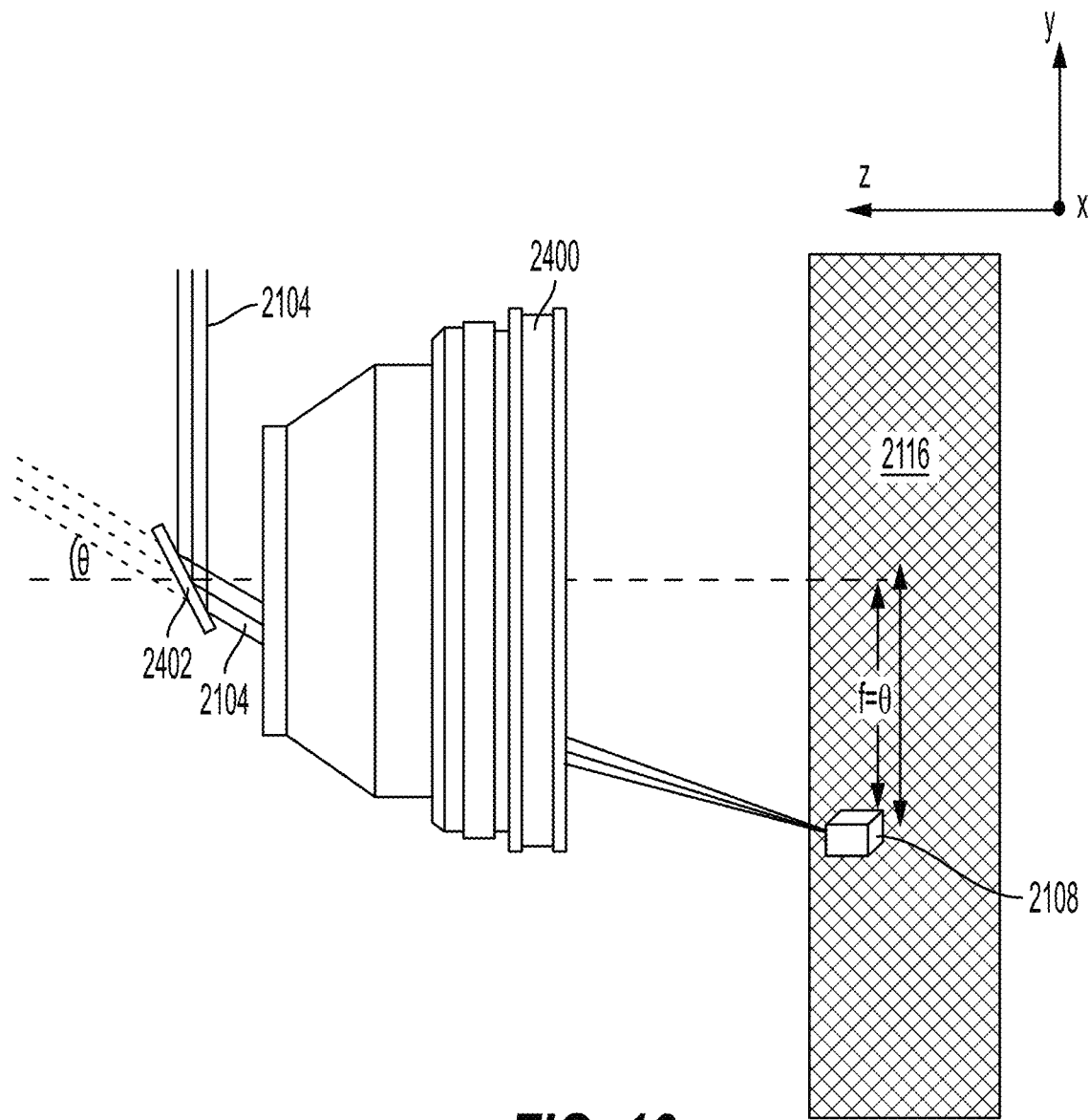
FIG. 16 illustrates an exemplary f-theta lens.

FIG. 16 illustrates an exemplary f-theta lens 2400 that can be used as an objective in the pre-objective scanning system 2200. The incident laser beam 2104 can impinge on a reflecting surface 2402 (e.g., reflective surface 2202b of the polygon scanner 2202) which can direct an outgoing laser beam 2104 to the f-theta lens 2400. The orientation of the reflecting surface 2402 can determine the incidence angle at which the outgoing laser beam 2104 impinges on the f-theta lens (e.g. angle of incidence in the y-z plane). The incidence angle can determine the location of the focal volume 2108 (e.g., along the y-axis).

Figure 17:
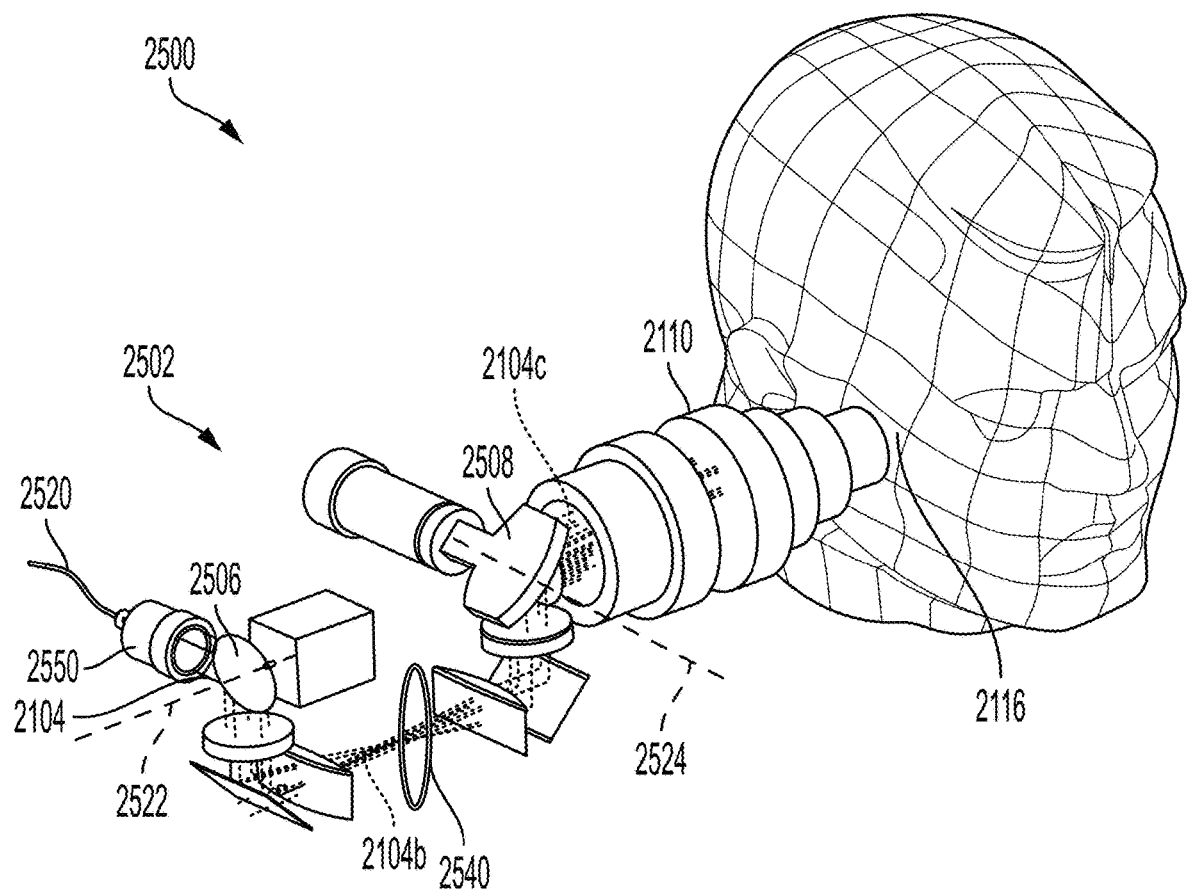
FIG. 17 is an illustration of an exemplary pre-objective scanning system.

FIG. 17 is an illustration of an exemplary pre-objective scanning system 2500. The scanning system 2500 includes a mirror system which can receive the laser beam 2104 (e.g., through an optical fiber 2520) and direct the laser beam 2104 towards an objective 2110 (e.g., f-theta lens). The direction of the outgoing laser beam 2104c can determine the location of the focal volume 2108 in the tissue 2116 (e.g., in the x-y plane).

The mirror system can include two scanning mirrors. The first scanning mirror 2506 can rotate about a first axis 2522 (e.g., clockwise counter clockwise, etc.), and the second scanning mirror 2508 can rotate about a second axis 2524 (e.g., clockwise, counter clockwise, etc.). As the first scanning mirror 2506 rotates the angle of incidence of the incident laser beam 2104 on the mirror 2506 changes. This varies the direction of the outgoing laser beam 2104b along a first scan direction (e.g., along the y-axis). As the second scanning mirror 2508 rotates the angle of incidence of the laser beam 2104b on the scanning mirror 2508 changes. This varies the direction of the outgoing laser beam 2104c along a second scan direction (e.g., along the x-axis). Rotation of the first scanning mirror 2506 and the second scanning mirror 2508 can allow for varying of the direction of the outgoing laser beam 2104c that can result in the scanning of the outgoing laser beam 2104c in the plane of the objective.

Based on the variation of the direction of the outgoing laser beam 2104c, the objective 2110 can trace the focal volume 2108 (not shown) along one or more treatment paths in the tissue 2116. For example, variation of the direction of the outgoing laser beam 2104c due to rotation of the first scanning mirror 2506 can cause the focal volume 2108 to move along a first treatment path. Variation of the direction of the outgoing laser beam 2104c due to rotation of the second scanning mirror 2508 can cause the focal volume 2108 to move along a second treatment path.

The scanning system 2500 can include a lens 2540 that can be placed in the beam path of laser beams 2104a, 2104b or 2104c. By varying the position of the lens 2540 along the beam propagation direction, the location focal volume 2108 can be traced along the depth of the tissue 2116.

Figure 18:
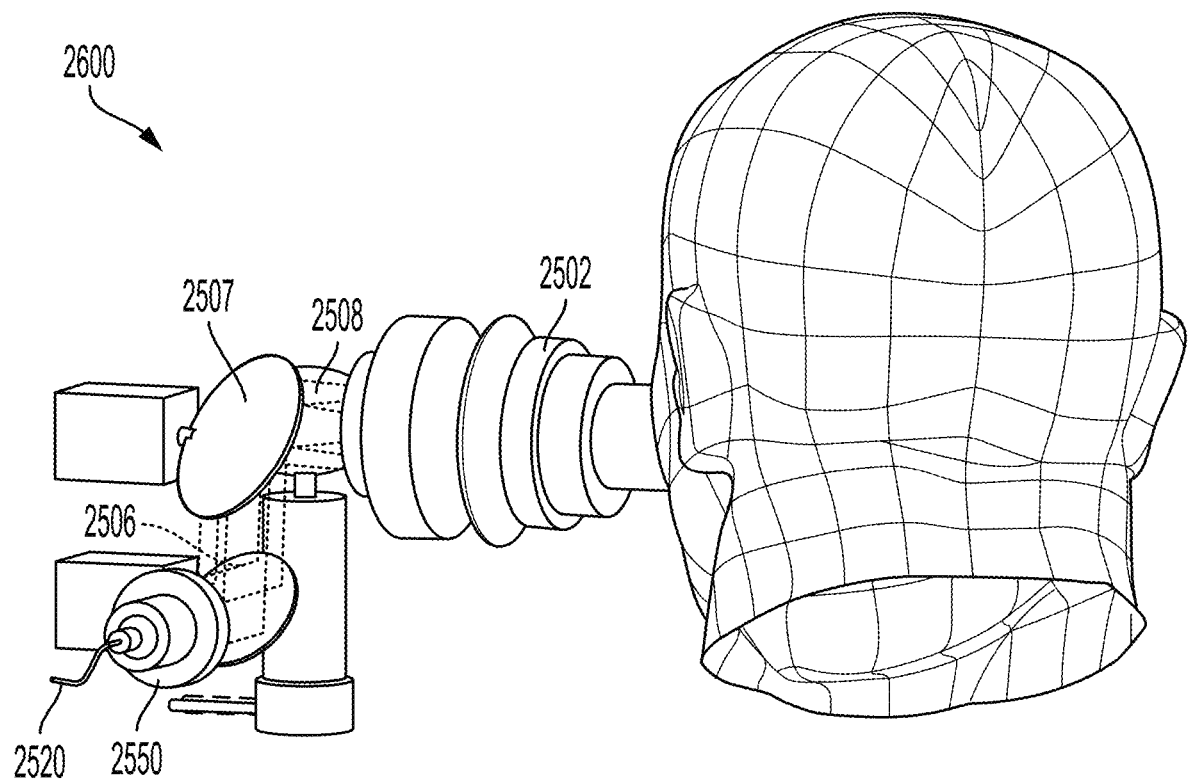
FIG. 18 is an illustration of an exemplary pre-objective scanning system.

In some implementations of the scanning mirror system, the variation in the direction of the laser beam 2104b by the first scanning mirror 2506 can be large. This can prevent the laser beam 2104b from impinging on the second scanning mirror 2508. Additionally, large angles of incidence of the laser beam 2104b on the second scanning mirror 2508 can result in curved treatment path of the focal region. These effects can be prevented/reduced by including a third scanning mirror between the first scanning mirror 2506 and the second scanning mirror 2508. FIG. 18 is an illustration of an exemplary pre-objective scanning system 2600 that includes a third scanning mirror 2507 which is downstream from the first scanning mirror 2506 and upstream from the second scanning mirror 2508. The third scanning mirror 2507 can allow for smaller second scanning mirror 2508, and can prevent/reduce the curvature of the focal region treatment path.

FIGS. 19A-19C illustrates various scanning patterns of an outgoing beam (e.g., outgoing laser beam 2104) from the scanning unit 2112 (e.g., polygon scanner 2202, mirror system 2502, etc.). FIG. 19A illustrates a first scanning pattern in which the outgoing beam scans in the following sequence: (a) left to right movement (e.g., along the x-axis), (b) top to down movement (e.g., along the y-axis), and (c) right to left movement (e.g., along the negative x-axis). FIG. 19B illustrates a second scanning pattern in which the outgoing beam scans in the following sequence: (a) left to right movement (e.g., along the x-axis), (b) a superposition of top to down movement and right to left movement, and (c) left to right movement. FIG. 19C illustrates a third scanning pattern in which the outgoing beam scans in the following sequence: (a) superposition of left to right movement and top to down movement, and (b) superposition of right to left movement and top to down movement. Movements of the light beam (e.g., from left to right, from right to left, from top to down, etc.) can be obtained by clockwise or anticlockwise rotation of scanning mirrors 2506, 2507, 2508, or by rotation/axis tilting of the polygon scanner 2202.

Figure 20:
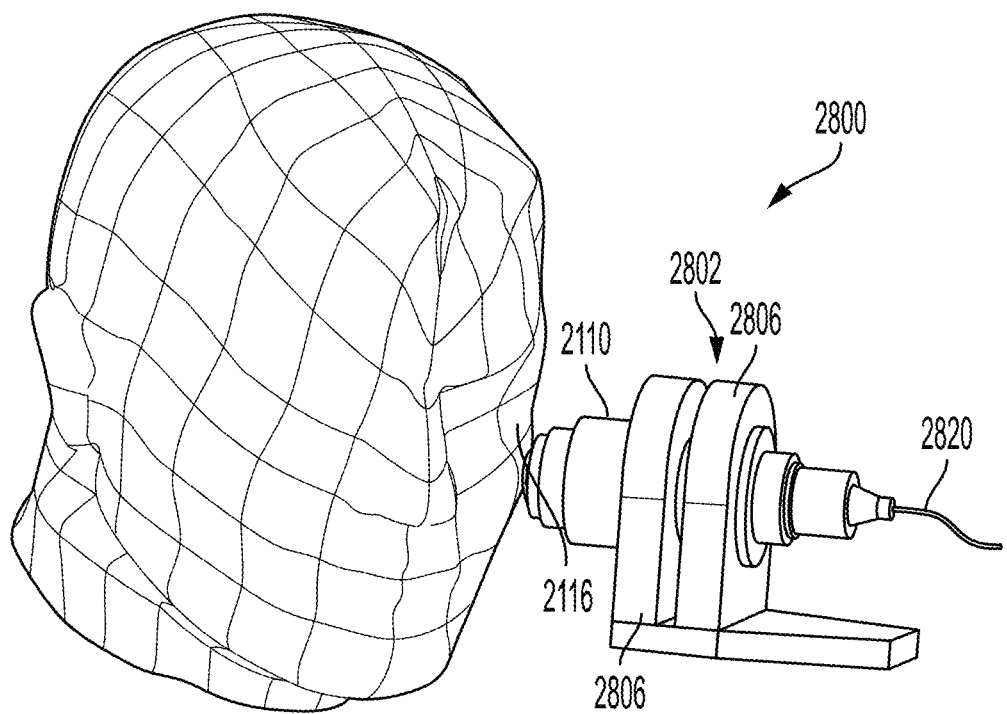
FIG. 20 is an illustration of an exemplary pre-objective scanning system.

FIG. 20 is an illustration of an exemplary pre-objective scanning system 2800. The scanning system 2800 includes a prism system 2802 which can receive an incident laser beam 2104 (e.g., through an optical fiber 2820) and transmit an outgoing beam 2105 (see FIG. 21) towards an objective 2110 (e.g., f-theta lens). The direction of the outgoing beam 2105 can determine the location of the focal volume 2108 in the tissue 2116.

Figure 21:
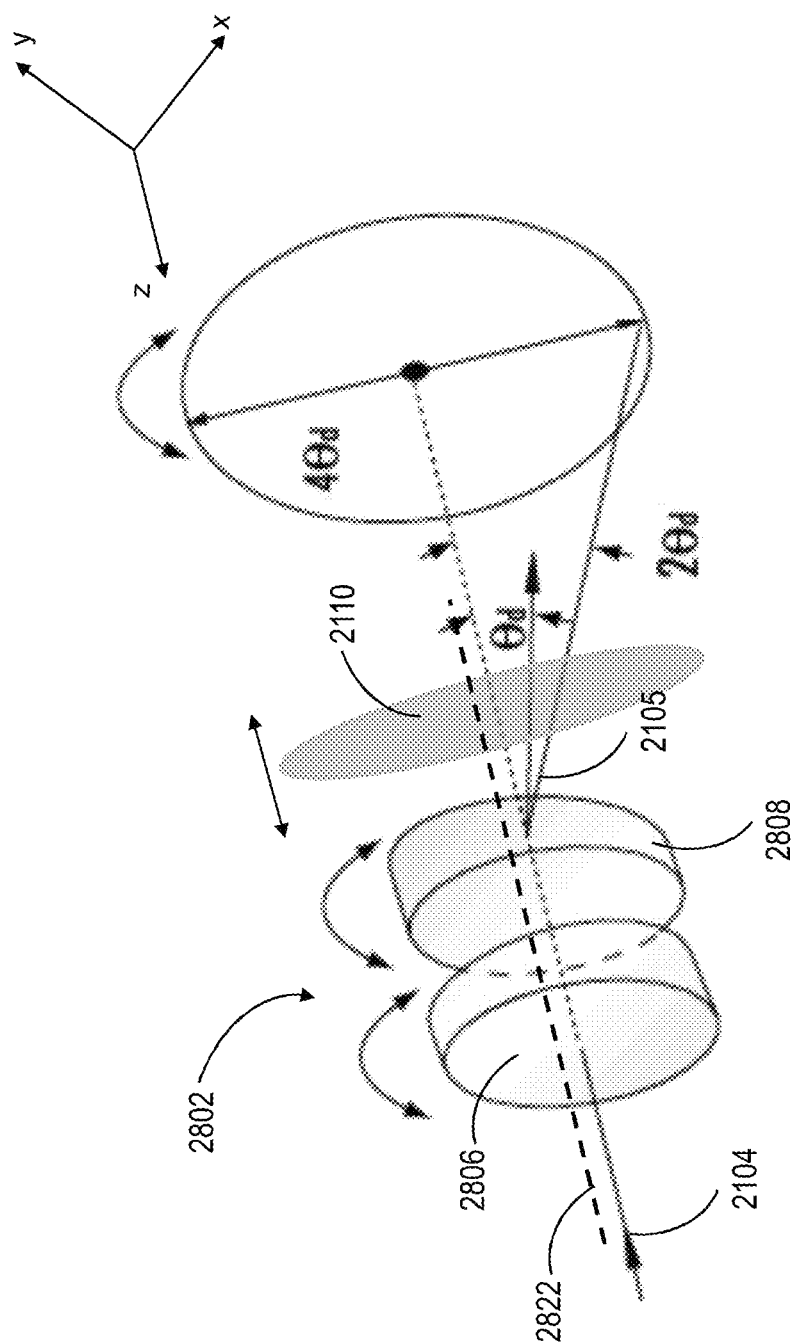
FIG. 21 illustrates an exemplary prism system of the pre-objective scanning system of FIG. 23.

FIG. 21 illustrates a prism system 2802 that can be used with the pre-objective scanning system 2800. The prism system 2802 includes a first prism 2806 and a second prism 2808 that can rotate about a common axis 2822. Each of the prisms can alter the direction of an incident light beam by a characteristic angle. If both the first prism 2806 and the second prism 2808 are perfectly aligned, the direction of an incident laser beam is altered by twice the characteristic angle. If the first prism 2806 and second prism 2808 are perfectly misaligned, the direction of the incident laser beam remains unchanged. For all other orientations of the prisms 2806 and 2808, the direction of the incident laser beam can be altered by an angle that lies in the range between zero degrees and twice the characteristic angle.

If both the prisms 2806 and 2808 are rotating at the same angular velocity (e.g., their relative orientation does not change during rotation), the outgoing beam 2105 scans along a circular treatment path. If the prisms 2806 and 2808 are rotating at different angular velocities, their relative orientation will change during rotation. For example, the prism pair will swing between the states of perfect alignment (where the direction of the outgoing beam is deviated by twice the characteristic angle) and perfect misalignment (where the direction of the outgoing beam remains unchanged).

Figure 22:
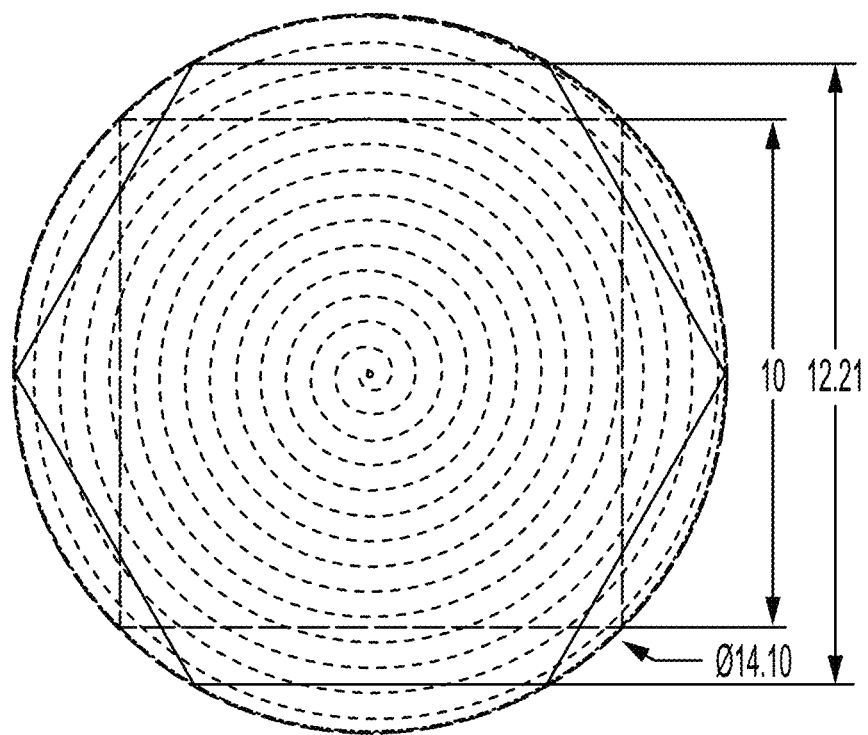
FIG. 22 illustrates an exemplary scanning pattern associated of FIG. 25.

FIG. 22 illustrates a scanning pattern of the outgoing beam 2105 resulting from the prism system 2802 where the angular velocities of the first and second prisms are different. The outgoing beam forms a spiral pattern—the outgoing beam 2105 can spiral inwards (e.g., until it reaches the center) which can be followed by outward spiral.

Figure 23:
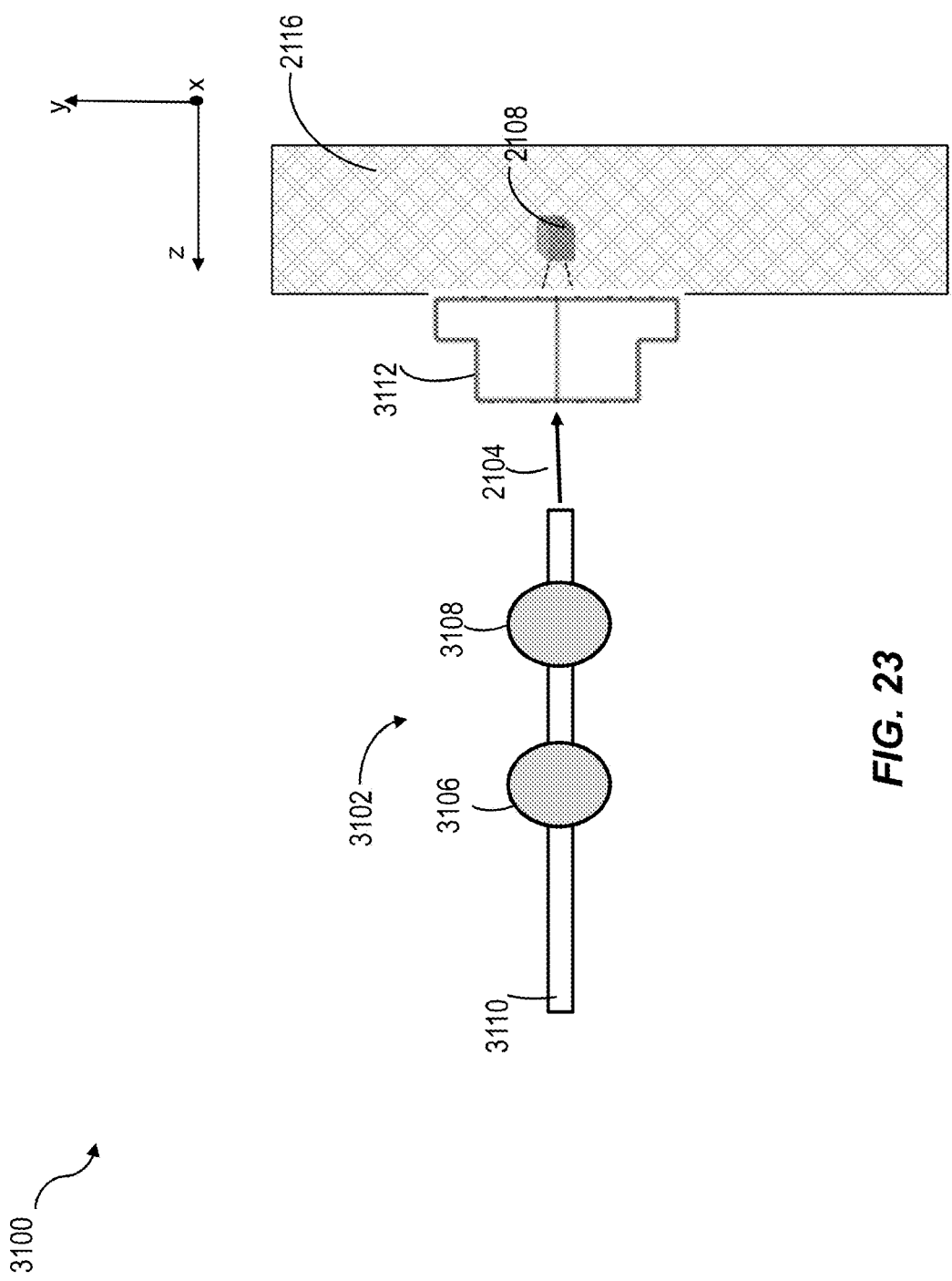
FIG. 23 is an illustration of an exemplary pre-objective scanning system.

FIG. 23 is an illustration of an exemplary pre-objective scanning system 3100. The scanning system 3100 includes a scanning unit 3102 coupled to an optical fiber 3110 that can guide the laser beam 2104. The scanning unit 3102 can include a first actuator 3106 and a second actuator 3108. The first actuator can rotate a portion of the optical fiber 3110 (e.g., tip of the fiber proximal to the objective 3112) about the x-axis. This varies the direction of the outgoing laser beam 2104 along a first scan direction (e.g., along the y-axis). The second actuator 3108 can rotate a portion of the optical fiber 3110 (e.g., tip of the fiber proximal to the objective 3112) about the y-axis. This varies the direction of the outgoing laser beam 2104 along a second scan direction (e.g., along the x-axis). Actuation by the first and second actuators can allow for varying of the direction of the outgoing laser beam 2104 that can result in the scanning of the outgoing laser beam 2104 in the plane of the objective 3112 (e.g., x-y plane). Based on the variation of the direction of the outgoing laser beam 2104, the objective 3112 (e.g., f-theta lens) can trace the focal volume 2108 along one or more treatment paths in the tissue 2116.

FIG. 24 is an illustration of an exemplary pre-objective scanning system 3200. The scanning system 3200 includes a scanning unit 3202 coupled to an optical fiber 3210 (e.g., rigidly coupled) that can guide the laser beam 2104. The scanning unit 3202 can include a six-axis actuator 3206 and a support arm 3208. A portion of the optical fiber 3210 can be rigidly coupled to a mounting location 3230 on the six-axis actuator 3206. The support arm 3208 can support the portion of the optical fiber proximal to the tissue 2116.

The six-axis actuator 3206 can move the optical fiber 3210 along the x, y and z axes. Additionally or alternatively, the six-axis actuator 3206 can rotate the optical fiber 3210 about the x, y and z axes. Tip of the optical fiber 3210 can be coupled to the objective 3212 that can focus the outgoing laser beam 2104 to a focal volume 2108 in the tissue 2116. The pre-objective scanning system 3200 can also include a contacting surface 3216 that can lie in the optical path of the outgoing laser beam 2104 between the objective 3212 and the tissue 2116.

The focal volume 2108 can be moved along a first treatment path (e.g., along the x axis) by rotating the optical fiber around the y-axis. The focal volume 2108 can also be moved along a second treatment path (e.g., along the y axis) by rotating the optical fiber around the x axis. In some implementations, it may be desirable to alter the distance between the tip of the optical fiber 3210 and the tissue 2116 (e.g., by moving the tip of the optical fiber along the z-axis) during rotation (e.g., along the x axis, y axis, etc.) to ensure that the focal volume 2108 remains at a fixed depth in the tissue 2116.

Objective Scanning

Figure 25:
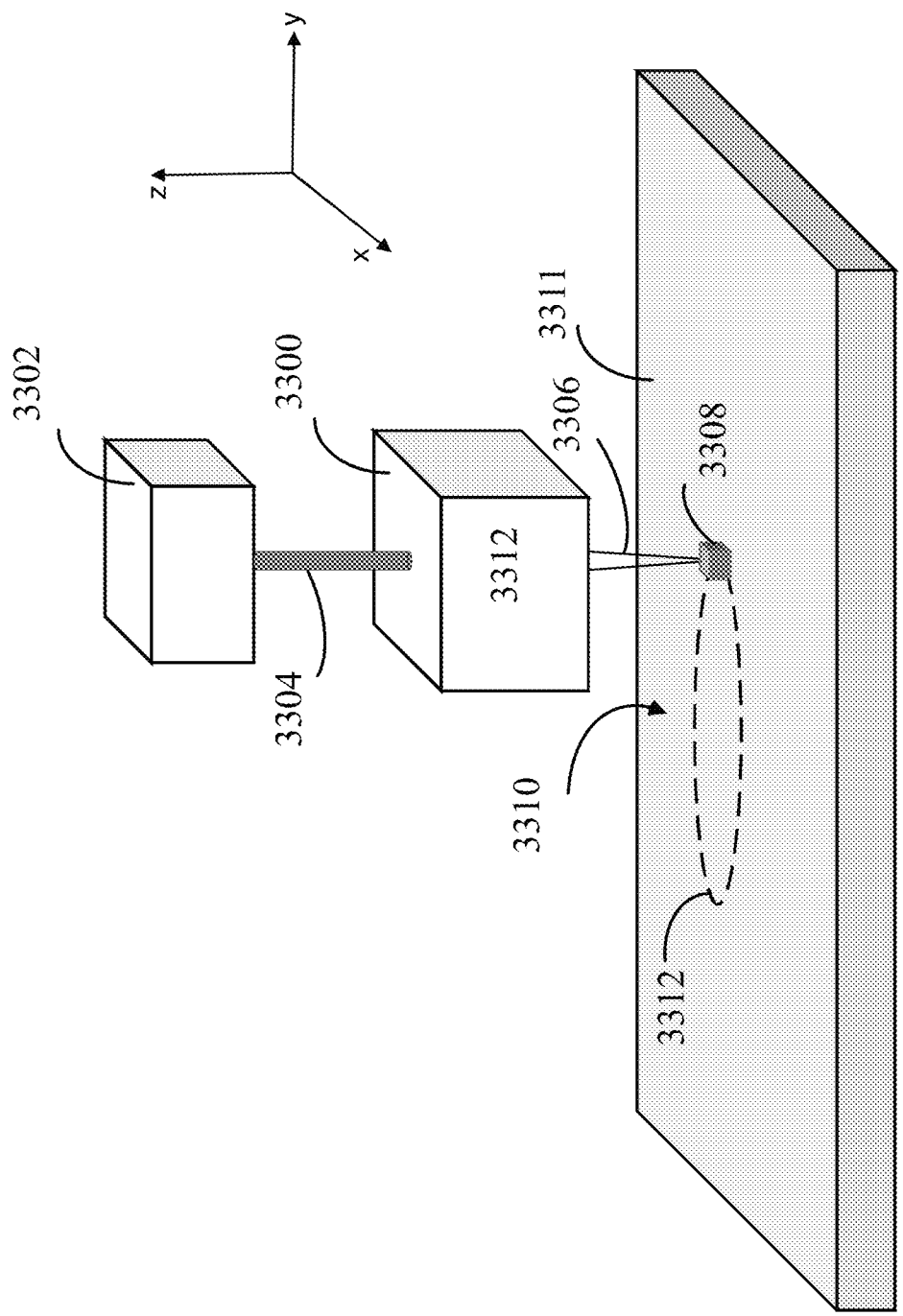
FIG. 25 is a schematic illustration of a rotary objective scanning system.

FIG. 25 is a schematic illustration of a rotary objective scanning system 3300. The rotary objective scanning system 3300 can receive a laser beam 3304 from a laser source 3302. The scanning system 3300 includes an objective (not shown) that focus the laser beam 3304 and directs a focused laser beam 3306 to a focal region 3308 in the treatment region 3310 of a tissue 3311 (e.g., skin). As the objective moves (e.g., relative to the scanning system 3300 and/or due to movement of the entire scanning system 3300), the focal region can trace a treatment path 3312 through the treatment region 3310. The treatment path 3312 can have path geometries (e.g., circular, elliptical, and the like). The scanning system 3300 includes optical elements that can direct the laser beam 3304 (or a portion of the laser beam 3304) towards the moving objective.

The scanning system 3300 can also include an interface (also referred to as "base," "window," or "contacting surface") that can stabilize the treatment region 3310 and/or facilitate control and uniformity of the irradiation profile. For example, the interface can immobilize the treatment region 3310 through application of pressure and/or by including a gel pad between the interface and the treatment region. Pressure applied by the interface on the treatment region 3310 can be detected by a pressure detector. The interface can also include a contact sensor that detect relative motion between the skin and the interface. Pressure provided by the interface on the treatment region can also blanche (or remove some blood from) the volume of treatment region being irradiated. This can result in selectivity of absorption of focused laser beam 3306 by the treatment region (e.g., pigmented cells in the treatment region) while reducing a risk of unwanted damage to blood vessels.

The interface can cool/dissipate heat from the treatment region 3310 that can be generated, for example, by heating of the treatment region 3310 due to the focused laser beam 3306. The interface can be made of materials suitable for heat dissipation (e.g., sapphire, diamond, glass, and the like). In some implementations, the interface can include a cooling system that can prevent the temperature of the treatment region from crossing a threshold temperature. The cooling system can include a temperature sensor that can detect the temperature of the treatment region. If the temperature exceeds the threshold temperature, a user can be notified and/or a cooling unit (e.g., Peltier device, cryospray, conductive cold conduit, and the like) can be activated to cool the treatment region.

The rotary objective scanning system can have various embodiments. Two exemplary embodiments of the rotary objective scanning system include an in-plane rotary objective scanning system and a transverse rotary objective scanning system, both of which are described below.

Figure 26:
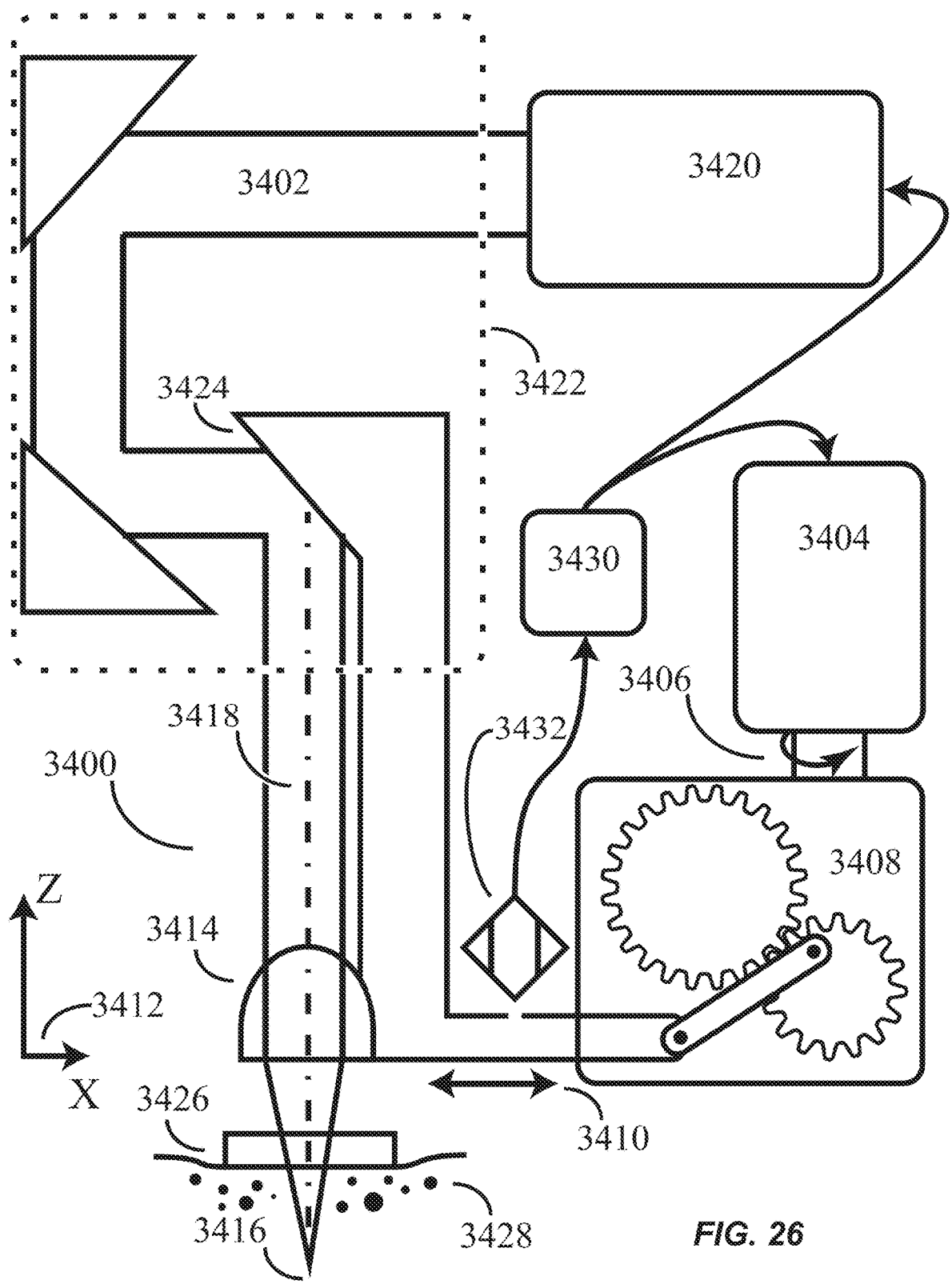
FIG. 26 schematically represents a 1-dimensional (1D) beam scanning system, according to some embodiments.

FIG. 26 schematically represents a system 3400 for scanning an electromagnetic radiation (EMR) beam 3402 according to some embodiments. A motor 3404 generates a rotational movement 3406. The motor 3404 is operatively coupled to a reciprocating mechanism 3408, such that the rotational movement 3406 drives the reciprocating mechanism 3408. The reciprocating mechanism 3408 converts the rotational movement 3406 into a reciprocating movement 3410 that acts linearly generally along a first scanned axis 3412 (e.g., an x-axis). According to some embodiments, the reciprocating mechanism includes one or more of the following: a cam and follower, a crank and slider, a Scotch yoke, and a multi-bar linkage. According to some embodiments, the reciprocating movement 3410 moves with a plurality of strokes (e.g., two strokes, a forward stroke and a backward stroke). Typically, the reciprocating mechanism 3408 is configured to provide the reciprocating movement 3410 with a constant speed. Said another way, the reciprocating movement 3410 has a velocity profile that is substantially flat over some portion of at least one stroke.

Embodiments of the constant speed can adopt a predetermined or desired constant speed. For instance, the desired constant speed can be selected from the range of about 2 mm/S to about 5 m/S. In certain embodiments, the constant speed can be a selected percentage of the desired constant speed. As an example, the selected percentage can be selected from the range of about 10% to about 90% of the desired constant speed (e.g., about 50%).

The portion of the stroke of the reciprocating movement 3410 over which constant speed is provided can vary. For instance, the portion of the stroke having constant speed can be selected from the range of about 5% to about 95%. (e.g., at least about 10%).

A focus optic 3414 is operatively coupled to the reciprocating mechanism 3408, such that it experiences and moves according to the reciprocating movement 3410. The focus optic 3414 is configured to focus the EMR beam 3402 to a focus 3416 along an optical axis 3418. The reciprocating movement 3410 of the focus optic 3414 thereby moves the focus 3416 and the optical axis 3418 along the first scanned axis 3412.

According to some embodiments, the EMR beam 3402 is generated by an electromagnetic radiation (EMR) source 3420. Examples of EMR sources are described in detail below. The EMR beam 3402 is delivered from the EMR source 3420 and directed incident upon the focus optic 3414 by an optical system 3422. Typically, the optical system 3422 includes one or more reflective and/or transmissive optics. According to some embodiments, the optical system 3422 includes one or more dynamic optical elements 3424 that move. For example, the dynamic optical element 3424 in the form of a reflector placed along the optical axis 3418, and mechanically affixed to the focus optic 3414, therefore experiences and moves according to the reciprocating movement 3410. As discussed in greater detail below, the EMR source 3420 can be configured to operate in a pulsed mode according to a predetermined repetition rate. A relationship between the repetition rate of the EMR source and the constant speed of the reciprocating movement 3410 can determine a nominal pitch between sequential pulsed focuses along the first scanned axis 3412.

According to some embodiments, a housing 3426 is disposed between the focus optic 3414 and the focus 3416 along the optical axis. The housing 3426 is configured to contact a target surface, e.g., a surface of a target tissue 3428, via a contacting surface. As shown, the focus 3416 is positioned down beam of the surface of the target tissue 3428. The housing 3426 is described in greater detail below. In one embodiment, the contacting surface can be configured to cool the target tissue 3428. In another embodiment, one or more sensors (e.g., a pressure sensor, a contact sensor, a temperature sensor, etc.) can be located within the housing and configured to measure one or more variables of the target tissue. The one or more variables can include at least one pressure, contact between the contacting surface and the target tissue, and temperature According to some embodiments, a controller 3430 is used to control one or more of the motor 3404, the reciprocating mechanism 108, and the EMR source 3420. In some versions, the controller 3430 takes input from one or more sensors 3432 that measure at least one of the rotational movement 3406 and the reciprocating movement 3410.

Figure 27:
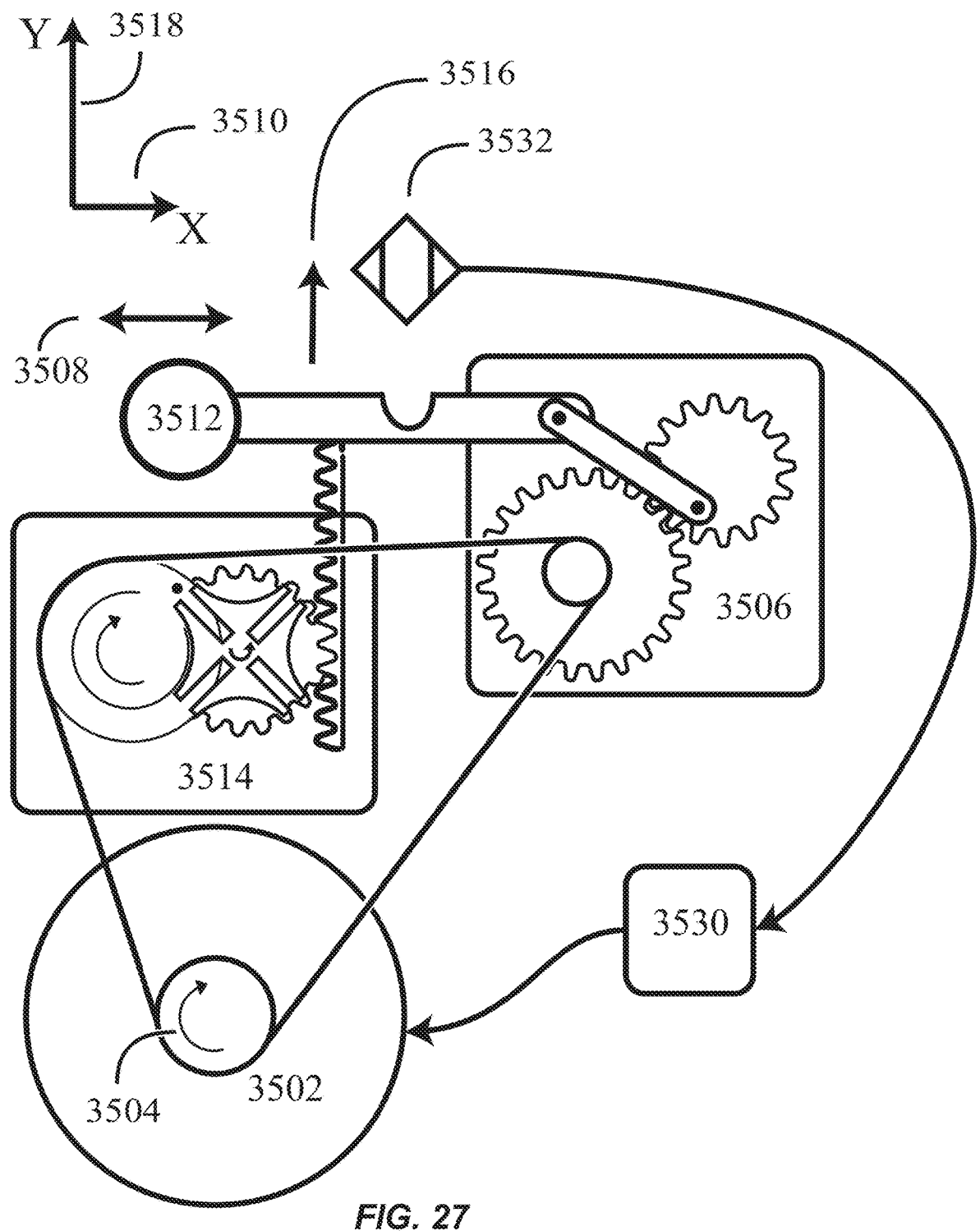
FIG. 27 schematically represents a two-dimensional (2D) beam scanning system, according to some embodiments; and, FIG. 28 is a schematic illustration of a post-objective objective scanning system.

FIG. 27 schematically represents a system 3500 that scans an electromagnetic radiation (EMR) beam in two axes. A motor 3502 generates and delivers a rotational movement 3504 to a reciprocating mechanism 3506 that converts the rotational movement 3504 to a reciprocating movement 3508 along a first scanned axis 3510. According to some embodiments, the reciprocating movement 3508 includes a linear stroke and has a constant velocity over a portion of the linear stroke. A focus optic 3512 is mechanically affixed to an output of the reciprocating mechanism 3506, such that it experiences and moves according to the reciprocating movement 3508. An intermittent mechanism 3514 is operatively coupled with the reciprocating mechanism 3506. The intermittent mechanism 3514 outputs an intermittent movement 3516 intermittently. According to some embodiments, the intermittent mechanism includes one or more of: a ratchet mechanism, a Geneva wheel mechanism, a cam mechanism, and an intermittent gear mechanism. According to some embodiments, the intermittent movement 3516 is linear and acts generally along a second scanned axis 3518, which is generally orthogonal to the first scanned axis 3510.

According to some embodiments, the intermittent mechanism 3514 is configured to (e.g., timed to) introduce the intermittent movement 3516 when the reciprocating movement 3508 is at or near a specific location, for example at a beginning of a stroke, a middle of a stroke, or an end of a stroke.

According to some embodiments, a controller 3530 is used to control one or more of the motor 3502, the reciprocating mechanism 3506, and the intermittent mechanism 3514. In some versions, the controller 3530 takes input from one or more sensors 3532 that measure at least one of the rotational movement 3504, the reciprocating movement 3508, and the intermittent movement 3516.

Post-Objective Scanning

Figure 28:
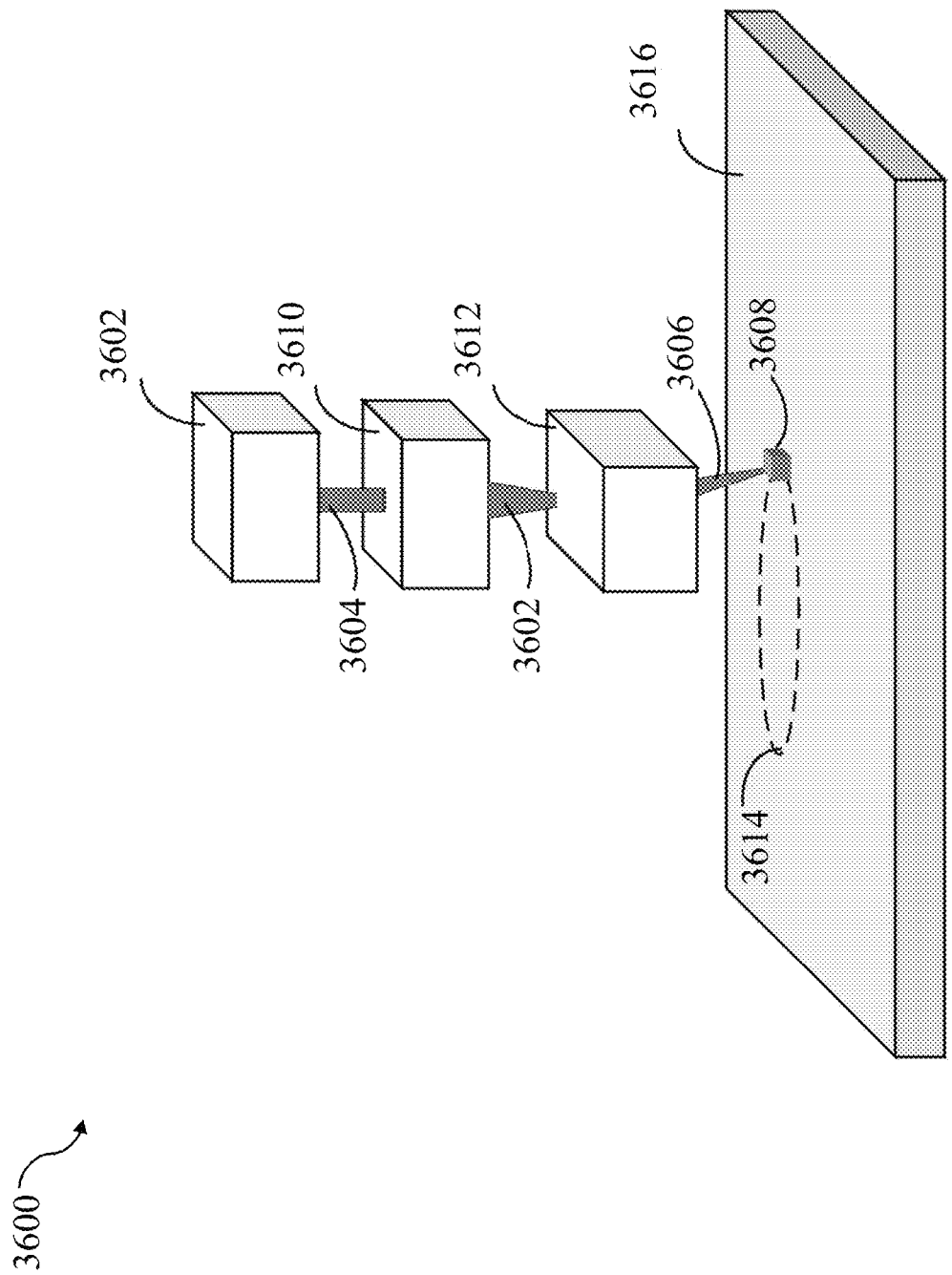

FIG. 28 is a schematic illustration of a post-objective scanning system 3600. The post-objective scanning system 3600 includes an objective 3610 and a scanning unit 3612. The objective 3610 can receive a laser beam 3604 from a laser source 3602 and direct focused laser beam 3606 to the scanning unit 3612. The scanning unit 3612 can receive the focused laser beam 3606 and direct it to a focal region 3608 in the treatment region of a tissue 3616 (e.g., skin). The scanning unit 3612 can allow the focal region 3608 to trace a treatment path 3614. The scanning unit 3612 includes one or more optical elements that can direct the focused laser beam 3606 (or a portion of the focused laser beam 3606) towards the skin.

Example parameters according to some embodiments of pre-objective and post-objective beam scanners are disclosed below in the table below:

Example Scanning Parameters

| Parameter | Typical Minimum | Nominal | Typical Maximum |
|---|---|---|---|
| Treatment Path Distance (mm) | 0.5 | 10 | 100 |
| Focal Volume Pitch, x-y plane (µm) | 1 | 25 | 1000 |
| Focal Volume Pitch, z-axis (µm) | 1 | 50 | 200 |
| Scan Speed, x-y plane (mm/S) | 0.001 | 1000 | 50000 |
| Numerical Aperture of Objective (—) | 0.3 | 0.5 | 0.9 |
| Focal Region Depth Beneath Skin Surface (µm) | 20 | 200 | 2000 |
| Average Power of Laser (W) | 0.5 | 10 | 30 |
| Repetition Rate of Laser (Hz) | 1 | 20000 | C.W. |
| Pulse Duration of Laser (nS) | 1 | 100 | 100000 |
| Energy per Pulse (mJ) | 0.1 | 2 | 20 |
| Wavelength (nm) | 300 | 1064 | 3000 |

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. "Approximately," "substantially," or "about" can include numbers that fall within a range of 1%, or in some embodiments within a range of 5% of a number, or in some embodiments within a range of 10% of a number in either direction (greater than or less than the number) unless otherwise stated or otherwise evident from the context (except where such number would impermissibly exceed 100% of a possible value). Accordingly, a value modified by a term or terms, such as "about," "approximately," or "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure also includes embodiments in which more than one, or all of the group members are present in, employed in, or otherwise relevant to a given product or process. Furthermore, it is to be understood that the disclosed embodiments provide all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the disclosed embodiments where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the disclosed embodiments, or aspects of the disclosed embodiments, is/are referred to as comprising particular elements, features, etc., certain embodiments of the disclosure or aspects of the disclosure consist, or consist essentially of, such elements, features, etc. For purposes of simplicity those embodiments have not in every case been specifically set forth in so many words herein. It should also be understood that any embodiment or aspect of the disclosure can be explicitly excluded from the claims, regardless of whether the specific exclusion is recited in the specification. For example, any one or more active agents, additives, ingredients, optional agents, types of organism, disorders, subjects, or combinations thereof, can be excluded.

Where ranges are given herein, embodiments of the disclosure include embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise. It is also understood that where a series of numerical values is stated herein, the disclosure includes embodiments that relate analogously to any intervening value or range defined by any two values in the series, and that the lowest value may be taken as a minimum and the greatest value may be taken as a maximum. Numerical values, as used herein, include values expressed as percentages.

Although a few variations have been described in detail above, other modifications or additions are possible.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system comprising:
   an electromagnetic radiation (EMR) source configured to generate an EMR beam having a wavelength in a range of about 1200 nm to about 12000 nm;
   a beam shaper comprising a first axicon and a second axicon configured to shape the EMR beam into a transverse ring energy profile;
   an optic configured to converge the shaped EMR beam to a focal point located within a tissue;
   a beam scanning system configured to scan the focal point within the tissue;
   a window assembly located down-beam from the optic configured to transmit the EMR beam and cool the tissue when placed in contact with an outer surface of the tissue, wherein the window assembly comprises:
      a first window;
      a second window separated from the first window; and
      a coolant chamber located between the first window and the second window, wherein the coolant chamber is configured to contain a coolant comprising a fluorocarbon-based fluid that is substantially non-absorbent of the EMR beam; and
   a controller configured to control the EMR source to generate the EMR beam with a plurality of pulses, wherein at least one pulse of the plurality of pulses has a pulse duration that is no less than about 100 microseconds.

2. The system of claim 1, wherein the at least one pulse of the plurality of pulses has a pulse energy that is no greater than about 100 mJ.

3. The system of claim 1, further comprising a chiller configured to cool the coolant to a temperature within a range of about −20° C. to about 20° C.

4. The system of claim 1, wherein the optic is further configured to converge the EMR beam at a numerical aperture (NA) of at least about 0.2.

5. The system of claim 1, further comprising an optical tissue clearing medium located between the window assembly and the tissue, wherein the optical tissue clearing medium comprises at least one of glycerin, polyethylene glycol, and phosphate-buffered saline.

6. The system of claim 1, wherein the controller is configured to control the EMR source to ensure that the window assembly cools the tissue to a predetermined temperature prior to generating the EMR beam.

7. The system of claim 1, wherein the controller is configured to control the EMR source to ensure that the window assembly cools the tissue for a predetermined period prior to generating the EMR beam.

8. The system of claim 1, wherein at least one of the EMR source, the optic, and the beam scanning system is configured to control one or more parameters of the EMR beam, comprising one or more of an inner diameter of the ring-shaped energy profile, an outer diameter of the ring-shaped energy profile, a thickness of the ring-shaped energy profile, and depth of the focal point within the tissue.

9. A method comprising:
   cooling, using a window assembly contacting an outer surface of a tissue, the tissue, wherein the window assembly comprises:
      a first window;
      a second window separated from the first window; and
      a coolant chamber located between the first window and the second window wherein the coolant chamber is configured to contain coolant comprising a fluorocarbon-based fluid that is substantially non-absorbent of the EMR beam;
   generating, using an electromagnetic radiation (EMR) source, an EMR beam having a wavelength in a range of about 1200 nm to about 12000 nm;
   shaping, using a beam shaper comprising a first axicon and a second axicon, the EMR beam to produce a transverse ring energy profile;
   converging, using an optic, the shaped EMR beam to a focal point located within a tissue;
   scanning, using a beam scanning system, the focal point within the tissue; and
   controlling, using a controller, the EMR source to generate the EMR beam with a plurality of pulses, wherein at least one pulse of the plurality of pulses has a pulse duration that is no less than about 100 microseconds.

10. The method of claim 9, wherein the at least one pulse of the plurality of pulses has a pulse energy that is no greater than about 100 mJ.

11. The method of claim 9, further comprising cooling, using a chiller, the coolant to a temperature within a range of about −20° C. to about 20° C.

12. The method of claim 9, wherein converging the EMR beam is performed at a numerical aperture (NA) of at least about 0.2.

13. The method of claim 9, further comprising introducing an optical tissue clearing medium between the window assembly and the tissue, wherein the optical tissue clearing medium comprises at least one of glycerin, polyethylene glycol, and phosphate buffered saline.

14. The method of claim 9, further comprising controlling, using the controller, the EMR source in order to ensure that the window assembly cools the tissue to a predetermined temperature prior to generating the EMR beam.

15. The method of claim 9, further comprising controlling, using the controller, the EMR source in order to ensure that the window assembly cools the tissue for a predetermined period prior to generating the EMR beam.

16. The method of claim 9, further comprising controlling at least one parameter of the EMR beam, comprising one or more of an inner diameter of the ring-shaped energy profile, an outer diameter of the ring-shaped energy profile, a thickness of the ring-shaped energy profile, and depth of the focal point within the tissue.

17. A system comprising:

an electromagnetic radiation (EMR) source configured to generate an EMR beam having a wavelength in a range between about 1400 nm and 3500 nm;

a collimator configured to collimate the EMR beam to a collimated beam width;

a beam shaper comprising a first axicon and a second axicon configured to shape the EMR beam into a transverse ring-shaped energy profile, wherein the first axicon and the second axicon are separated by a separation distance along an optical axis, wherein an inner diameter of the ring-shaped energy profile is related to the separation distance and a thickness of the ring-shaped energy profile is related to the collimated beam width;

an optic configured to converge the EMR beam at a numerical aperture of at least about 0.2 to a focal point located within a tissue;

a beam scanning system configured to scan the focal point within the tissue;

a window assembly located down-beam from the optic configured to transmit the EMR beam and cool the tissue when placed in contact with an outer surface of the tissue, wherein the window assembly comprises:

a first window;

a second window separated from the first window; and a coolant chamber located between the first window and the second window, wherein the coolant chamber is configured to contain a coolant comprising a fluorocarbon-based fluid that is substantially non-absorbent of the EMR beam;

a chiller configured to cool the coolant to a temperature within a range of about −20° C. to about 20° C.;

a controller configured to: control the EMR source in order to ensure that the window assembly cools the tissue to a predetermined temperature or for a predetermined time prior to generating the EMR beam; and, control the EMR source to generate the EMR beam with a plurality of pulses, wherein at least one pulse of the plurality of pulses has a pulse duration that is no less than 100 microseconds; and, wherein at least one of the EMR source, the optic, and the beam scanning system is configured to control one or more parameters of the EMR beam, comprising one or more of the inner diameter of the ring-shaped energy profile, an outer diameter of the ring-shaped energy profile, the thickness of the ring-shaped energy profile, and depth of the focal point within the tissue.

* * * * *